(12) United States Patent
Lockhart et al.

(10) Patent No.: US 8,236,493 B2
(45) Date of Patent: Aug. 7, 2012

(54) METHODS OF ENZYMATIC DISCRIMINATION ENHANCEMENT AND SURFACE-BOUND DOUBLE-STRANDED DNA

(75) Inventors: David J. Lockhart, Del Mar, CA (US);
Mark S. Chee, Del Mar, CA (US);
Martin Digglemann, Nierdedorf (CH);
Dirk Vetter, Weimar-Gaberndorf (DE)

(73) Assignee: Affymetrix, Inc., Santa Clara, CA (US)

( * ) Notice: Subject to any disclaimer, the term of this patent is extended or adjusted under 35 U.S.C. 154(b) by 494 days.

(21) Appl. No.: 12/187,503

(22) Filed: Aug. 7, 2008
(Under 37 CFR 1.47)

(65) Prior Publication Data
US 2010/0216656 A1    Aug. 26, 2010

Related U.S. Application Data

(63) Continuation-in-part of application No. 11/950,213, filed on Dec. 4, 2007, which is a continuation of application No. 11/176,012, filed on Jul. 5, 2005, which is a continuation of application No. 08/533,582, filed on Oct. 18, 1995, now Pat. No. 6,974,666, which is a continuation-in-part of application No. 08/327,687, filed on Oct. 24, 1994, now Pat. No. 5,556,752, and a continuation-in-part of application No. 08/327,522, filed on Oct. 21, 1994, now abandoned, application No. 12/187,503, which is a continuation-in-part of application No. 10/961,341, filed on Oct. 7, 2004, now abandoned, which is a continuation of application No. 09/880,727, filed on Jun. 13, 2001, now Pat. No. 6,858,711, which is a continuation-in-part of application No. 08/882,649, filed on Jun. 25, 1997, now Pat. No. 6,344,316, which is a continuation of application No. PCT/US97/01603, filed on Jan. 22, 1997.

(60) Provisional application No. 60/035,170, filed on Jan. 9, 1997, provisional application No. 60/010,471, filed on Jan. 23, 1996.

(51) Int. Cl.
*C12Q 1/68* (2006.01)

(52) U.S. Cl. ............................................ 435/6

(58) Field of Classification Search .............. None
See application file for complete search history.

(56) References Cited

U.S. PATENT DOCUMENTS

| | | | |
|---|---|---|---|
| 3,352,849 A | 11/1967 | Shen | |
| 3,730,844 A | 5/1973 | Gilham et al. | |
| 3,817,837 A | 6/1974 | Rubenstein et al. | |
| 3,850,752 A | 11/1974 | Schuurs et al. | |
| 3,891,623 A | 6/1975 | Vorbruggen et al. | |
| 3,939,350 A | 2/1976 | Kronick et al. | |
| 3,996,345 A | 12/1976 | Ullman et al. | |
| 4,071,315 A | 1/1978 | Chateau | |
| 4,275,149 A | 6/1981 | Litman et al. | |
| 4,277,437 A | 7/1981 | Maggio | |
| 4,327,073 A | 4/1982 | Huang | |
| 4,366,241 A | 12/1982 | Tom et al. | |
| 4,373,071 A | 2/1983 | Itakura | |
| 4,376,110 A | 3/1983 | David et al. | |
| 4,458,066 A | 7/1984 | Caruthers et al. | |
| 4,483,920 A | 11/1984 | Gillespie et al. | |
| 4,486,539 A | 12/1984 | Ranki et al. | |
| 4,500,707 A | 2/1985 | Caruthers | |
| 4,542,102 A | 9/1985 | Dattagupta et al. | |
| 4,556,643 A | 12/1985 | Paau et al. | |
| 4,562,157 A | 12/1985 | Lowe et al. | |
| 4,563,419 A | 1/1986 | Ranki et al. | |
| 4,584,277 A | 4/1986 | Ullman et al. | |
| 4,591,570 A | 5/1986 | Chang | |
| 4,594,339 A | 6/1986 | Lopez et al. | |
| 4,613,566 A | 9/1986 | Potter | |
| 4,670,380 A | 6/1987 | Dattagupta | |
| 4,677,054 A | 6/1987 | White et al. | |

(Continued)

FOREIGN PATENT DOCUMENTS

CS     133464     10/1969

(Continued)

OTHER PUBLICATIONS

Pease et al. (Proc Natl Acad Sci U S A. May 24, 1994;91(11):5022-6).*
Akita, Y. et al., "Cross-Coupling Reaction of Chloropyrazines with Acetylenes," Chemical & Pharmaceutical Bulletin, 34, 4 A.D., pp. 1447-1458.
Alpers, J., "Putting Genes on a Chip," Science, 264, 1994, pp. 1400-.
Aoyagi, Mitsutoshi et al. "Nucleosides and nucleotides. 115. Synthesis of 3-alkyl-3-deazainosines via palladium-catalyzed intramolecular cyclization: A new conformational lock wi," Tetrahedron Letters, 34, Jan. 1, 1993, pp. 103-106.
Augenlicht, L. H. et al. "Cloning and screening of sewuences expressed in a mouse colon tumor," Cancer Res., 42, Mar. 1982, pp. 1088-1093.

(Continued)

*Primary Examiner* — Christopher M. Babic
(74) *Attorney, Agent, or Firm* — Affymetrix, Inc.

(57) ABSTRACT

Methods for discriminating between fully complementary hybrids and those that differ by one or more base pairs and libraries of unimolecular, double-stranded oligonucleotides on a solid support. In one embodiment, the present invention provides methods of using nuclease treatment to improve the quality of hybridization signals on high density oligonucleotide arrays. In another embodiment, the present invention provides methods of using ligation reactions to improve the quality of hybridization signals on high density oligonucleotide arrays. In yet another embodiment, the present invention provides libraries of unimolecular or intermolecular, double-stranded oligonucleotides on a solid support. These libraries are useful in pharmaceutical discovery for the screening of numerous biological samples for specific interactions between the double-stranded oligonucleotides, and peptides, proteins, drugs and RNA. In a related aspect, the present invention provides libraries of conformationally restricted probes on a solid support. The probes are restricted in their movement and flexibility using double-stranded oligonucleotides as scaffolding. The probes are also useful in various screening procedures associated with drug discovery and diagnosis. The present invention further provides methods for the preparation and screening of the above libraries.

5 Claims, 16 Drawing Sheets

U.S. PATENT DOCUMENTS

| | | |
|---|---|---|
| 4,683,195 A | 7/1987 | Mullis et al. |
| 4,683,202 A | 7/1987 | Mullis |
| 4,689,405 A | 8/1987 | Frank et al. |
| 4,704,353 A | 11/1987 | Humphries et al. |
| 4,711,955 A | 12/1987 | Ward et al. |
| 4,716,106 A | 12/1987 | Chiswell |
| 4,728,502 A | 3/1988 | Hamill |
| 4,728,591 A | 3/1988 | Clark et al. |
| 4,731,325 A | 3/1988 | Palva et al. |
| 4,755,458 A | 7/1988 | Rabbani et al. |
| 4,767,700 A | 8/1988 | Wallace |
| 4,780,504 A | 10/1988 | Buendia et al. |
| 4,812,512 A | 3/1989 | Buendia et al. |
| 4,820,630 A | 4/1989 | Taub |
| 4,833,092 A | 5/1989 | Geysen |
| 4,849,513 A | 7/1989 | Smith et al. |
| 4,855,225 A | 8/1989 | Fung et al. |
| 4,868,103 A | 9/1989 | Stavrianopoulos et al. |
| 4,868,104 A | 9/1989 | Kurn et al. |
| 4,868,105 A | 9/1989 | Urdea et al. |
| 4,874,500 A | 10/1989 | Madou et al. |
| 4,883,750 A | 11/1989 | Whiteley et al. |
| 4,921,805 A | 5/1990 | Gebeyehu et al. |
| 4,923,901 A | 5/1990 | Koester et al. |
| 4,925,785 A | 5/1990 | Wang et al. |
| 4,942,124 A | 7/1990 | Church |
| 4,946,773 A | 8/1990 | Maniatis et al. |
| 4,981,783 A | 1/1991 | Augenlicht |
| 4,987,065 A | 1/1991 | Stavrianopoulos et al. |
| 4,988,617 A | 1/1991 | Landegren et al. |
| 4,992,383 A | 2/1991 | Farnsworth |
| 4,994,373 A | 2/1991 | Stavrianopoulos et al. |
| 4,997,928 A | 3/1991 | Hobbs, Jr. |
| 5,002,867 A | 3/1991 | Macevicz |
| 5,013,669 A | 5/1991 | Peters, Jr. et al. |
| 5,021,550 A | 6/1991 | Zeiger |
| 5,026,840 A | 6/1991 | Dattagupta et al. |
| 5,028,525 A | 7/1991 | Gray et al. |
| 5,028,545 A | 7/1991 | Soini |
| 5,043,265 A | 8/1991 | Tanke et al. |
| 5,047,524 A | 9/1991 | Andrus et al. |
| 5,064,754 A | 11/1991 | Mills |
| 5,082,830 A | 1/1992 | Brakel et al. |
| 5,091,652 A | 2/1992 | Mathies et al. |
| 5,093,245 A | 3/1992 | Keith et al. |
| 5,100,777 A | 3/1992 | Chang |
| 5,141,813 A | 8/1992 | Nelson |
| 5,143,854 A | 9/1992 | Pirrung et al. |
| 5,151,507 A | 9/1992 | Hobbs, Jr. et al. |
| 5,153,319 A | 10/1992 | Ceruther et al. |
| 5,173,260 A | 12/1992 | Zander et al. |
| 5,185,243 A | 2/1993 | Ullman et al. |
| 5,188,963 A | 2/1993 | Stapleton |
| 5,200,051 A | 4/1993 | Cozzette et al. |
| 5,200,312 A | 4/1993 | Oprandy |
| 5,202,231 A | 4/1993 | Drmanac et al. |
| 5,204,268 A | 4/1993 | Matsumoto |
| 5,215,882 A | 6/1993 | Bahl et al. |
| 5,232,829 A | 8/1993 | Longiaru et al. |
| 5,242,794 A | 9/1993 | Whiteley et al. |
| 5,242,796 A | 9/1993 | Prober et al. |
| 5,242,974 A | 9/1993 | Holmes |
| 5,252,296 A | 10/1993 | Zuckermann et al. |
| 5,252,743 A | 10/1993 | Barrett et al. |
| 5,256,549 A | 10/1993 | Urdea et al. |
| 5,262,536 A | 11/1993 | Hobbs, Jr. |
| 5,288,514 A | 2/1994 | Ellman |
| 5,290,925 A | 3/1994 | Fino |
| 5,310,893 A | 5/1994 | Erlich et al. |
| 5,324,633 A | 6/1994 | Fodor et al. |
| 5,328,824 A | 7/1994 | Ward et al. |
| 5,332,666 A | 7/1994 | Prober et al. |
| 5,338,688 A | 8/1994 | Deeg et al. |
| 5,348,855 A | 9/1994 | Dattagupta |
| 5,362,643 A * | 11/1994 | Chang ................ 435/332 |
| 5,389,512 A | 2/1995 | Kwok et al. |
| 5,412,087 A | 5/1995 | McGall et al. |
| 5,422,241 A | 6/1995 | Goldrick et al. |
| 5,424,186 A | 6/1995 | Fodor et al. |
| 5,427,930 A | 6/1995 | Birkenmeyer et al. |
| 5,445,934 A | 8/1995 | Fodor et al. |
| 5,472,842 A | 12/1995 | Stokke et al. |
| 5,474,796 A | 12/1995 | Brennan |
| 5,474,895 A | 12/1995 | Ishii et al. |
| 5,486,452 A | 1/1996 | Gordon et al. |
| 5,489,507 A | 2/1996 | Chehab |
| 5,489,678 A | 2/1996 | Fodor |
| 5,494,810 A | 2/1996 | Barany et al. |
| 5,503,980 A | 4/1996 | Cantor |
| 5,510,270 A | 4/1996 | Fodor et al. |
| 5,512,430 A | 4/1996 | Gong |
| 5,514,543 A | 5/1996 | Grossman et al. |
| 5,514,785 A | 5/1996 | Van Ness et al. |
| 5,516,641 A | 5/1996 | Ullman et al. |
| 5,516,663 A | 5/1996 | Backman et al. |
| 5,518,883 A | 5/1996 | Soini |
| 5,521,065 A | 5/1996 | Whiteley et al. |
| 5,543,292 A | 8/1996 | Imai et al. |
| 5,545,531 A * | 8/1996 | Rava et al. ................ 506/23 |
| 5,556,748 A | 9/1996 | Douglas |
| 5,556,752 A | 9/1996 | Lockhart et al. |
| 5,563,060 A | 10/1996 | Hozier |
| 5,571,639 A | 11/1996 | Hubbell et al. |
| 5,589,329 A | 12/1996 | Winkler et al. |
| 5,599,675 A | 2/1997 | Brenner |
| 5,605,662 A | 2/1997 | Heller |
| 5,608,063 A | 3/1997 | Hobbs, Jr. et al. |
| 5,631,134 A * | 5/1997 | Cantor ................ 435/6 |
| 5,635,400 A | 6/1997 | Brenner |
| 5,679,524 A | 10/1997 | Nikiforov et al. |
| 5,686,243 A | 11/1997 | Royer et al. |
| 5,700,637 A | 12/1997 | Southern |
| 5,728,526 A * | 3/1998 | George et al. ................ 435/6.11 |
| 5,744,305 A | 4/1998 | Fodor et al. |
| 5,750,341 A | 5/1998 | Macevicz |
| 5,795,714 A | 8/1998 | Cantor et al. |
| 5,800,992 A | 9/1998 | Fodor et al. |
| 5,807,522 A | 9/1998 | Brown |
| 5,830,645 A | 11/1998 | Pinkel et al. |
| 5,830,711 A | 11/1998 | Barany et al. |
| 5,837,832 A | 11/1998 | Chee et al. |
| 5,912,148 A | 6/1999 | Eggerding |
| 5,952,174 A | 9/1999 | Nikiforov et al. |
| 5,962,223 A | 10/1999 | Whiteley et al. |
| 5,969,119 A | 10/1999 | Macevicz |
| 5,972,619 A | 10/1999 | Drmanac et al. |
| 6,007,987 A | 12/1999 | Cantor et al. |
| 6,018,041 A | 1/2000 | Drmanac et al. |
| 6,025,136 A | 2/2000 | Drmanac |
| 6,027,880 A | 2/2000 | Cronin et al. |
| 6,040,138 A | 3/2000 | Lockhart et al. |
| 6,054,270 A | 4/2000 | Southern |
| 6,103,463 A | 8/2000 | Chetverin et al. |
| 6,110,426 A | 8/2000 | Shalon et al. |
| 6,174,998 B1 | 1/2001 | Muhlegger et al. |
| 6,211,158 B1 | 4/2001 | Seela et al. |
| 6,306,597 B1 | 10/2001 | Macevicz |
| 6,974,666 B1 | 12/2005 | Lockhart et al. |

FOREIGN PATENT DOCUMENTS

| | | |
|---|---|---|
| DE | 3505287 | 9/1985 |
| DE | 19509038 | 9/1996 |
| EP | 063810 | 11/1982 |
| EP | 132621 | 6/1984 |
| EP | 142299 | 5/1985 |
| EP | 159719 | 10/1985 |
| EP | 171150 | 2/1986 |
| EP | 173339 | 3/1986 |
| EP | 225807 | 6/1987 |
| EP | 232967 | 8/1987 |
| EP | 235726 | 9/1987 |
| EP | 237362 | 9/1987 |
| EP | 252683 | 1/1988 |
| EP | 259031 | 3/1988 |
| EP | 266787 | 5/1988 |
| EP | 281927 | 9/1988 |
| EP | 0303459 | 10/1988 |

| | | |
|---|---|---|
| EP | 320308 | 6/1989 |
| EP | 322311 | 6/1989 |
| EP | 336731 | 10/1989 |
| EP | 337498 | 10/1989 |
| EP | 360940 | 4/1990 |
| EP | 392546 | 10/1990 |
| EP | 535242 | 4/1993 |
| EP | 717113 | 6/1996 |
| EP | 721016 | 7/1996 |
| EP | 931726 | 7/1999 |
| FR | 2559783 | 9/1985 |
| FR | 2551442 | 4/1987 |
| GB | 2156074 | 10/1985 |
| JP | 61109797 | 5/1986 |
| SE | 8403151 | 12/1984 |
| WO | WO 8403151 | 8/1984 |
| WO | WO 8501051 | 3/1985 |
| WO | WO 8910977 | 11/1989 |
| WO | WO 8911548 | 11/1989 |
| WO | WO 9000626 | 1/1990 |
| WO | WO 9003370 | 4/1990 |
| WO | WO 9003382 | 4/1990 |
| WO | WO 9004652 | 5/1990 |
| WO | WO 9010713 | 9/1990 |
| WO | WO 9015070 | 12/1990 |
| WO | WO 9115600 | 10/1991 |
| WO | WO 9202258 | 2/1992 |
| WO | WO 9210092 | 6/1992 |
| WO | WO 9210588 | 6/1992 |
| WO | WO 9200091 | 9/1992 |
| WO | WO 9311262 | 6/1993 |
| WO | WO 9316094 | 8/1993 |
| WO | WO 9317126 | 9/1993 |
| WO | WO 9322680 | 11/1993 |
| WO | WO 9411530 | 5/1994 |
| WO | WO 9502681 | 1/1995 |
| WO | WO 9504160 | 2/1995 |
| WO | WO 9504594 | 2/1995 |
| WO | WO 9504833 | 2/1995 |
| WO | WO 9504834 | 2/1995 |
| WO | WO 9509248 | 4/1995 |
| WO | WO 9500530 | 5/1995 |
| WO | WO 9511995 | 5/1995 |
| WO | WO 9515970 | 6/1995 |
| WO | WO 9520681 | 8/1995 |
| WO | WO 9521944 | 8/1995 |
| WO | WO 9525116 | 9/1995 |
| WO | WO 9528480 | 10/1995 |
| WO | WO 9530774 | 11/1995 |
| WO | WO 9535505 | 12/1995 |
| WO | WO 9617958 | 6/1996 |
| WO | WO 9628460 | 9/1996 |
| WO | WO 9710365 | 3/1997 |
| WO | WO 9727317 | 7/1997 |
| WO | WO 9728176 | 8/1997 |
| WO | WO 9729212 | 8/1997 |
| WO | WO 9739120 | 10/1997 |
| WO | WO 9811104 | 3/1998 |
| WO | WO 9831836 | 7/1998 |
| WO | WO 0006771 | 2/2000 |

OTHER PUBLICATIONS

Augenlicht, L. H. et al. "Expression of cloned sequences in biopsies of human colonic tissue and in colonic carcinoma cells induced to differentiate in vitro," Cancer Res., 47, Nov. 15, 1987, pp. 6017-6021.
Avila, J. L. et al. "Biological action of pyrazolopyrimidine derivatives against Trypanosoma cruzi. Studies in vitro and in vivo," Comp Biochem.Physiol C., 86, 1987, pp. 49-54.
Bains et al., "A novel method for nuccleic acid sequence determination," J. Theor. Biol., 135:303-307 (1988).
Barringer, K. J. et al. "Blunt-end and single-strand ligations by Escherichia coli ligase: influence on an in vitro amplification scheme," Gene, 89, Apr. 30, 1990, pp. 117-122.
Bartsch, R. A. et al. "Cloning of mRNA sequences from the human colon: preliminary characterisation of defined mRNAs in normal and neoplastic tissues," Br.J.Cancer, 54, Nov. 1986, pp. 791-798.
Basnak, I. et al., "Some 6-Aza-5-Substituted-2'-Deoxyuridines Show Potent and Selective Inhibition of Herpes Simplex Virus 1 Tymidine Kinase", Nucleosides & Nucleotides, 17 (1-3), (1998), pp. 187-206.

Beabealashvilli, R. S. et al. "Nucleoside 5'-triphosphates modified at sugar residues as substrates for calf thymus terminal deoxynucleotidyl transferase and for AMV reverse transcriptase," Biochim.Biophys.Acta, 868, Nov. 13, 1986, pp. 136-144.
Bergeron, et al., "Reagents for the Stepwise Functionalization of Spermine," J.Org.Chem., 53, 1998, pp. 3108-3111.
Bergstrom, D. E.,"Design and Synthesis of Heterocyclic Carboxamides as Natural Nucleic Acid Base Mimics," Nucleosides Nucleotides, 15, 1996, pp. 59-68.
Berk and Sharp, "Sizing and mapping of early adenovirus mRNAs by gel electrophoresis of S1 endonuclease-digested hybrids," Cell, 12:721-732 (1997).
Berman and Young, "The interaction of intercalating drugs with nucleic acids," Annu. Rev. Biophys. Bioeng., 10:87-114 (1981).
Billings, P. R. et al. "New techniques for physical mapping of the human genome," FASEB J., 5, Jan. 1991, pp. 28-34.
Bobek, M., "Nucleic Acids Components and their Analogues. XCVII Synthesis of 5-Hydroxmethyl-6-Aza-2'-Deoxyuridine and 5-Hydroxymethyl-6-Aza-2'-Deoxycytidine," Collection Czechoslov.Chem.Commun., 32, 2008, pp. 3581-3586.
Bock et al., "Selection of single-stranded DNA molecules that bind and inhibit human thrombin," Nature, 355:564-566 (1992).
Boyle, A. L. et al. "Differential distribution of long and short interspersed element sequences in the mouse genome: chromosome karyotyping by fluorescence in situ hybridization," Proc.Natl.Acad. Sci.U.S.A, 87, Oct. 1990, pp. 7757-7761.
Brock, K. V. et al. "Rapid fluorescence detection of in situ hybridization with biotinylated bovine herpesvirus-1 DNA probes," J.Vet. Diagn.Invest, 1, Jan. 1989, pp. 34-38.
Brody, R. S. et al. "The purification of orotidine-5'-phosphate decarboxylase from yeast by affinity chromatography," J.Biol. Chem., 254, May 25, 1979, pp. 4238-4244.
Brossalina, E., J. Am. Chem. Soc., 115:796-797(1933).
Broude et al.,"Enhanced DNA sequencing by hybridization," Proc. Natl. Acad. Sci. USA, 91:3072-3076 (1994).
Canard, B. et al. "Catalytic editing properties of DNA polymerases," Proc.Natl.Acad.Sci.U.S.A, 92, Nov. 21, 1995, pp. 10859-10863.
Cantor et al., Biophysical Chemistry—Part I: The conformation of biological molecules, W.H. Freeman and Co., San Francisco, CA, pp. 163-176.
Cantor et al., "Report on the sequencing by hybridization workshop," Genomics, 13:1378-1383 (1992).
Chattopadhya et al., "X-ray structure of a DNA hairpin molecule," Nature, 334:175-179 (1988).
Carrano, A. V. et al. "A high-resolution, fluorescence-based, semiautomated method for DNA fingerprinting," Genomics, 4, Feb. 1989, pp. 129-136.
Cech, D.,"New Approaches Toward the Synthesis of Non-Radioactively Labelled Nucleoside Triphoshates as Terminators for DNA Sequencing," Collection Czechoslov.Chem.Commun., 61, 1996, pp. S297-S300.
Chee, M. et al. "Accessing genetic information with high-density DNA arrays," Science, 274, Oct. 25, 1996, pp. 610-614.
Chehab, F. F. et al. "Detection of sickle cell anaemia mutation by colour DNA amplification," Lancet, 335, Jan. 6, 1990, pp. 15-17.
Chehab, F. F. et al. "Detection of specific DNA sequence by fluorescence amplification: a color complementation assay," Proc.Natl. Acad.Sci.U.S.A. 86, Dec. 1989, pp. 9178-9182.
Chernetskii, V. P.,"Anomalous Nucleosides and Related Compounds XIV. Derivatives of 6-Azacytidine," Chemical Abstracts, 74, 1971.
Chidgeavadez, Z. G.,"2', 3'—Dideoxy-3' Aminionucleoside 5'-Triphosphates are the terminators of DNA Synthesis Catalyzed by DNA Polymerases," Nucleic Acids Res., 12, 1984, pp. 1671-1686.
Chu,"General Synthesis of 2', 3'-dideoxynucleosides and 2',3' didehydro-2',3'-dideoxynucleosides," J.Org.Chem., 54, 1989, pp. 2217-2225.
Cottam, H. B. et al. "New adenosine kinase inhibitors with oral antiinflammatory activity: synthesis and biological evaluation," J.Med.Chem., 36, Oct. 29, 1993, pp. 3424-3430.
Cook et al., "Detection of protein-DNA complex formation by time-resolved fluorescence depolarization of bound ethidium bromide," Anal. Biochem., 190:331-339 (1990).

Cotton & Wilkinson, Advanced Inorganic Chemistry, Chapter 8, 5th Ed., John Wiley & sons, p. 278 (1993).
Craig, A. G. et al. "Labelling oligonucleotides to high specific activity (I)," Nucleic Acids Res., 17, Jun. 26, 1989, pp. 4605-4610.
Craig, A. G. et al. "Ordering of cosmid clones covering the herpes simplex virus type I (HSV-I) genome: a test case for fingerprinting by hybridisation," Nucleic Acids Res., 18, May 11, 1990, pp. 2653-2660.
Curriden, M.,"A New Evidence Tool—First use of Mitochondrial DNA Test in a U.S. Criminal Trial," ABA Journal, Nov. 1996.
Cuniberti and Guenza, "Environment-induced changes in DNA conformation as probed by ethidium bromide fluorescence," *Biophys. Chem.*, 38:11-22 (1990).
Danshcer, J. et al.,"Autometallographic Silver Amplification of Colloidal Gold," J.Hisotech, 15, 1993, pp. 201-207.
Deininger, Prescott,"Molecular cloning: A laboratory manual : 2nd ed. Edited by J.. Cold Spring Harbor Laboratory Press, Cold Spring Harbor, NY, 1989 (in 3 volumes)," Analytical Biochemistry, 186, Apr. 1990, pp.
Depelley, J. et al.,"New Non-Aromatic Triazinic Nucleosides: Synthesis and Antiretroviral Evaluation of Beta-Ribosylamine Nucleoside Analogs," Nucleosides & Nucleotides, 15, 1996, pp. 995-1008.
Dramanc, et al.,"Partial Sequencing by Oligo-Hybridization: Concept and Applications in Genome Analysis The first International Conference on Electrophoresis Supercomputing and the Human Genome," 1990, pp. 60-74.
Drmanac, R. et al. "DNA sequence determination by hybridization: a strategy for efficient large-scale sequencing," Science, 260, Jun. 11, 1993, pp. 1649-1652.
Drmanac, R. et al. "Reliable hybridization of oligonucleotides as short as six nucleotides," DNA Cell Biol., 9, Sep. 1990, pp. 527-534.
Drmanac, R. et al. "Sequencing by hybridization: towards an automated sequencing of one million M13 clones arrayed on membranes," Electrophoresis, 13, Aug. 1992, pp. 566-573.
Drmanac, R. et al. "Sequencing of megabase plus DNA by hybridization: theory of the method," Genomics, 4, Feb. 1989, pp. 114-128.
Dueholm, et al., "2,3-dideoxy-furanoses in convergent synthesis of 2',3'-dideoxy nucleosides", Synthesis, (1992), pp. 1-22.
Duncan, et al., Analytical Biochemistry, 169:104-108 (1988).
Durand, M., et al., Nucleic Acid Res., 18(21):6353-5469 (1990).
Edo, K. et al.,"Studies on Pyrimidine Derivatives IX Coupling Reaction of Mono-Substituted Acetylenes with Iodopyrimidines," Chemical & Pharmaceutical Bulletin, 26, 1978, pp. 3843-3850.
Eggers, M. et al. "A microchip for quantitative detection of molecules utilizing luminescent and radioisotope reporter groups," Biotechniques, 17, Sep. 1994, pp. 516-525.
Ekins, R. P. et al. "Multianalyte microspot immunoassay—microanalytical "compact disk" of the future," Clin.Chem., 37, Nov. 1991, pp. 1955-1967.
Ekins, Roger et al. "Development of microspot multi-analyte ratiometric immunoassay using dual fluorescent-labelled antibodies," Analytica Chimica Acta, 227, 1989, pp. 73-96.
Ekins, Roger et al. "Fluorescence spectroscopy and its application to a new generation of high sensitivity, multi-microspot, multianalyte, immunoassay," Clinica Chimica Acta, 194, Dec. 17, 1990, pp. 91-114.
Evans, G. A. et al. "Physical mapping of complex genomes by cosmid multiplex analysis," Proc.Natl.Acad.Sci.U.S.A, 86, Jul. 1989, pp. 5030-5034.
Evans, Glen A.,"Molecular cloning: A laboratory manual. Second edition. vols. 1, 2, and 3. Current protocols in molecular biology. vols. 1 and 2: By J. Sambrook, E. F. Fritsch, and T. Maniatis. Cold Spring Harbor, New York: Cold Spring Harbor Laboratory Press. (1989). 1626 pp. $115.00. Edited by F. M. Ausubel, R. Brent, R. E. Kingston, D. D. Moore, J. G. Seidman, J. A. Smith, and K. Struhl. New York: Greene Publishing Associates and John Wiley & Sons. (1989). 1120 pp. $255.00," Cell, 61, Apr. 6, 1990, pp. 17-18.
Ezaki, T. et al. "Small-scale DNA preparation for rapid genetic identification of *Campylobacter* species without radioisotope," Microbiol.Immunol., 32, 1988, pp. 141-150.
Famulok et al., "In vitro selection of specific ligand-binding nucleic acids," *Angew. Chem. Int. Ed. Engl.*, 31:979-988 (1992).

Fan, Y.S. et al. "Mapping small DNA sequence by fluorescence in situ hybridization directly on banded metaphase chromosomes," Proc. Natl.Acad.Sci.U.S.A, 87, Aug. 1990, pp. 6223-6227.
Feldman, W. et al. "Gary code masks for sequencing by hybridization," Genomics, 23, Sep. 1, 1994, pp. 233-235.
Fodor, et al. "Light directed, spatially addressable parallel chemical synthesis," Science, 251, 1991, 767-773.
Fodor et al., "Light-directed, spatially addressable parallel chemical synthesis," *Science*, 251:767-777 (1991).
Fodor et al., *Research Article*, p. 767 (1991).
Frank, R. et al. "Simultaneous synthesis and biological applications of DNA fragments: an efficient and complete methodology," Methods Enzymol., 154, 1987, pp. 221-249.
Frank and Doring, "Simultaneous multiple peptide synthesis under continuous flow conditions on cellulose paper discs as segmental solid supports," *Tetrahedron*, 44:6031-6040 (1988).
Freskos, J. N.,"Synthesis of 2'-Deoxypyrimidine Nucleosides Via Copper (I) Iodine Catalysis," Nucleosides & Nucleotides, 8, 1989, pp. 549-555.
Frumgarts, L. A. et al. "[Preparation of fluorescent-labeled DNA and its use as a probe in molecular hybridization]," Bioorg.Khim., 12, Nov. 1986, pp. 1508-1513.
Galas et al., "DNAse footprinting: a simple method for the detection of protein-DNA binding specificity," *Nucl. Acids Res.*, 5:3157-3170 (1978).
Galushko, S. V. et al. "Relationship between retention parameters in reversed-phase high-performance liquid chromatography and antitumour activity of some pyrimidine bases and nucleosides," Journal of Chromatography A, 547, Jun. 28, 1991, pp. 161-166.
Galushko, J . . . , et al., "Synthesis and antibody-mediated detection of oligonucleotides containing multiple 2,4-dinitrophenyl reporter groups", Nucleic Acids Research, 21 (8), (1993), pp. 1705-1712.
Gergen et al, "Filter Replicas and permanent collections of recombinant DNA plasmids," Nucleic Acids Res. 7:2115-2135, 1979.
Geysen et al., "Strategies for epitope analysis using peptide synthesis," *J. Immun. Meth.*, 105:259-274 (1987).
Galushko, S. V.,"Reversed-phase HPLC of N4-and O'-Derivatives of 6-azacytidine," Chemical Abstracts, 111, 1990.
Grzybowski, J. et al. "Synthesis and antibody-mediated detection of oligonucleotides containing multiple 2,4-dinitrophenyl reporter groups," Nucleic Acids Res., 21, Apr. 25, 1993, pp. 1705-1712.
Guatelli, J. C. et al. "Isothermal, in vitro amplification of nucleic acids by a multienzyme reaction modeled after retroviral replication," Proc.Natl.Acad.Sci.U.S.A, 87, Mar. 1990, pp. 1874-1878.
Gumerlock, P. H. et al. "RAS enzyme-linked immunoblot assay discriminates p21 species: a technique to dissect gene family expression," Anal.Biochem., 180, Jul. 1989, pp. 158-168.
Guo, Z. et al. "Direct fluorescence analysis of genetic polymorphisms by hybridization with oligonucleotide arrays on glass supports," Nucleic Acids Res., 22, Dec. 11, 1994, pp. 5456-5465.
Haase, et al, "Detection of two viral genomes in single cells by double-label hybridization in situ and color microradioautography," Science 227, 189-192, 1985.
Hamilton, H. et al.,"C4-Substituted 1-beta-D-Ribofuranosylpyrazolo[3,4-d]Pyrimidines as Adenosine Agonist Analogues," J.Med.Chem., 26, 1993, pp. 1601-1606.
Hanahan, D. et al. "Plasmid screening at high colony density," Gene, 10, Jun. 1980, pp. 63-67.
Hanahan, D. et al. "Plasmid screening at high colony density," Methods Enzymol., 100, 1983, pp. 333-342.
Hard and Kearns, "Reduced DNA flexibility in complexes with a type II DNA binding protein," *Biochemistry*, 29:959-965 (1990).
Herrlein, et al.,"57.3'-Amino-Modified Nucleotides Useful as Potent Chain Terminators for Current DNA Sequencing Methods," Helvecta Chemica Acta, 77, 1994, pp. 586-596.
Hobbs, Jr. F. W. et al.,"Palladium-Catalyzed Synthesis of Alkynylamino Nucleosides. A Universal Linker for Nucleic Acids," J.Org.Chem., 54, 1989, pp. 3420-3422.
Hod, Y.,"A simplified ribonuclease protection assay," Biotechniques, 13, Dec. 1992, pp. 852-854.
Hoheisel, J. D., "Application of hybridization techniques to genome mapping and sequencing," Trends Genet., 10, Mar. 1994, pp. 79-83.

Holy, "Oligonucleotidic Compounds. XVII Synthesis of Oligonucleotides Containing 6-Azauriding ad 6-Azacytidine," Collection Czechoslov.Chem.Commun., 32, 1967, pp. 2980-2997.

Hopman, A. H. et al. "Bi-color detection of two target DNAs by non-redioactive in situ hybridization," Histochemistry, 85, 1986, pp. 1-4.

Houghten et al., "Generation and use of synthetic peptide combinatorial libraries for basic research and drug discovery," *nature*, 354:84-86 (1991).

Izuta, S., "Chain Termination with Sugar-Modified Nucleotide Analogs in the DNA Synthesis by DNA Polymerase Y," Nucleotides, 15, 1996, pp. 683-692.

Johnson, W. T. et al. "The synthesis and stability of oligodeoxyribonucleotides containing the deoxyadenosine mimic 1-(2'-deoxy-beta-D-ribofuranosyl)imidazole-4-carboxamide," Nucleic Acids Res., 25, Feb. 1, 1997, pp. 559-567.

Johnston, et al., "Chemistry of High Density arrays Factors Impacting Issues of Complexity," Microbial & Comparative Genomics, 1996.

Kallioniemi, A. et al. "Comparative genomic hybridization for molecular cytogenic analysis of solid tumors," Science, 258, Oct. 30, 1992, pp. 818-821.

Kallioniemi, O. P. et al. "Optimizing comparative genomic hybridization for analysis of DNA sequence copy number changes in solid tumors," Genes Chromosomes.Cancer, 10, Aug. 1994, pp. 231-243.

Kerkof, P. R. et al. "A procedure for making simultaneous determinations of the relative levels of gene transcripts in tissues or cells," Anal.Biochem., 188, Aug. 1, 1990, pp. 349-355.

Khrapko, K. R. et al. "A method for DNA sequencing by hybridization with oligonucleotide matrix," DNA Seq., 1, 1991, pp. 375-388.

Khrapko, K. R. et al. "An oligonucleotide hybridization approach to DNA sequencing," FEBS Lett., 256, Oct. 9, 1989, pp. 118-122.

Kievits, T. et al. "Rapid subchromosomal localization of cosmids by nonradioactive in situ hybridization," Cytogenet.Cell Genet., 53, 1990, pp. 134-136.

Kimura, J. et al. "An immobilized enzyme membrane fabrication method using an ink jet nozzle," Biosensors, 4, 1989, pp. 41-52.

Kitazawa, S. et al. "In situ DNA-RNA hybridization using in vivo bromodeoxyuridine-labeled DNA probe," Histochemistry, 92, 1989, pp. 195-199.

Kleinfeld, D. et al. "Controlled outgrowth of dissociated neurons on patterned substrates," J.Neurosci., 8, Nov. 1988, pp. 4098-4120.

Kohara, Y. et al. "The physical map of the whole *E. coli* chromosome: application of a new strategy for rapid analysis and sorting of a large genomic library," Cell, 50, Jul. 31, 1987, pp. 495-508.

Kohler, P., "Synthese von Desoxyribonucleosid-Monophosphaten und-Triphosphaten mit 2 (1 H)—Pyrimidinon, 2 (1 H)—Pyridinon und 4-Amino-2(1 H)—Pyridinon als Basen," Helvecta Chemica Acta, 63, 1980, pp. 2488-2494.

Kozal, M. J. et al. "Extensive polymorphisms observed in HIV-1 clade B protease gene using high-density oligonucleotide arrays," Nat.Med., 2, Jul. 1996, pp. 753-759.

Krug, M. et al. "Reversal of T4 RNA ligase," Biochemistry, 21, Apr. 13, 1982, pp. 1858-1864.

Kutateladze, Tamata et al. "3'-Deoxy-3'-aminonucleoside 5'-triphosphates—Terminators of RNA synthesis, catalyzed by DNA-dependent RNA polymerase from *Escherichia coli*," FEBS Letters, 153, Mar. 21, 1983, pp. 420-426.

Kwoh, D. Y. et al. "Transcription-based amplification system and detection of amplified human immunodeficiency virus type 1 with a bead-based sandwich hybridization format," Proc.Natl.Acad.Sci.U. S.A, 86, Feb. 1989, pp. 1173-1177.

Lam et al., "A new type of synthetic peptide library for identifying ligand-binding activity," *Nature*, 354:82-84.

Landegren, U. et al. "A ligase-mediated gene detection technique," Science, 241, Aug. 26, 1988, pp. 1077-1080.

Langer, P. R. et al. "Enzymatic synthesis of biotin-labeled polynucleotides: novel nucleic acid affinity probes," Proc.Natl.Acad. Sci.U.S.A, 78, Nov. 1971, pp. 6633-6637.

Lanier, L. L. et al. "Human lymphocyte subpopulations identified by using three-color immunofluorescene and flow cytometry analysis: correlation of Leu-2, Leu-3, Leu-7, Leu-8, and Leu-11 cell surface antigen expression," J.Immunol., 132, Jan. 1984, pp. 151-156.

Lasky, L. A. et al. "Messenger RNA prevalence in sea urchin embryos measured with cloned cDNAs," Proc.Natl.Acad.Sci.U.S.A, 77, Sep. 1980, pp. 5317-5321.

Lazurkevich, Z. V., "Growth Activity of 6-Substituted Azauracils," Chemical Abstracts, 102, 1985.

Le Bec, C., "Derivatives of Imidazole-4-Carboxamide as Substrated for Various DNA Polymerases," Nucleosides Nucleotides, 167, 1997, pp. 1301-1302.

Lee and Vacquier et al., "Reusable cDNA libraries coupled to magnetic beads," *Anal. Biochem.*, 206:206-207 (1992).

Lennon, G. G. et al. "Hybridization analyses of arrayed cDNA libraries," Trends Genet., 7, Oct. 1991, pp. 314-317.

Lichter, P. et al. "Fluorescence in situ hybridization with Alu and L1 polymerase chain reaction probes for rapid characterization of human chromosomes in hybrid cell lines," Proc.Natl.Acad.Sci.U.S. A, 87, Sep. 1990, pp. 6634-6638.

Lichter, P. et al. "High-resolution mapping of human chromosome 11 by in situ hybridization with cosmid clones," Science, 247, Jan. 5, 1990, pp. 64-69.

Lichter, P. et al. "Is non-isotopic in situ hybridization finally coming of age?," Nature, 345, May 3, 1990, pp. 93-94.

Lichter, P. et al. "Rapid detection of human chromosome 21 aberrations by in situ hybridization," Proc.Natl.Acad.Sci.U.S.A, 85, Dec. 1988, pp. 9664-9668.

Lipshutz, R. J. et al. "Using oligonucleotide probe arrays to access genetic diversity," Biotechniques, 19, Sep. 1995, pp. 442-447.

Lockhart, D., et al. "Expression Monitoring By Hybridization To High Density Oligonucleotide Arrays," Nat.Biotechnol., US0014839, 1996, pp. 1675-1680.

Loken, M. R. et al. "Three-color immunofluorescence analysis of Leu antigens on human peripheral blood using two lasers on a fluorescence-activated cell sorter," Cytometry, 5, Mar. 1984, pp. 151-158.

Lopez-Galindez et al., "Characterization of genetic variation and 3'-azido-3'-deoxythmidine-resistance mutations of human immunodeficiency virus by the RNase A mismatch cleavage method," *Proc. Natl. Acad. Sci. USA*, 88:4280-4284.

Lu, X. et al. "Differential screening of murine ascites cDNA libraries by means of in vitro transcripts of cell-cycle-phase-specific cDNA and digital image processing," Gene, 86, Feb. 14, 1990, pp. 185-192.

Ludwig, "Rapid and efficient Synthesis of Nucleoside 5'-0-(1-Thiotriphosphates), 5'-triphosphates and 2', 3'-Cyclophosphorothioates using 2-chloro-4H-1,3,2-Benzodioxaphosphorin-4-one," J.Org. Chem., 54, 1989, pp. 631-635.

Lysov, DNA Sequencing by oligonucleotide hybridization, In The First Int'l. Conf. Electrophoresis Supercomputing and the Human Genome, World Scientific, pp. 157-1630, Apr. 1990.

Lysov, et al., "A New Method for Determining the DNA Nucleotide Sequence by Hybridization with Oligonucleotides," Doklady Biochemistry, 303, 1989, pp. 436-438, 1989.

Lysov et al., *Dokl. Akad. Nauk SSSR*, 303:1508-1511 (1988) (*See* footnote provided, p. 436).

Ma, M.Y-X., et al., "Design and Synthesis of RNA Miniduplexes via a Synthetic Linker Approach," Biochemistry, 32:1751-1758 (1993).

Markiewicz, W.T., et al., Nucleic Acids Res., 17: 7149-7157 (1989).

Masiakowski, P. et al. "Cloning of cDNA sequences of hormone-regulated genes from the MCF-7 human breast cancer cell line," Nucleic Acids Res., 10, Dec. 20, 1982, pp. 7895-7903.

Maskos, U. et al. "A Study of oligonucleotide reassociation using large arrays of oligonucleotides synthesised on a glass support," Nucleic Acids Res., 21, Oct. 11, 1993, pp. 4663-4669.

Medlin, J., "The amazing shrinking laboratory," Environ.Health Perspect., 103, Mar. 1995, pp. 244-246.

Meinkoth, J. et al. "Hybridization of nucleic acids immobilized on solid supports," Anal.Biochem., 138, May 1, 1984, pp. 267-284.

Mergny et al., "Intercalation of ethidium bromide into a triple stranded oligonucleotide," *Nucleic Acids Res.*, 19:1521-1526 (1991).

Michaels, F. et al. "Molecular approaches to genome analysis: a strategy for the construction of ordered overlapping clone libraries," Comput.Appl.Biosci., 3, Sep. 1987, pp. 203-210.

Mikkelsen, T. et al. "Genetics of the maglignant progression of astrocytoma," J.Cell Biochem., 46, May 1991, pp. 3-8.

Mirkin, C. A. et al. "A DNA-based method for rationally assembling nanoparticles into macroscopic materials," Nature, 382, Aug. 15, 1996, pp. 607-609.

Misura, K.,"Biotinyl and Phosphotyrosinyl Phosporamidite Derivatives useful in the Incorporation of Multiple Reporter Groups on Synthetic Oligonucleotides," Nucleic Acids Res., 18, 1990, pp. 4345-4354.

Mitchell, W. L. et al. "Synthesis and antiviral properties of 5-(2-substituted vinyl)-6-aza-2'-deoxyuridines," J.Med.Chem., 29, May 1986, pp. 809-816.

Monaco, et al., "Human genome linking with cosmids and yeast artificial chromosomes," Abstract from CSHS p. 90, 1989.

Morrison, L. E. et al. "Solution-phase detection of polynucleotides using interacting fluorescent labels and competitive nybridization," Anal.Biochem., 183, Dec. 1989, pp. 231-244.

Murphy et al., "Long-range photoinduced electron transfer through a DNA helix," Science, 262:1025-1029 (1993).

Myers et al., "Detection of single base substitutions in total genomic DNA," Nature, 313:495-498 (1985).

Nakamori, S. et al. "A simple and useful method for simultaneous screening of elevated levels of expression of a variety of oncogenes in malignant cells," Jpn.J.Cancer Res., 79, Dec. 1988, pp. 1311-1317.

Nederlof, P. M. et al. "Multiple fluorescence in situ hybridization," Cytometry, 11, 1990, pp. 126-131.

Needels et al., "Generation and screening of an oligonucleotide-encoded synthetic peptide library," *Proc. Natl. Acad. Sci. USA*, 90:10700-10704 (1993).

Nelson, P. S. et al. "Oligonucleotide labeling methods. 3. Direct labeling of oligonucleotides employing a novel, non-nucleosidic, 2-aminobutyl-1,3-propanediol backbone," Nucleic Acids Res., 20, Dec. 11, 1992, pp. 6253-6259.

New England Biolabs Catalog 1993/1994.

Nguyen, C. et al. "Differential gene expression in the murine thymus assayed by quantitative hybridization of arrayed cDNA clones," Genomics, 29, Sep. 1, 1995, pp. 207-216.

Niedballa, U. et al. "A general synthesis of N-glycosides. I. Synthesis of pyrimidine nucleosides," J.Org.Chem., 39, Dec. 13, 1974, pp. 3654-3660.

Nishida, Masakazu et al. "Facile perfluoroalkylation of uracils and uridines at the C-5 position," Journal of Fluorine Chemistry, 63, Jul. 1993, pp. 43-52.

Nowak, R.,"Entering the postgenome era," Science, 270, Oct. 20, 1995, pp. 368-369, 371.

Ohlmeyer, Mhj, et al., Proc. Natl. Acad. Science USA, 90:10922-10926 (1993).

Ohsawa, A.,"Alkynylation of Halopyridazines and their N-Oxides," Chemical & Pharmaceutical Bulletin, 28, 1980, pp. 3488-3493.

Parham, "Immunology. Deconstructing the MHC," Nature, 360:300-301 (1992).

Pankiewicz, K. W. et al. "Nucleosides-126 : Selective methylation of the C-nucleoside, [psi]-isocytidine and its 2$-deoxy analog. Synthesis of 1-methyl, 3-methyl and 4-o-methyl derivatives," Tetrahedron, 40, 1984, pp. 33-38.

Pease, A. C.,"Light-Generated Oligonucleotide Arrays for Rapid DNA Sequence Analysis," Proc National Acad Science, 91, 1994, pp. 5022-5026.

Petrie, C. R. et al. "A novel biotinylated adenylate analogue derived from pyrazolo[3,4-d]pyrimidine for labeling DNA probes," Bioconjug.Chem., 2, Nov. 1991, pp. 441-446.

Pevzner, P. A. et al. "Improved chips for sequencing by hybridization," J.Biomol.Struct.Dyn., 9, Oct. 1991, pp. 399-410.

Pietu, G. et al. "Novel gene transcripts preferentially expressed in human muscles revealed by quantitative hybridization of a high density cDNA array," Genome Res., 6, Jun. 1996, pp. 492-503.

Pirrung, Michael C. et al. "A convenient procedure for the deprotection of silylated nucleosides and nucleotides using triethylamine trihydrofluoride," Bioorganic & Medicinal Chemistry Letters, 4, Jun. 9, 1994, pp. 1345-1346.

Pochet, S. et al. "Ambigous Base pairing of 1-(2-Deoxy-beta-D-Riboluranosyl)Imidazole-4-Carboxamide During PCR", Nucleosides & Nucleotides, 16 (7-9), (1997),pp. 1749-1752).

Pochet, S. et al. "Synthesis and enzymatic polymerisation of 5-amino-1-(2'-deoxy-beta-D-ribofuranosyl)imidazole-4-carboxamide-5'-triphosphate," Nucleic Acids Res., 18, Dec. 11, 1990, pp. 7127-7131.

Pochet.,"Enzymatic Synthesis of 1-(2-deoxy-beta-D-ribofuranosyl) Imidazole-4-Carboxamide, a Simplified DNA Building Block," Bioorganic & Medicinal Chemistry Letters, 5, 1995, pp. 1679-1684.

Poustka, A. et al. "Molecular approaches to mammalian genetics," Cold Spring Harb.Symp.Quant.Biol., 51 Pt 1, 1986, pp. 131-139.

Prober, J. M. et al. "A system for rapid DNA sequencing with fluorescent chain-terminating dideoxynucleotides," Science, 238, Oct. 16, 1987, pp. 336-341.

Prystas, M.,"Nucleic Acids Components and their Analogues. CXXI. Glycosylation of 6-Azathymine by the Silylation Process," Collection Czechoslov.Chem.Commun., 34, 1969, pp. 1104-1107.

Reid, Graeme A.,"Molecular cloning: A laboratory manual, 2nd edn : by J. Sambrook, E. F. Fritsch and T. Maniatis, Cold Spring Harbor Laboratory Press, 1989. $115.00 (3 vols; 1659 pages) ISBN 0 87969 309 6," Trends in Biotechnology, 9, Jan. 1991, pp. 213-214.

Rideout, J. L. et al. "Pyrazolo[3,4-d]pyrimidine ribonucleosides as anticoccidials. 2. Synthesis and activity of some nucleosides of 4-(alkylamino)-1H-pyrazolo[3, 4-d]pyrimidines," J.Med.Chem., 25, Sep. 1982, pp. 1040-1044.

Robins,"Nucleic Acid Related Compounds, 42. A General Procedure for the Effcient Deoxygenation of Secondary Alcohols, Regiospecific and Steroselective Conversation of Ribonucleosides to 2' Synthesis and Activity of Some Nucleosides of 4-(Alkylamino)-1H-Pyrazolo [3,4-d Pyrimidines," Journal of American Chemical Society, 105, 1983, pp. 4059-4065.

Robins,"Potential Purine Antagonists. I. Synthesis of some 4,6-Substituted Pyrazolo [3,4-d] pyrimidines," Journal of American Chemical Society, 78, 1995, pp. 784-790.

Rosemeyer, H.,"Stereoelectronics Effects of Modified Purines on the Sugar Conformation of Nucleosides and Fluorescence Properties," Nucleosides Nucleotides, 16, 1997, pp. 821-828.

Saiki, R. K. et al. "Genetic analysis of amplified DNA with immobilized sequence-specific oligonucleotide probes," Proc.Natl.Acad.Sci.U.S.A, 86, Aug. 1989, pp. 6230-6234.

Sala, M. et al. "Ambiguous base pairing of the purine analogue 1-(2-deoxy-beta-D-ribofuranosyl)-imidazole-4-carboxamide during PCR," Nucleic Acids Res., 24, Sep. 1, 1996, pp. 3302-3306.

Sambrook,"Bacteriophage T4 RNA Ligase (Bactriophage T4-Infected *E. coli*)," Molecular Cloning: A Laboratory Manual; 2nd edition, 1989, pp. 5.66-5.69

Sambrook et al., "Molecular Cloning: A Laboratory Manual," *Cold Spring Harbor Laboratory Press*, Cold Spring Harbor, NY, pp. 5.80; 7.58-7.78 (1989).

Scaria et al., "Binding of ethidium bromide to a DNA triple helix. Evidence for intercalation," *J. Biol. Chem.*, 266:5417-5423 (1991).

Scharf, S. J. et al. "HLA class II allelic variation and susceptibility to pemphigus vulgaris," Proc.Natl.Acad.Sci.U.S.A, 85, May 1988, pp. 3504-3508.

Schena, M. et al. "HD-Zip proteins: members of an Arabidopsis homeodomain protein superfamily," Proc.Natl.Acad.Sci.U.S.A, 89, May 1, 1992, pp. 3894-3898.

Schena, M. et al. "Parallel human genome analysis: microarray-based expression monitoring of 1000 genes," Proc.natl.Acad.Sci.U.S.A, 93, Oct. 1, 1996, pp. 10614-10619.

Schena, M. et al. "Quantitative monitoring of gene expression patterns with a complementary DNA microarray," Science, 270, Oct. 20, 1995, pp. 467-470.

Schena, M. et al. "Structure of homeobox-leucine zipper genes suggests a model for the evolution of gene families," Proc.Natl.Acad.Sci.U.S.A, 91, Aug. 30, 1994, pp. 8393-8397.

Schena, M. et al. "The HAT4 gene of *Arabidopsis* encodes a developmental regulator," Genes Dev., 7, Mar. 1993, pp. 367-379.

Shenk et al., "Biochemical method for mapping mutational alterations in DNA with S1 nucleas: the location of deletions and temperature-sensitive mutations in simian virus 40," *Proc. Natl. Acad. Sci. USA*, 72:989-993 (1975).

Schena, M.,"Genome analysis with gene expression microarrays," Bioessays, 18, May 1996, pp. 427-431.

Schober, A. et al. "Accurate high-speed liquid handling of very small biological samples," Biotechniques, 15, Aug. 1993, pp. 324-329.

Seela, F.,"131 8-Aza 7-Deaza-2'-deoxyguanosine: Phosphoramidite Synthesis and Properties of Ocanucleotides," Helvecta Chemica Acta, 71, 1988, pp. 1191-1198.

Seela, F.,"193.8 Aza-7 deazaadenine N8-andN9-(Beta-D-2'-Deoxyribfuranosides): Building Blocks for Automated DNA Synthesis and Properties of Oligodeoxyribonucleotides," Helvecta Chemica Acta, 71, 1988, pp. 1813-1823.

Seela, F.,"Alternating d(G-C)3 and d (C-G)3 Hexanucletides Containing 7-Deaza-2'-Deoxyguanosine in Place of dG," Nucleic Acids Res., 17, 1989, pp. 901-910.

Seela, F.,"Synthesis of 7-Alkynated 8-Aza-7-Deaza-2'-Deoxyadenosines via the Pd-Catalysed Cross-Coupling Reaction," J.Chem.Society, 1998, pp. 3233-3239.

Seela, F.,"Synthesis of Oligonucleotides Containing Pyrazolo [3,4-d] Pyrimidines: The Influence of 7-Substituted 8-Aza-7-Deazaadenines on the Duplex Structure and Stability," J.Chem.Society, 1999, pp. 479-488.

Shalon, D. et al. "A DNA microarray system for analyzing complex DNA samples using two-color fluorescent probe hybridiztion," Genome Res., 6, Jul. 1996, pp. 639-645.

Shalon,"DNA Micro Arrays: A New Tool for Genetic Analysis," Thesis, Stanford University, 1995.

Sim, G. K. et al. "Use of a cDNA library for studies on evolution and developmental expression of the chorion multigens families," Cell, 18, Dec. 1979, pp. 1303-1316.

Southern, E. M. et al. "Analyzing and comparing nucleic acid sequences by hybridization to arrays of oligonucleotides: evaluations using experimental models," Genomics, 13 Aug. 1992, pp. 1008-1017.

Southern, E. M. et al. "Arrays of complementary oligonucleotides for analysing the hybridisation behaviour of nucleic acids," Nucleic Acids Res., 22, Apr. 25, 1994, pp. 1368-1373.

Southern et al., "Analyzing and comparing nucleic acid sequences by hybridization to arrays of oligonucleotides: evaluation using experimental models," *Genomics*, 13:1008-1017 (1992).

Stille, J. K.,"Stereospecific Palladium-Catalyzed Coupling Reactions of Vinyl Iodides with Acetylenic Tin Reagents," Journal of American Chemical Society, 109, Apr. 1, 1987, pp. 2138-2152.

Stimpson, D. I. et al. "Real-time detection of DNA hybridization and melting on oligonucleotide arrays by using optical wave guides," Proc.Natl.Acad.Sci.U.S.A, 92, Jul. 3, 1995, pp. 6379-6383.

Strezoska et al., "DNA sequencing by hybridization: 100 bases read by a non-gel-based method," *Proc. Natl. Acad. Sci. USA*, 88:10089-10093 (1991).

Takahashi, N. et al. "High-density cDNA filter analysis of the expression profiles of the genes preferentially expressed in human brain," Gene, 164, Oct. 27, 1995, pp. 219-227.

Tanji, K.,"Studies on Pyrimidine Derivatives XXVII. Synthesis of 2-and 4-Pyrimidinyl Ketones by Means of the Hydration of Alkynylprimidines," Chemical & Pharmaceutical Bulletin, 30, May 1982, pp. 1865-1867.

Theisen, P. et al. "Fluorescent dye phosphoramidite labelling of olingonucleotides," Nucleic Acids Symp.Ser., 1992, pp. 99-100.

Titus, J. A. et al. "Texas Red, a hydrophilic, red-emitting flurophore for use with fluorescein in dual parameter flow microfluorometric and fluorescence microscopic studies," J.Immunol.Methods, 50, 1982, pp. 193-204.

Tkachuk, D. C. et al. "Detection of bcr-abl fusion in chronic myelogeneous leukemia by in situ hybridization," Science, 250, Oct. 26, 1990, pp. 559-562.

Tuerk and Gold, "Systematic evolution of ligands by exponential enrichment: RNA ligands to bacteriophage T4 DNA polymerase," *Science*, 249:505-510 (1990).

Turchinskii, M. F. et al. "[Multiple hybridization in genome analysis. 1. Reaction of diamine and bisulfite with cytosine for the introduction of nonradioactive markers into DNA]," Mol.Biol.(Mosk), 22, Nov. 1988, pp. 1545-1552.

Uhlenbeck, Olke C. et al. "2 T4 RNA Ligase,", vol. 15, 1982, pp. 31-58.

Urdea, M. S. et al. "A comparison of non-radioisotopic hybridization assay methods using fluorescent, chemiluminescent and enzyme labeled synthetic oligodeoxyribonucleotide probes," Nucleic Acids Res., 16, Jun. 10, 1988, pp. 4937-4956.

Urdea, M. S. et al. "A novel method for the rapid detection of specific nucleotide sequences in crude biological samples without blotting or radioactivity; application to the analysis of hepatitis B virus in human serum," Gene, 61, 1987, pp. 253-264.

Wages, John M. et al. "High-Performance Liquid Chromatography Analysis of PCR Products,", 1995, pp. 140-153.

Wallace, R. B. et al. "Hybridization of synthetic oligodeoxyribonucleotides to phi chi 174 DNA: the effect of single base pair mismatch," Nucleic Acids Res., 6, Aug. 10, 1979, pp. 3543-3557.

Wang, D. G. et al. "Large-scale identification, mapping, and genotyping of single-nucleotide polymorphisms in the human genome," Science, 280, May 15, 1998, pp. 1077-1082.

White et al., New York: McGraw-Hill, pp. 127-128 (1978).

Widacki, S. M. et al. "Biochemical differences in Qa-2 antigens expressed by Qa-2+,6+ and Qa-2+,6-strains. Evidence for differential expression of the Q7 and Q9 genes," Mol.Immunol., 27, Jun. 1990, pp. 559-570.

Winter et al., "A method to detect and characterize point mutations in transcribed genes: amplification and overexpression of the mutant c-Ki-ras allele in human tumor cells," *Proc. Natl. Acad. Sci. USA*, 82:7575-7579 (1985).

Wojczewski, C.,"Synthesis and Application of 3'-Amino-Dye-Terminators for DNA Sequencing," Nucleosides & Nucleotides, 16, 1997, pp. 751-754.

Wooley, A. T. et al. "Ultra-high-speed DNA fragment separations using microfabricated capillary array electrophoresis chips," Proc. Natl.Acad.Sci.U.S.A, 91, Nov. 22, 1994, pp. 11348-11352.

Wu, D. Y. et al. "Direct analysis of single nucleotide variation in human DNA and RNA using in situ dot hybridization," DNA, 8, Mar. 1989, pp. 135-142.

Wu, Dan Y. et al. "The ligation amplification reaction (LAR)—Amplification of specific DNA sequences using sequential rounds of template-dependent ligation," Genomics, 4 May 1989, pp. 560-569.

Wu, F. Y. et al. "Synthesis and properties of adenosine-5'-triphosphoro-gamma-1-(5-sulfonic acid)naphthyl ethylamidate: a fluorescent nucleotide substrate for DNA-dependent RNA polymerase from *Escherichia coli*," Arch.Biochem.Biophys., 246, May 1, 1986, pp. 564-571.

Wu and Wallance, "Specificity of the nick-closing activity of bacteriophage T4 DNA ligase," *Gene*, 76:245-254 (1989).

Yarbrough, L. R. et al. "Synthesis and properties of fluorescent nucleotide substrates for DNA-dependent RNA polymerases," J.Biol.Chem., 254, Dec. 10, 1979, pp. 12069-12073.

Young, W. S., III,"Simultaneous use of digoxigenin- and radiolabeled oligodeoxyribonucleotide probes for hybridization histochemistry," Neuropeptides, 13, May 1989, pp. 271-275.

Yu, H. et al. "Cyanine dye dUTP analogs for enzymatic labeling of DNA probes," Nucleic Acids Res., 22, Aug. 11, 1994, pp. 3226-3232.

Zhu, Z. et al. "Directly labeled DNA probes using fluorescent nucleotides with different length linkers," Nucleic Acids Res., 22, Aug. 25, 1994, pp. 3418-3422.

* cited by examiner

```
                          n
position       5'....AAAGAAAAAGACAGTACTAAATGGA.(SEQ ID NO:5)
TARGET     n   3'           tttttttNtgtcatga  (SEQ ID NO:6)
probe     n+1  3'            tttttcNgtcatgat  (SEQ ID NO:7)
          n+2  3'             ttttcgNtcatgatt (SEQ ID NO:8)
```

Fig. 5

CORRESPONDING
NUCLEOTIDE

```
A C T G T T A G C T A A T T G G        REF SEQ (SEQ ID NO:12)
        C A A T C G A                  PROBE FROM FIRST PROBE SET
        C A A C C G A ⎫ CORRESPONDING PROBES
        C A A G C G A ⎬ FROM SECOND, THIRD AND
        C A A A C G A ⎭ FOURTH PROBE SETS
```

INTERROGATION
POSITION

Fig. 11

```
A C T G T T A G C T A A T T G G           REF SEQ (SEQ ID NO:12)
G G G C A A T C G A G G G G G G           PROBE FROM FIRST PROBE SET
                                          (SEQ ID NO:13)
```

LEADING          SEGMENT OF        TRAILING
SEQUENCE   COMPLEMENTARITY   SEQUENCE

Fig. 12

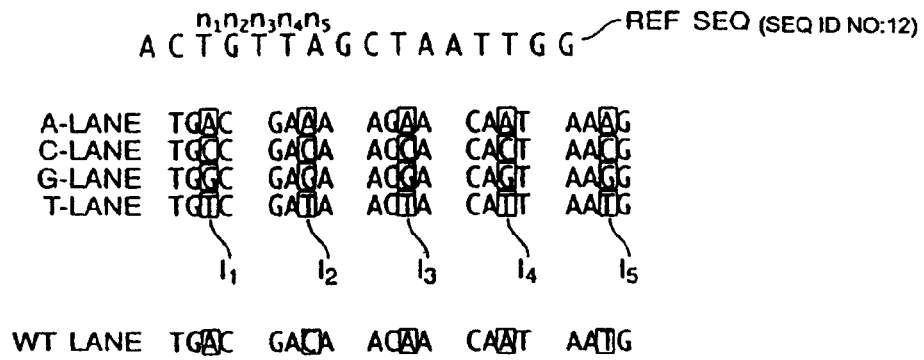
Fig. 14A
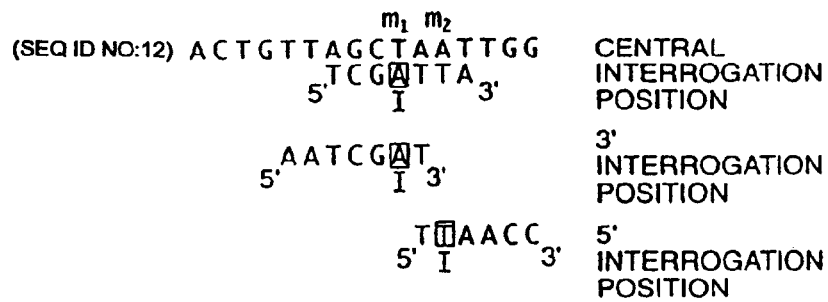
Fig. 14B
GGGXCCCTTAF (SEQ ID NO:26)
CCCAGGG
CCCCGGG
CCCGGGG
CCCTGGG
AGGGAAT
CGGGAAT
GGGGAAT
TGGGAAT
Fig. 14C

```
                  n₁   n₂   n₃ ╱─ CORRESPONDING NUCLEOTIDES
         A C T G  T T A G  C T A A T T G G ─── REF SEQ (SEQ ID NO:12)
                 C A A T C G A ─── PROBE FROM FIRST SET
                  I₁   I₂   I₃ ─── INTERROGATION POSITIONS

C A A T C G A  ⎫ CORRESPONDING PROBES
         C G A T C G A  ⎬ FROM SECOND, THIRD AND
         C T A T C G A  ⎭ FOURTH PROBE SETS
           I₁

C A A A C G A  ⎫ CORRESPONDING PROBES
         C A A C C G A  ⎬ FROM FIFTH, SIXTH AND
         C A A G C G A  ⎭ SEVENTH PROBE SETS
               I₂

C A A T C A A  ⎫ CORRESPONDING PROBES
         C A A T C C A  ⎬ FROM EIGHTH, NINTH AND
         C A A T C T A  ⎭ TENTH PROBE SETS
                   I₃
```

Fig. 16

METHODS OF ENZYMATIC DISCRIMINATION ENHANCEMENT AND SURFACE-BOUND DOUBLE-STRANDED DNA

CROSS-REFERENCE TO RELATED APPLICATIONS

This application is a continuation-in-part of U.S. Ser. No. 11/950,213, filed Dec. 4, 2007, which is a continuation of U.S. Ser. No. 11/176,012, filed Jul. 5, 2005, which is a continuation of U.S. Ser. No. 08/533,582, filed Oct. 18, 1995, now U.S. Pat. No. 6,974,666, which is a continuation-in-part of U.S. Ser. No. 08/327,687 filed Oct. 24, 1994, now U.S. Pat. No. 5,556,752 and which also is a continuation-in-part of U.S. Ser. No. 08/327,522, filed Oct. 21, 1994, now abandoned. This application is also a continuation-in-part of U.S. Ser. No. 10/961,341, filed Oct. 7, 2004, now abandoned, which is a continuation of U.S. Ser. No. 09/880,727, filed Jun. 13, 2001, now U.S. Pat. No. 6,858,711, which is a continuation-in-part of application U.S. Ser. No. 08/882,649, filed Jun. 25, 1997, now U.S. Pat. No. 6,344,316, which is a continuation of PCT/US97/01603, filed Jan. 22, 1997, which claims benefit of provisional U.S. Ser. No. 60/035,170, filed Jan. 9, 1997, and which also claims benefit of provisional U.S. Ser. No. 60/010,471, filed Jan. 23, 1996. Each of these applications is incorporated herein in its entirety by reference for all purposes.

GOVERNMENT RIGHTS

Research leading to the invention was funded in part by an NTH Grant No. R01HG00813-03 and the government may have certain rights to the invention.

BACKGROUND OF THE INVENTION

The relationship between structure and function of macromolecules is of fundamental importance in the understanding of biological systems. Such relationships are important to understanding, for example, the functions of enzymes, structural proteins, and signalling proteins, the ways in which cells communicate with one another, the mechanisms of cellular control and metabolic feedback, etc.

Genetic information is critical in the continuation of life processes. Life is substantially informationally based, and genetic content controls the growth and reproduction of the organism and its complements. Proteins, which are critical features of all living systems, are encoded by the genetic materials of the cell. More particularly, the properties of enzymes, functional proteins and structural proteins are determined by the sequence of amino acids from which they are made. As such, it has become very important to determine the genetic sequences of nucleotides which encode the enzymes, structural proteins and other effectors of biological functions. In addition to the segments of nucleotides which encode polypeptides, there are many nucleotide sequences which are involved in the control and regulation of gene expression.

The human genome project is an example of a project that is directed toward determining the complete sequence of the genome of the human organism. Although such a sequence would not necessarily correspond to the sequence of any specific individual, it will provide significant information as to the general organization and specific sequences contained within genomic segments from particular individuals. It will also provide mapping information useful for further detailed studies. The need for highly rapid, accurate, and inexpensive sequencing technology is nowhere more apparent than in a demanding sequencing project such as this. To complete the sequencing of a human genome will require the determination of approximately $3 \times 10^9$, or 3 billion, base pairs.

The procedures typically used today for sequencing include the methods described in Sanger, et al., *Proc. Natl. Acad. Sci. USA* 74:5463-5467 (1977), and Maxam, et al., *Methods in Enzymology* 65:499-559 (1980). The Sanger method utilizes enzymatic elongation with chain terminating dideoxy nucleotides. The Maxam and Gilbert method uses chemical reactions exhibiting specificity of reactants to generate nucleotide specific cleavages. Both methods, however, require a practitioner to perform a large number of complex, manual manipulations. For example, such methods usually require the isolation of homogeneous DNA fragments, elaborate and tedious preparation of samples, preparation of a separating gel, application of samples to the gel, electrophoresing the samples on the gel, working up the finished gel, and analysis of the results of the procedure.

Alternative techniques have been proposed for sequencing a nucleic acid. PCT patent Publication No. 92/10588, incorporated herein by reference for all purposes, describes one improved technique in which the sequence of a labeled, target nucleic acid is determined by hybridization to an array of nucleic acid probes on a substrate. Each probe is located at a positionally distinguishable location on the substrate. When the labeled target is exposed to the substrate, it binds at locations that contain complementary nucleotide sequences. Through knowledge of the sequence of the probes at the binding locations, one can determine the nucleotide sequence of the target nucleic acid. The technique is particularly efficient when very large arrays of nucleic acid probes are utilized. Such arrays can be formed according to the techniques described in U.S. Pat. No. 5,143,854 issued to Pirrung, et al. See also, U.S. application Ser. No. 07/805,727, both of which are incorporated herein by reference for all purposes.

When the nucleic acid probes are of a length shorter than the target, one can employ a reconstruction technique to determine the sequence of the larger target based on affinity data from the shorter probes. See, U.S. Pat. No. 5,202,231 issued to Drmanac, et al., and PCT patent Publication No. 89/10977 issued to Southern. One technique for overcoming this difficulty has been termed sequencing by hybridization or SBH. Assume, for example, that a 12-mer target DNA, i.e., 5'-AGCCTAGCTGAA (SEQ ID NO:1), is mixed with an array of all octanucleotide probes. If the target binds only to those probes having an exactly complementary nucleotide sequence, only five of the 65,536 octamer probes (i.e., 3'-TCGGATCG, CGGATCGA, GGATCGAC, GATCGACT, and ATCGACTT) will hybridize to the target. Alignment of the overlapping sequences from the hybridizing probes reconstructs the complement of the original 12-mer target:

```
    TCGGATCG                (SEQ ID NO: 2)
     CGGATCGA
      GGATCGAC
       GATCGACT
        ATCGACTT

TCGGATCGAGTT
```

Although such techniques have been quite useful, it would be helpful to have additional methods which can effectively discriminate between fully complementary hybrids and those that differ by one or more base pairs.

In addition to knowing the genetic sequences of the nucleotides which encode the enzymes, structural proteins and other effectors of biological functions, it is important to known how such species interact A number of biochemical processes involve the interaction of some species, e.g., a drug, a peptide or protein, or RNA, with double-stranded DNA. For example, protein/DNA binding interactions are involved with a number of transcription factors as well as with tumor suppression associated with the p53 protein and the genes contributing to a number of cancer conditions. As such, it would be advantages to have methods for preparing libraries of diverse double-stranded nucleic acid sequences and probes which can be used, for example, in screening studies for the determination of binding affinity exhibited by binding proteins, drugs or RNA.

Methods of synthesizing desired single stranded DNA sequences are well known to those of skill in the art. In particular, methods of synthesizing oligonucleotides are found in, for example, *Oligonucleotide Synthesis: A Practical Approach*, Gait, ed., IRL Press, Oxford (1984), incorporated herein by reference in its entirety for all purposes. Synthesizing unimolecular double-stranded DNA in solution has also been described. See, Durand, et al., *Nucleic Acids Res.* 18:6353-6359 (1990) and Thomson, et al., *Nucleic Acids Res.* 21:5600-5603 (1993), the disclosures of both being incorporated herein by reference.

Solid phase synthesis of biological polymers has been evolving since the early "Merrifield" solid phase peptide synthesis, described in Merrifield, *J. Am. Chem. Soc.* 85:2149-2154 (1963), incorporated herein by reference for all purposes. Solid-phase synthesis techniques have been provided for the synthesis of several peptide sequences on, for example, a number of "pins." See, e.g., Geysen, et al., *J. Immun. Meth.* 102:259-274 (1987), incorporated herein by reference for all purposes. Other solid-phase techniques involve, for example, synthesis of various peptide sequences on different cellulose disks supported in a column. See, Frank and Doling, *Tetrahedron* 44:6031-6040 (1988), incorporated herein by reference for all purposes. Still other solid-phase techniques are described in U.S. Pat. No. 4,728,502 issued to Hamill and WO 90/00626 (Beattie, inventor). Unfortunately, each of these techniques produces only a relatively low density array of polymers. For example, the technique described in Geysen, et al. is limited to producing 96 different polymers on pins spaced in the dimensions of a standard microtiter plate.

Improved methods of forming large arrays of oligonucleotides, peptides and other polymer sequences in a short period of time have been devised. Of particular note, Pirrung, et al., U.S. Pat. No. 5,143,854 (see also PCT Application No. WO 90/15070) and Fodor, et al., PCT Publication No. WO 92/10092, all incorporated herein by reference, disclose methods of forming vast arrays of peptides, oligonucleotides and other polymer sequences using, for example, light-directed synthesis techniques. See also, Fodor, et al., *Science*, 251:767-777 (1991), incorporated herein by reference for all purposes. These procedures are now referred to as VLSIPS™ procedures.

More particularly, in the Fodor, et al., PCT application, an elegant method is described for using a computer-controlled system to direct a VLSIPS™ procedure. Using this approach, one heterogenous array of polymers is converted, through simultaneous coupling at a number of reaction sites, into a different heterogenous array. See, U.S. application Ser. Nos. 07/796,243 and 07/980,523, the disclosures of which are incorporated herein for all purposes.

Although such techniques have been quite useful, it would be advantageous to have additional methods for preparing libraries of diverse double-stranded nucleic acid sequences and probes which can be used, for example, in screening studies for the determination of binding affinity exhibited by binding proteins, drugs or RNA.

SUMMARY OF THE INVENTION

In one embodiment, the present invention provides methods of using nuclease treatment to improve the quality of hybridization signals on high density oligonucleotide arrays. More particularly, in one such method, an array of oligonucleotides is combined with a labelled target nucleic acid to form target-oligonucleotide hybrid complexes. Thereafter, the target-oligonucleotide hybrid complexes are treated with a nuclease and, in turn, the array of target-oligonucleotide complexes are washed to remove non-perfectly complementary target-oligonucleotide hybrid complexes. Following nuclease treatment, the target:oligonucleotide hybrid complexes which are perfectly complementary are more readily identified. From the location of the labelled targets, the oligonucleotide probes which hybridized with the targets can be identified and, in turn, the sequence of the target nucleic acid can be more readily determined or verified.

In another embodiment, the present invention provides methods wherein ligation reactions are used to discriminate between fully complementary hybrids and those that differ by one or more base pairs. In one such method, an array of oligonucleotides is generated on a Substrate (in the 3' to 5' direction) using any one of the methods described herein. Each of the oligonucleotides in the array is shorter in length than the target nucleic acid so that when hybridized to the target nucleic acid, the target nucleic acid generally has a 3' overhang. In this embodiment, the target nucleic acid is not necessarily labelled. After the array of oligonucleotides has been combined with the target nucleic acid to form target-oligonucleotide hybrid complexes, the target-oligonucleotide hybrid complexes are contacted with a ligase and a labelled, ligatable probe or, alternatively, with a pool of labelled, ligatable probes. The ligation reaction of the labelled, ligatable probes to the 5' end of the oligonucleotide probes on the substrate will occur, in the presence of the ligase, only when the target-oligonucleotide hybrid has formed with correct base-pairing near the 5' end of the oligonucleotide probe and where there is a suitable 3' overhang of the target nucleic acid to serve as a template for hybridization and ligation. After the ligation reaction, the substrate is washed (multiple times if necessary) with water at a temperature of about 40° C. to 50° C. to remove the unbound target nucleic acid and the labelled, unligated probes. Thereafter, a quantitative fluorescence image of the hybridization pattern is obtained by scanning the substrate with, for example, a confocal microscope, and labelled oligonucleotide probes, i.e., the oligonucleotide probes which are perfectly complementary to the target nucleic acid, are identified. Using this information, the sequence of the target nucleic acid can be more readily determined or verified.

In a further embodiment, the present invention provides libraries of unimolecular, double-stranded oligonucleotides. Each member of the library is comprised of a solid support, an optional spacer for attaching the double-stranded oligonucleotide to the support and for providing sufficient space between the double-stranded oligonucleotide and the solid support for subsequent binding studies and assays, an oligonucleotide attached to the spacer and further attached to a second complementary oligonucleotide by means of a flexible linker, such that the two oligonucleotide portions exist in a double-stranded configuration. More particularly, the members of the libraries of the present invention can be represented by the formula:

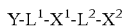

in which Y is a solid support, $L^1$ is a bond or a spacer, $L^2$ is a flexible linking group, and $X^1$ and $X^2$ are a pair of complementary oligonucleotides. In a specific aspect of the invention, the library of different unimolecular, double-stranded oligonucleotides can be used for screening a sample for a species which binds to one or more members of the library.

In yet another embodiment, the present invention provides a library of different conformationally-restricted probes attached to a solid support is provided. The individual members each have the formula:

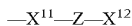

in which $X^{11}$ and $X^{12}$ are complementary oligonucleotides and Z is a probe having sufficient length such that $X^{11}$ and $X^{12}$ form a double-stranded oligonucleotide portion of the member and thereby restrict the conformations available to the probe. In a specific aspect of the invention, the library of different conformationally-restricted probes can be used for screening a sample for a species which binds to one or more probes in the library.

In yet another embodiment, the present invention provides libraries of intermolecular, doubly-anchored, double-stranded oligonucleotides, each member of the library having the formula:

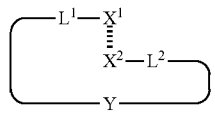

in which Y represents a solid support, $X^1$ and $X^2$ represent a pair of complementary or partially complementary oligonucleotides, and $L^1$ and $L^2$ each represent a bond or a spacer. Typically, $L^1$ and $L^2$ are the same and are spacers having sufficient length such that $X^1$ and $X^2$ can form a double-stranded oligonucleotide. The non-covalent binding which exists between $X^1$ and $X^2$ is represented by the dashed line.

According to yet another aspect of the present invention, methods and devices for the bioelectronic detection of duplex formation are provided.

According to still another aspect of the invention, an adhesive is provided which comprises two surfaces of complementary oligonucleotides.

A further understanding of the nature and advantages of the inventions herein may be realized by reference to the remaining portions of the specification and the attached drawings.

BRIEF DESCRIPTION OF THE DRAWINGS

FIG. 5 illustrates probe tiling strategy used to generate the probes.

FIG. 11 illustrates the basic tiling strategy. The figure illustrates the relationship between an interrogation position (I) and a corresponding nucleotide (n) in the reference sequence, and between a probe from the first probe set and corresponding probes from second, third and fourth probe sets.

FIG. 12 illustrates the segment of complementarity in a probe from the first probe set.

FIG. 14A illustrates the exemplary arrangement of lanes on a chip. The chip shows four probe sets, each having five probes and each having a total of five interrogation positions (I1-I5), one per probe.

FIG. 14B illustrates a tiling strategy for analyzing closing spaced mutations.

FIG. 14C illustrates a tiling strategy for avoiding loss of signal due to probe self-annealing.

FIG. 16 illustrates the block tiling strategy. The perfectly matched probe has three interrogation positions. The probes from the other probe sets have only one of these interrogation positions.

DETAILED DESCRIPTION OF THE INVENTION AND PREFERRED EMBODIMENTS

Table of Contents

Figure 1:
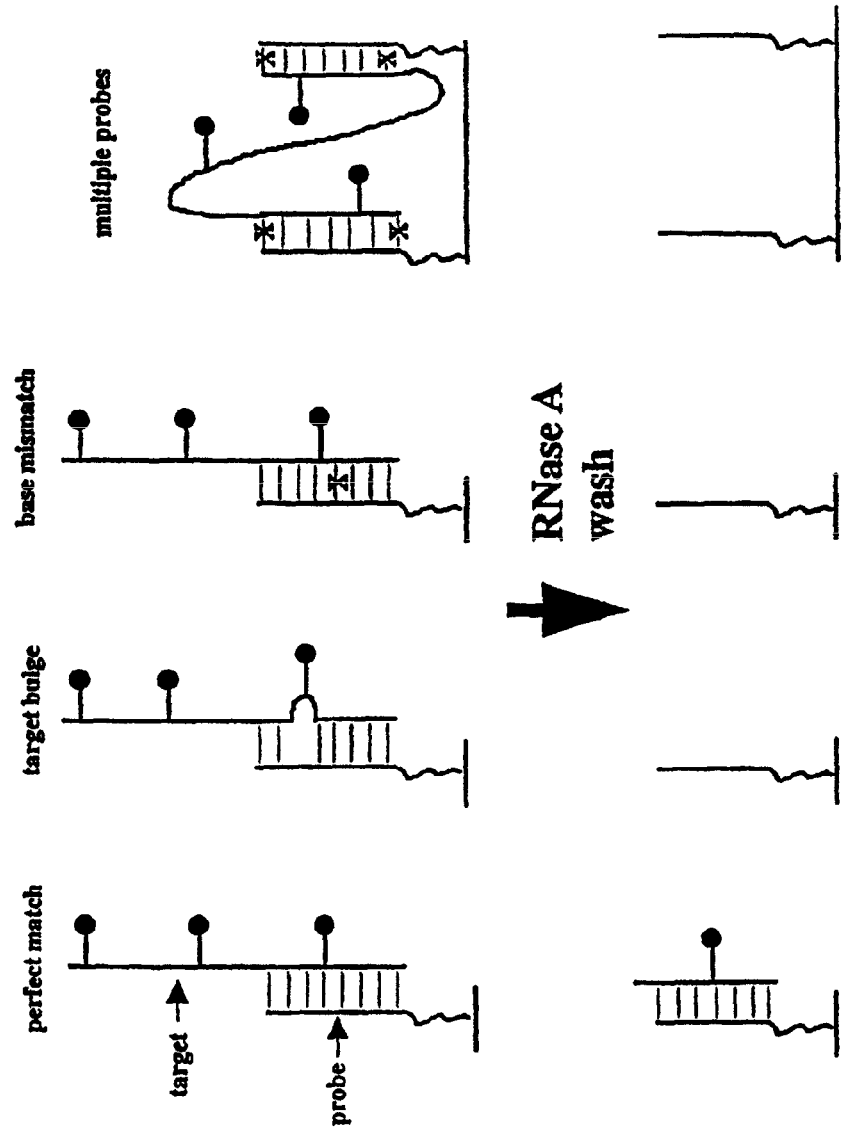
FIG. 1 illustrates discrimination of non-perfectly complementary target:oligonucleotide hybrids using RNase A.

I. Glossary
II. General Overview
III. Methods For Generating An Array Of Oligonucleotides On A Substrate
IV. Sequencing By Hybridization Using the Probe Tiling Strategy
V. Enzymatic Discrimination Enhancement
VI. Detection Methods
VII. Applications VIII. Libraries of Unimolecular, Double-Stranded Oligonucleotides
IX. Libraries of Conformationally Restricted Probes
X. Libraries of Intermolecular, Doubly-Anchored, Double-Stranded Oligonucleotides
XI. Methods of Library Screening
XII. Bioelectric Devices and Methods
XIII. Alternative Embodiments
XIV. Examples
XV. Conclusion

I. GLOSSARY

The following terms are intended to have the following general meanings as they are used herein:

1. Substrate: A material having a rigid or semi-rigid surface. In many embodiments, at least one surface of the substrate will be substantially flat, although in some embodiments it may be desirable to physically separate synthesis regions for different polymers with, for example, wells, raised regions, etched trenches, or the like. In some embodiments, the substrate itself contains wells, trenches, flow through regions, etc. which form all or part of the synthesis regions. According to other embodiments, small beads may be provided on the surface, and compounds synthesized thereon may be released upon completion of the synthesis.

2. Predefined Region: A predefined region is a localized area on a substrate which is, was, or is intended to be used for formation of a selected polymer and is otherwise referred to herein in the alternative as "reaction" region, a "selected" region, or simply a "region." The predefined region may have any convenient shape, e.g., circular, rectangular, elliptical, wedge-shaped, etc. In some embodiments, a predefined region and, therefore, the area upon which each distinct polymer sequence is synthesized is smaller than about 1 cm$^2$, more preferably less than 1 mm$^2$, and still more preferably less than 0.5 mm$^2$. In most preferred embodiments, the regions have an area less than about 10,000 $\mu$m$^2$ or, more preferably, less than 100 $\mu$m$^2$. Within these regions, the polymer synthesized therein is preferably synthesized in a substantially pure form.

3. Substantially Pure: A polymer or other compound is considered to be "substantially pure" when it exhibits characteristics that distinguish it from the polymers or compounds in other regions. For example, purity can be measured in terms of the activity or concentration of the compound of interest. Preferably the compound in a region is sufficiently pure such that it is the predominant species in the region. According to certain aspects of the invention, the compound is 5% pure, more preferably more than 10% pure, and most preferably more than 20% pure. According to more preferred aspects of the invention, the compound is greater man 80% pure, preferably more than 90% pure, and more preferably more than 95% pure, where purity for this purpose refers to the ratio of the number of compound molecules formed in a region having a desired structure to the total number of non-solvent molecules in the region.

4. Monomer: In general, a monomer is any member of the set of molecules which can be joined together to form an oligomer or polymer. The set of monomers useful in the present invention includes, but is not restricted to, for the example of oligonucleotide synthesis, the set of nucleotides consisting of adenine, thymine, cytosine, guanine, and uridine (A, T, C, G, and U, respectively) and synthetic analogs thereof. As used herein, monomers refers to any member of a basis set for synthesis of an oligomer. Different basis sets of monomers may be used at successive steps in the synthesis of a polymer.

5. Oligomer or Polymer: The oligomer or polymer sequences of the present invention are formed from the chemical or enzymatic addition of monomer subunits. Such oligomers include, for example, both linear, cyclic, and branched polymers of nucleic acids, polysaccharides, phospholipids, and peptides having either $\alpha$-, $\beta$-, or $\omega$-amino acids, heteropolymers in which a known drug is covalently bound to any of the above, polyurethanes, polyesters, polycarbonates, polyureas, polyamides, polyethyleneimines, polyarylene sulfides, polysiloxanes, polyimides, polyacetates, or other polymers which will be readily apparent to one skilled in the art upon review of this disclosure. As used herein, the term oligomer or polymer is meant to include such molecules as $\beta$-turn mimetics, prostaglandins and benzodiazepines which can also be synthesized in a step-wise fashion on a solid support.

6. Peptide: A peptide is an oligomer in which the monomers are amino acids and which are joined together through amide bonds and alternatively referred to as a polypeptide. In the context of this specification it should be appreciated that when $\alpha$-amino acids are used, they may be the L-optical isomer or the D-optical isomer. Other amino acids which are useful in the present invention include unnatural amino acids such as $\beta$-alanine, phenylglycine, homoarginine and the like. Peptides are more than two amino acid monomers long, and often more than 20 amino acid monomers long. Standard abbreviations for amino acids are used (e.g., P for proline). These abbreviations are included in Stryer, *Biochemistry*, Third Ed., (1988), which is incorporated herein by reference for all purposes.

7. Oligonucleotides: An oligonucleotide is a single-stranded DNA or RNA molecule, typically prepared by synthetic means. Alternatively, naturally occurring oligonucleotides, or fragments thereof, may be isolated from their natural sources or purchased from commercial sources. Those oligonucleotides employed in the present invention will be 4 to 100 nucleotides in length, preferably from 6 to 30 nucleotides, although oligonucleotides of different length may be appropriate. Suitable oligonucleotides may be prepared by the phosphoramidite method described by Beaucage and Carruthers, *Tetrahedron Lett.*, 22:1859-1862 (1981), or by the triester method according to Matteucci, et al., *J. Am. Chem. Soc.*, 103:3185 (1981), both incorporated herein by reference, or by other chemical methods using either a commercial automated oligonucleotide synthesizer or VLSIPS™ technology (discussed in detail below). When oligonucleotides are referred to as "double-stranded," it is understood by those of skill in the art that a pair of oligonucleotides exist in a hydrogen-bonded, helical array typically associated with, for example, DNA. In addition to the 100% complementary form of double-stranded oligonucleotides, the term "double-stranded" as used herein is also meant to refer to those forms which include such structural features as bulges and loops, described more fully in such biochemistry texts as Stryer, *Biochemistry*, Third Ed., (1988), previously incorporated herein by reference for all purposes.

8. Chemical terms: As used herein, the term "alkyl" refers to a saturated hydrocarbon radical which may be straight-chain or branched-chain (for example, ethyl, isopropyl, f-amyl, or 2,5-dimethylhexyl). When "alkyl" or "alkylene" is used to refer to a linking group or a spacer, it is taken to be a group having two available valences for covalent attachment, for example, —CH$_2$CH$_2$—, —CH$_2$CH$_2$CH$_2$—, —CH$_2$CH$_2$CH(CH$_3$)CH$_2$— and —CH$_2$(CH$_2$CH$_2$)$_2$CH$_2$—. Preferred alkyl groups as substituents are those containing 1 to 10 carbon atoms, with those containing 1 to 6 carbon atoms being particularly preferred. Preferred alkyl or alkylene groups as linking groups are those containing 1 to 20 carbon atoms, with those containing 3 to 6 carbon atoms being particularly preferred. The term "polyethylene glycol" is used to refer to those molecules which have repeating units of ethylene glycol, for example, hexaethylene glycol (HO—$(CH_2CH_2O)_5$—$CH_2CH_2OH$). When the term "polyethylene glycol" is used to refer to linking groups and spacer groups, it would be understood by one of skill in the art that other polyethers or polyols could be used as well (i.e, polypropylene glycol or mixtures of ethylene and propylene glycols). The following abbreviations are used herein: phi, phenanthrenequinone diimine; phen', 5-amido-glutaric acid-1,10-phenanthroline; dppz, dipyridophenazine.

9. Protective Group: As used herein, the term "protecting group" refers to any of the groups which are designed to block one reactive site in a molecule while a chemical reaction is carried out at another reactive site. More particularly, the protecting groups used herein can be any of those groups described in Greene, et al., *Protective Groups In Organic Chemistry,* 2nd Ed., John Wiley & Sons, New York, N.Y., 1991, incorporated herein by reference. The proper selection of protecting groups for a particular synthesis will be governed by the overall methods employed in the synthesis. For example, in "light-directed" synthesis, discussed below, the protecting groups will be photolabile protecting groups such as NVOC, MeNPOC, and those disclosed in co-pending Application PCT/US93/10162 (filed Oct. 22, 1993), incorporated herein by reference. In other methods, protecting groups may be removed by chemical methods and include groups such as FMOC, DMT and others known to those of skill in the art.

10. Complementary or substantially complementary: Refers to the hybridization or base pairing between nucleotides or nucleic acids, such as, for instance, between the two strands of a double stranded DNA molecule, or between an oligonucleotide primer and a primer binding site on a single stranded nucleic acid to be sequenced or amplified. Complementary nucleotides are, generally, A and T (or A and U), or C and G. Two single stranded RNA or DNA molecules are said to be substantially complementary when the nucleotides of one strand, optimally aligned and compared and with appropriate nucleotide insertions or deletions, pair with at least about 80% of the nucleotides of the other strand, usually at least about 90% to 95%, and more preferably from about 98 to 100%. Alternatively, substantial complementarity exists when an RNA or DNA strand will hybridize under selective hybridization conditions to its complement. Typically, selective hybridization will occur when there is at least about 65% complementarity over a stretch of at least 14 to 25 nucleotides, preferably at least about 75%, more preferably at least about 90% complementarity. See, M. Kanehisa *Nucleic Acids Res.* 12:203 (1984), incorporated herein by reference.

11. Stringent hybridization conditions: Such conditions will typically include salt concentrations of less than about 1 M, more usually less than about 500 mM, and preferably less than about 200 mM. Hybridization temperatures can be as low as 5° C., but are typically greater than 22° C., more typically greater than about 30° C., and preferably in excess of about 37° C. Longer fragments may require higher hybridization temperatures for specific hybridization. As other factors may dramatically affect the stringency of hybridization, including base composition, length of the complementary strands, presence of organic solvents and extent of base mismatching, the combination of parameters is more important than the absolute measure of any one alone.

12. Epitope: The portion of an antigen molecule which is delineated by the area of interaction with the subclass of receptors known as antibodies.

13. Identifier tag: A means whereby one can identify which molecules have experienced a particular reaction in the synthesis of an oligomer. The identifier tag also records the step in the synthesis series in which the molecules experienced that particular monomer reaction. The identifier tag may be any recognizable feature which is, for example: microscopically distinguishable in shape, size, color, optical density, etc.; differently absorbing or emitting of light; chemically reactive; magnetically or electronically encoded; or in some other way distinctively marked with the required information. A preferred example of such an identifier tag is an oligonucleotide sequence.

14. Ligand/Probe: A ligand is a molecule that is recognized by a particular receptor. The agent bound by or reacting with a receptor is called a "ligand," a term which is definitionally meaningful only in terms of its counterpart receptor. The term "ligand" does not imply any particular molecular size or other structural or compositional feature other than that the substance in question is capable of binding or otherwise interacting with the receptor. Also, a ligand may serve either as the natural ligand to which the receptor binds, or as a functional analogue that may act as an agonist or antagonist. Examples of ligands that can be investigated by this invention include, but are not restricted to, agonists and antagonists for cell membrane receptors, toxins and venoms, viral epitopes, hormones (e.g., opiates, steroids, etc.), hormone receptors, peptides, enzymes, enzyme substrates, substrate analogs, transition state analogs, cofactors, drugs, proteins, and antibodies. The term "probe" refers to those molecules which are expected to act like ligands but for which binding information is typically unknown. For example, if a receptor is known to bind a ligand which is a peptide β-turn, a "probe" or library of probes will be those molecules designed to mimic the peptide β-turn. In instances where the particular ligand associated with a given receptor is unknown, the term probe refers to those molecules designed as potential ligands for the receptor.

15. Receptor: A molecule that has an affinity for a given ligand or probe. Receptors may be naturally-occurring or manmade molecules. Also, they can be employed in their unaltered natural or isolated state or as aggregates with other species. Receptors may be attached, covalently or noncovalently, to a binding member, either directly or via a specific binding substance. Examples of receptors which can be employed by this invention include, but are not restricted to, antibodies, cell membrane receptors, monoclonal antibodies and antisera reactive with specific antigenic determinants (such as on viruses, cells or other materials), drugs, polynucleotides, nucleic acids, peptides, cofactors, lectins, sugars, polysaccharides, cells, cellular membranes, and organelles. Receptors are sometimes referred to in the art as anti-ligands. As the term receptors is used herein, no difference in meaning is intended. A "ligand-receptor pair" is formed when two molecules have combined through molecular recognition to form a complex. Other examples of receptors which can be investigated by this invention include but are not restricted to:

a) Microorganism receptors: Determination of ligands or probes that bind to receptors, such as specific transport proteins or enzymes essential to survival of microorganisms, is useful in a new class of antibiotics. Of particular value would be antibiotics against opportunistic fungi, protozoa, and those bacteria resistant to the antibiotics in current use.

b) Enzymes: For instance, the binding site of enzymes such as the enzymes responsible for cleaving neurotransmitters. Determination of ligands or probes that bind to certain receptors, and thus modulate the action of the enzymes that cleave the different neurotransmitters, is useful in the development of drugs that can be used in the treatment of disorders of neurotransmission.

c) Antibodies: For instance, the invention may be useful in investigating the ligand-binding site on the antibody molecule which combines with the epitope of an antigen of interest. Determining a sequence that mimics an antigenic epitope may lead to the development of vaccines of which the immunogen is based on one or more of such sequences, or lead to the development of related diagnostic agents or compounds useful in therapeutic treatments such as for autoimmune diseases (e.g., by blocking the binding of the "self" antibodies).

d) Nucleic Acids: The invention may be useful in investigating sequences of nucleic acids acting as binding sites for cellular proteins ("trans-acting factors"). Such sequences may include, e.g., transcription factors, suppressors, enhancers or promoter sequences.

e) Catalytic Polypeptides: Polymers, preferably polypeptides, which are capable of promoting a chemical reaction involving the conversion of one or more reactants to one or more products. Such polypeptides generally include a binding site specific for at least one reactant or reaction intermediate and an active functionality proximate to the binding site, which functionality is capable of chemically modifying the bound reactant. Catalytic polypeptides are described in, Lerner, R. A. et al., *Science* 252:659 (1991), which is incorporated herein by reference.

f) Hormone receptors: For instance, the receptors for insulin and growth hormone. Determination of the ligands which bind with high affinity to a receptor is useful in the development of, for example, an oral replacement of the daily injections which diabetics must take to relieve the symptoms of diabetes, and in the other case, a replacement for the scarce human growth hormone that can only be obtained from cadavers or by recombinant DNA technology. Other examples are the vasoconstrictive hormone receptors; determination of those ligands that bind to a receptor may lead to the development of drugs to control blood pressure.

g) Opiate receptors: Determination of ligands that bind to the opiate receptors in the brain is useful in the development of less-addictive replacements for morphine and related drugs.

16. Synthetic: Produced by in vitro chemical or enzymatic synthesis. The synthetic libraries of the present invention may be contrasted with those in viral or plasmid vectors, for instance, which may be propagated in bacterial, yeast, or other living hosts.

17. Probe: A molecule of known composition or monomer sequence, typically formed on a solid surface, which is or may be exposed to a target molecule and examined to determine if the probe has hybridized to the target. Also referred to herein as an "oligonucleotide" or an "oligonucleotide probe."

18. Target: A molecule, typically of unknown composition or monomer sequence, for which it is desired to study the composition or monomer sequence. A target may be a part of a larger molecule, such as a few bases in a longer nucleic acid.

19. A, T, C, G, U: A, T, C, G, and U are abbreviations for the nucleotides adenine, thymine, cytosine, guanine, and uridine, respectively.

20. Array or Chip or Library: A collection of oligonucleotide probes of predefined nucleotide sequence, often formed in one or more substrates, which are used in hybridization studies of target nucleic acids.

II. GENERAL OVERVIEW

In one embodiment, the present invention provides improved methods for obtaining sequence information about nucleic acids (i.e., oligonucleotides). More particularly, the present invention provides improved methods for discriminating between fully complementary hybrids and those that differ by one or more base pairs. The methods of the present invention rely, in part, on the ability to synthesize or attach specific oligonucleotides at known locations on a substrate, typically a single substrate. Such oligonucleotides are capable of interacting with specific target nucleic acid while attached to the substrate. By appropriate labeling of these targets, the sites of the interactions between the target and the specific oligonucleotide can be derived. Moreover, because the oligonucleotides are positionally defined, the target sequence can be reconstructed from the sites of the interactions.

It has now been determined that reconstruction of the target sequence can be improved by using various enzymes that catalyze oligonucleotide cleavage and ligation reactions. More particularly, it has been determined that discrimination between fully complementary hybrids and those that differ by one or more base pairs can be greatly enhanced by using various enzymes that catalyze oligonucleotide cleavage and ligation reactions.

RNase A treatment, for example, can be used to improve the quality of RNA hybridization signals on high density oligonucleotide arrays. After the array of oligonucleotides has been combined with a target nucleic acid (RNA) to form target-oligonucleotide hybrid complexes, the target-oligonucleotide hybrid complexes are treated with RNase A to remove non-perfectly complementary target-oligonucleotide hybrid complexes, RNase A recognizes and cuts single-stranded RNA, including RNA in RNA:DNA hybrids that is not in a perfect double-stranded structure. As illustrated in FIG. 1, RNA bulges, loops, and even single base mismatches can be recognized and cleaved by RNase A. Similarly, treatment with other nucleases (e.g., S1 nuclease and Mung Bean nuclease) can be used to improve the DNA hybridization signals on high density oligonucleotide arrays. As such, nuclease treatment can be used to improve the quality of hybridization signals on high density oligonucleotide arrays and, in turn, to more accurately determine the sequence, or monitor mutations, or resequence the target nucleic acid.

Figure 2:
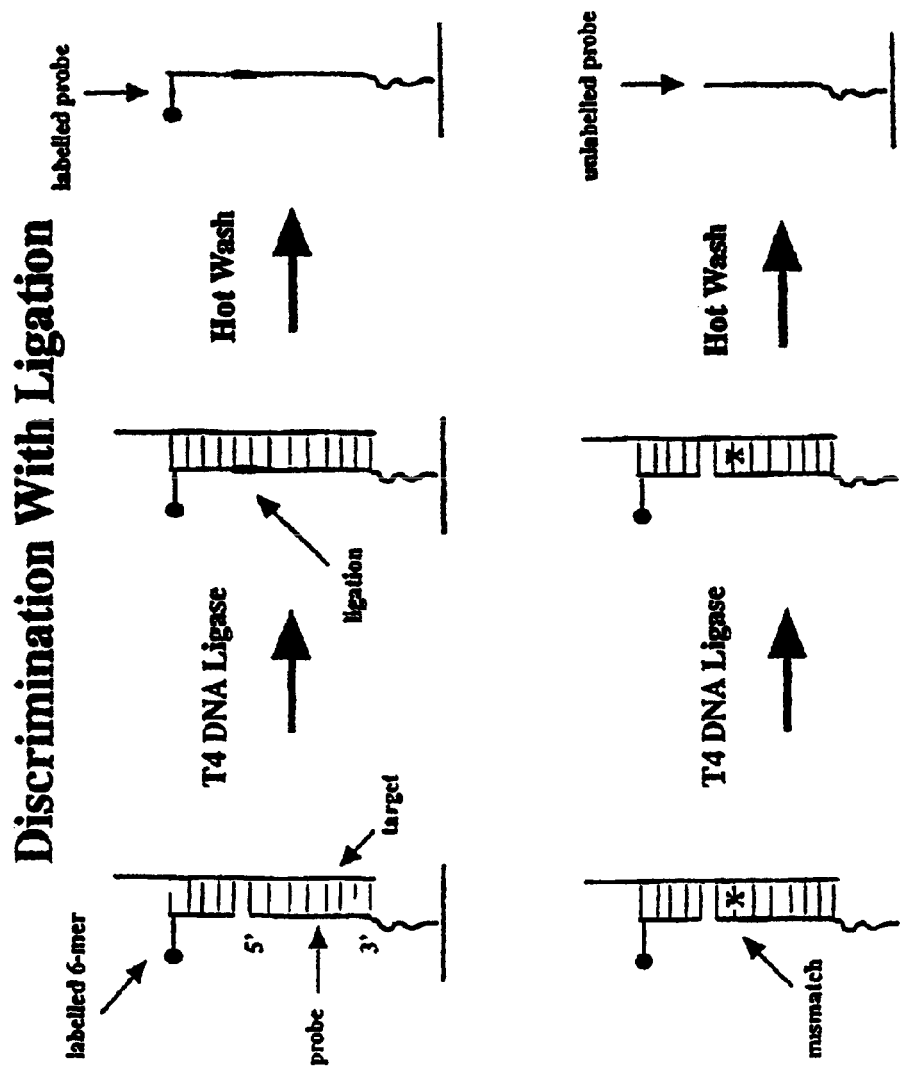
FIG. 2 illustrates discrimination of non-perfectly complementary target:oligonucleotide hybrids using a ligation reaction.
Figure 3:
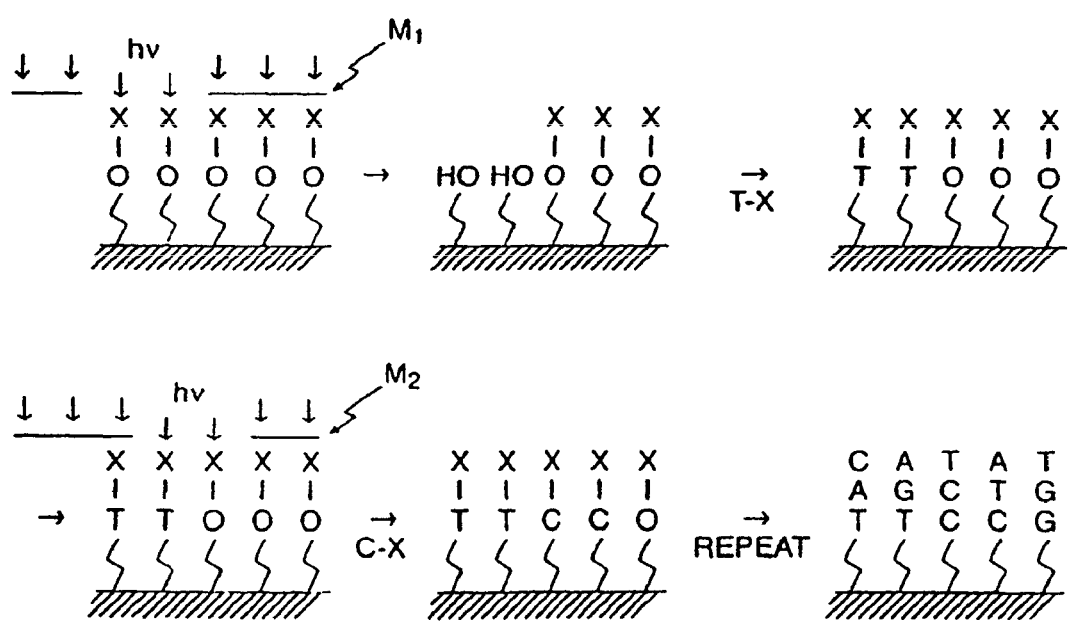
FIG. 3 illustrates the light directed synthesis of an array of oligonucleotides on a substrate.

Moreover, ligation reactions can be used to discriminate between fully complementary hybrids and those that differ by one or more base pairs. T4 DNA ligase, for example, can be used to identify DNA:DNA hybrids that are perfectly complementary near the 5' end of the immobilized oligonucleotide probes. The ligation reaction of labelled, short oligonucleotides to the 5' end of oligonucleotide probes on a substrate will occur, in the presence of a ligase, only when a target: oligonucleotide hybrid has formed with correct base-pairing near the 5' end of the oligonucleotide probe and where there is a suitable 3' overhang of the target to serve as a template for hybridization and ligation. As such, after the array of oligonucleotides has been combined with a target nucleic acid to form target-oligonucleotide hybrid complexes, the target-oligonucleotide hybrid complexes can be contacted with a ligase and a labelled, ligatable oligonucleotide probe. After the ligation reaction, the substrate is washed to remove the target nucleic acid and labelled, unligated oligonucleotide probes. The oligonucleotide probes containing the label indicate sequences which are perfectly complementary to target nucleic acid sequence. As such, as illustrated in FIG. 2, ligation reactions can be used to improve discrimination of base-pair mismatches near the 5' end of the probe, mismatches that are often poorly discriminated following hybridization alone.

Figure 9A:
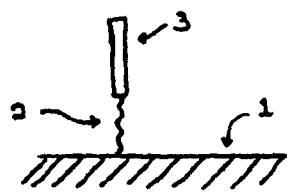
FIG. 9A to 9F illustrate the preparation of a member of a library of surface-bound, unimolecular double-stranded DNA as well as binding studies with receptors having specificity for either the double stranded DNA portion, a probe which is held in a conformationally restricted form by DNA scaffolding, or a bulge or loop region of RNA.
Figure 9B:
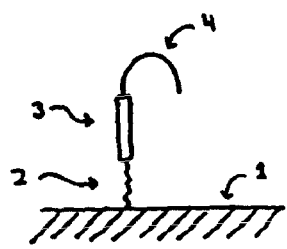
Figure 9C:
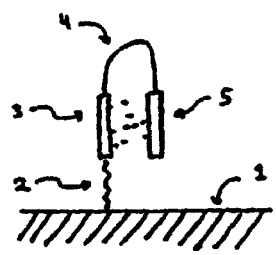

In addition to providing improved methods for discriminating between fully complementary hybrids and those that differ by one or more base pairs, the present invention provides methods for the preparation of high-density arrays of diverse unimolecular and intramolecular double-stranded oligonucleotides, as well as arrays of conformationally restricted probes. The broad concept of such arrays is illustrated in FIG. 9. FIGS. 9A, 9B and 9C illustrate the preparation of surface-bound unimolecular double stranded DNA, while FIGS. 9D, 9E and 9F illustrate uses for the libraries of the present invention.

FIG. 9A shows a solid support 1 having an attached spacer 2, which is optional. Attached to the distal end of the spacer is a first oligomer 3, which can be attached as a single unit or synthesized on the support or spacer in a monomer by monomer approach. FIG. 9B shows a subsequent stage in the preparation of one member of a library according to the present invention. In this stage, a flexible linker 4 is attached to the distal end of the oligomer 3. In other embodiments, the flexible linker will be a probe. FIG. 9C shows the completed surface-bound unimolecular double stranded DNA which is one member of a library, wherein a second oligomer 5 is now attached to the distal end of the flexible linker (or probe). As shown in FIG. 9C, the length of the flexible linker (or probe) 4 is sufficient such that the first and second oligomers (which are complementary) exist in a double-stranded conformation. It will be appreciated by one of skill in the art, that the libraries of the present invention will contain multiple, individually synthesized members which can be screened for various types of activity. Three such binding events are illustrated in FIGS. 9D, 9E and 9F.

Figure 9D:
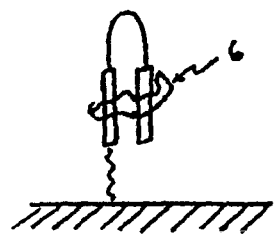

In FIG. 9D, a receptor 6, which can be a protein, RNA molecule or other molecule which is known to bind to DNA, is introduced to the library. Determining which member of a library binds to the receptor provides information which is useful for diagnosing diseases, sequencing DNA or RNA, identifying drugs and/or proteins that bind DNA, identifying genetic characteristics, or in other drug discovery endeavors.

Figure 9E:
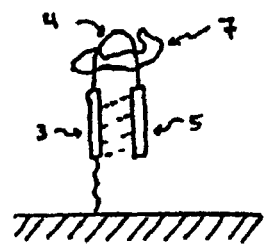
Figure 9F:
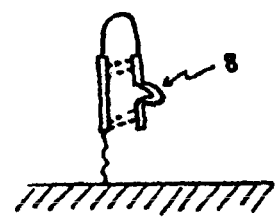

In FIG. 9E, the linker 4 is a probe for which binding information is sought. The probe is held in a conformationally restricted manner by the flanking oligomers 3 and 5, which are present in a double-stranded conformation. As a result, a library of conformationally restricted probes can be screened for binding activity with a receptor 7 which has specificity for the probe.

The present invention also contemplates the preparation of libraries of unimolecular, double-stranded oligonucleotides having bulges or loops in one of the strands as depicted in FIG. 9F. In FIG. 9F, one oligonucleotide 5 is shown as having a bulge 8. Specific RNA bulges are often recognized by proteins (e.g., TAR RNA is recognized by the TAT protein of HIV). Accordingly, libraries of RNA bulges or loops are useful in a number of diagnostic applications. One of skill in the art will appreciate that the bulge or loop can be present in either oligonucleotide portion 3 or 5.

Figure 10A:
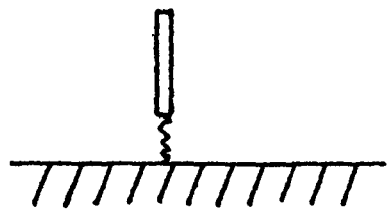
FIG. 10A to 10G illustrate the preparation of several different types of intermolecular, doubly-anchored, double-stranded oligonucleotides.
Figure 10E:
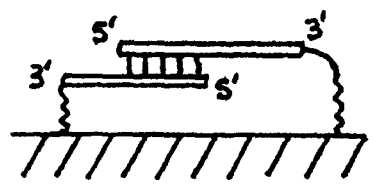
Figure 10B:
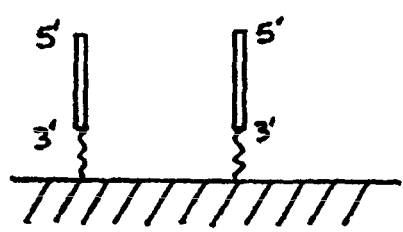
Figure 10F:
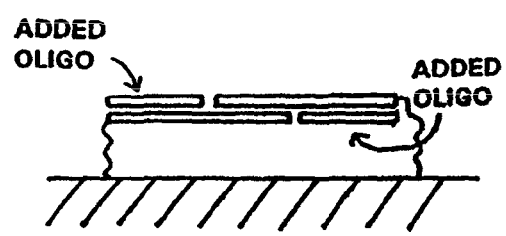
Figure 10C:
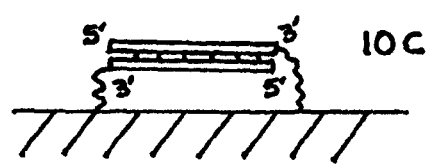
Figure 10G:
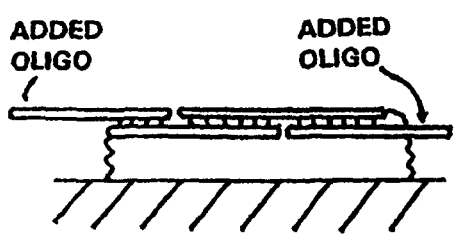
Figure 10D:

In another embodiment, the present invention provides libraries of intermolecular, doubly-anchored, double-stranded oligonucleotides. The broad concept of this aspect of the invention is illustrated in FIG. 10. As with the above described "unimolecular" aspect of the invention, FIG. 10A shows a solid support 11 having an attached spacer 12, which is optional. Attached to the distal end of the spacer is a first oligomer 13, which can be attached as a single unit or synthesized on the support or spacer in a monomer by monomer approach. FIG. 10B shows a subsequent stage in the preparation of one member of a library according to the present invention. In this stage, a second oligomer 14 which is complementary to the first oligomer 13, is attached to the solid support. The second oligomer can also be attached as a single unit or synthesized on the support or spacer in a monomer by monomer approach. Typically, the first and second oligomers are synthesized on the solid support in a protected form. Removal of the protecting groups provides a solid support with complementary oligomers in close proximity which can form a completed intermolecular, doubly-anchored, double stranded oligonucleotide (FIG. 10C). FIG. 10D shows one member of a library in which the first self-complementary oligomer is 3'-AAAAATTTTT-5' (SEQ ID NO: 3) and its identical neighboring oligomer is 3'-TTTT-TAAAAA-5' (SEQ ID NO: 4). In other embodiments of this aspect of the invention, the complementary oligomers will exhibit complementarity only over their respective termini, as shown in FIG. 10E. It will be appreciated by one of skill in the art, that the libraries of the present invention will contain multiple, individually synthesized members which can be screened for various types of activity or which can serve as templates for hybridization enhancement.

III. METHODS FOR GENERATING AN ARRAY OF OLIGONUCLEOTIDES ON A SUBSTRATE

A. The Substrate

In the methods of the present invention, an array of diverse oligonucleotides at known locations on a single substrate surface is employed. Essentially, any conceivable substrate can be employed in the invention. The substrate can be organic, inorganic, biological, nonbiological, or a combination of any of these, existing as beads, particles, strands, precipitates, gels, sheets, tubing, spheres, containers, capillaries, pads, slices, films, plates, slides, etc. The substrate can have any convenient shape, such a disc, square, sphere, circle, etc. The substrate is preferably flat, but may take on a variety of alternative surface configurations. For example, the substrate may contain raised or depressed regions on which the synthesis takes place. The substrate and its surface preferably form a rigid support on which to carry out the reaction described herein. The substrate and its surface may also chosen to provide appropriate light-absorbing characteristics. The substrate may be any of a wide variety of materials including, for example, polymers, plastics, pyrex, quartz, resins, silicon, silica or silica-based materials, carbon, metals, inorganic glasses, inorganic crystals, membranes, etc. More particularly, the substrate may, for instance, be a polymerized Langmuir Blodgett film, functionalized glass, Si, Ge GaAs, GaP, $SiO_2$, $SiN_4$, modified silicon, or any one of a wide variety of gels or polymers such as (poly)-tetrafluorotheylene, (poly)vinylidenedifluoride, polystyrene, polycarbonate, or combinations thereof. Other substrate materials will be readily apparent to those of skill in the art upon review of this disclosure. In a preferred embodiment the substrate is flat glass or single-crystal silicon with surface relief features of less than 10.

In some embodiments, a predefined region on the substrate and, therefore, the area upon which each distinct material is synthesized will have a surface area of between about 1 $cm^2$ and $10^{-10}$ $cm^2$. In some embodiments, the regions have areas of less than about $10^{-1}$ $cm^2$, $10^{-2}$ $cm^2$, $10^{-3}$ $cm^2$, $10^{-4}$ $cm^2$, $10^{-5}$ $cm^2$, $10^{-6}$ $cm^2$, $10^{-7}$ $cm^2$, $10^{-8}$ $cm^2$, or $10^{-10}$ $cm^2$. In a preferred embodiment, the regions are between about 10×10 µm and 500×100 µm.

Moreover, in some embodiments, a single substrate supports more than about 10 different monomer sequences and preferably more than about 100 different monomer sequences, although in some embodiments more than about $10^3$, $10^4$, $10^5$, $10^6$, $10^7$, or $10^8$ different sequences are provided on a substrate. Of course, within a region of the substrate in which a monomer sequence is synthesized, it is preferred that the monomer sequence be substantially pure. In some embodiments, regions of the substrate contain polymer sequences which are at least about 1%, 5%, 10%, 15%, 20%, 25%, 30%, 35%, 40%, 45%, 50%, 60%, 70%, 80% 90%, 95%, 96%, 97%, 98%, or 99% pure.

As previously explained, the substrate is preferably flat, but may take on a variety of alternative surface configurations. Regardless of the configuration of the substrate surface, it is imperative that the reactants used to generate an array of oligonucleotides in the individual reaction regions be prevented from moving to adjacent reaction regions. Most simply, this is ensured by chemically attaching the oligonucleotides to the substrate. Moreover, this can be ensured by providing an appropriate barrier between the various reaction regions on the substrate. A mechanical device or physical structure can be used to define the various regions on the substrate. For example, a wall or other physical barrier can be used to prevent the reactants in the individual reaction regions from moving to adjacent reaction regions. Alternatively, a dimple or other recess can be used to prevent the reactant components in the individual reaction regions from moving to adjacent reaction regions.

B. Generating An Array Using Light-Directed Methods

An array of diverse oligonucleotides diverse oligonucleotides at known locations on a single substrate surfaces can be formed using a variety of techniques known to those skilled in the art of polymer synthesis on solid supports. For example, "light directed" methods (which are one technique in a family of methods known as VLSIPS™ methods) are described in U.S. Pat. No. 5,143,854, previously incorporated by reference. The light directed methods discussed in the '854 patent involve activating predefined regions of a substrate or solid support and then contacting the substrate with a preselected monomer solution. The predefined regions can be activated with a light source shown through a mask (much in the manner of photolithography techniques used in integrated circuit fabrication). Other regions of the substrate remain inactive because they are blocked by the mask from illumination and remain chemically protected. Thus, a light pattern defines which regions of the substrate react with a given monomer. By repeatedly activating different sets of predefined regions and contacting different monomer solutions with the substrate, a diverse array of polymers is produced on the substrate. Of course, other steps such as washing unreacted monomer solution from the substrate can be used as necessary. Other techniques include mechanical techniques such as those described in PCT No. 92/10183, U.S. Ser. No. 07/796,243, also incorporated herein by reference for all purposes. Still further techniques include bead based techniques such as those described in PCT US/93/04145, also incorporated herein by reference, and pin based methods such as those described in U.S. Pat. No. 5,288,514, also incorporated herein by reference.

The VLSIPS™ methods are preferred for generating an array of oligonucleotides on a single substrate. The surface of the solid support or substrate can be optionally modified with spacers having photolabile protecting groups such as NVOC and MeNPOC, is illuminated through a photolithographic mask, yielding reactive groups (typically hydroxyl groups) in the illuminated regions. A 3'-O-phosphoramidite activated deoxynucleoside (protected at the 5'-hydroxyl with a photolabile protecting group) is then presented to the surface and chemical coupling occurs at sites that were exposed to light. Following capping, and oxidation, the substrate is rinsed and the surface illuminated through a second mask, to expose additional hydroxyl groups for coupling. A second 5'-protected, 3'-O-phosphoramidite activated deoxynucleoside is presented to the surface. The selective photodeprotection and coupling cycles are repeated until the desired set of oligonucleotides is produced.

C. Generating An Array Of Oligonucleotides Using Flow Channel Or Spotting Methods In addition to the foregoing, additional methods which can be used to generate an array of oligonucleotides on a single substrate are described in co-pending application Ser. No. 07/980,523, filed Nov. 20, 1992, and 07/796,243, filed Nov. 22, 1991, incorporated herein by reference for all purposes. In the methods disclosed in these applications, reagents are delivered to the substrate by either (1) flowing within a channel defined on predefined regions or (2) "spotting" on predefined regions. However, other approaches, as well as combinations of spotting and flowing, may be employed. In each instance, certain activated regions of the substrate are mechanically separated from other regions when the monomer solutions are delivered to the various reaction sites.

A typical "flow channel" method applied to the compounds and libraries of the present invention can generally be described as follows. Diverse polymer sequences are synthesized at selected regions of a substrate or solid support by forming flow channels on a surface of the substrate through which appropriate reagents flow or in which appropriate reagents are placed. For example, assume a monomer "A" is to be bound to the substrate in a first group of selected regions. If necessary, all or part of the surface of the substrate in all or a part of the selected regions is activated for binding by, for example, flowing appropriate reagents through all or some of the channels, or by washing the entire substrate with appropriate reagents. After placement of a channel block on the surface of the substrate, a reagent having the monomer A flows through or is placed in all or some of the channels). The channels provide fluid contact to the first selected regions, thereby binding the monomer A on the substrate directly or indirectly (via a spacer) in the first selected regions.

Thereafter, a monomer B is coupled to second selected regions, some of which may be included among the first selected regions. The second selected regions will be in fluid contact with a second flow channel(s) through translation, rotation, or replacement of the channel block on the surface of the substrate; through opening or closing a selected valve; or through deposition of a layer of chemical or photoresist. If necessary, a step is performed for activating at least the second regions. Thereafter, the monomer B is flowed through or placed in the second flow channel(s), binding monomer B at the second selected locations. In this particular example, the resulting sequences bound to the substrate at this stage of processing will be, for example, A, B, and AB. The process is repeated to form a vast array of sequences of desired length at known locations on the substrate.

After the substrate is activated, monomer A can be flowed through some of the channels, monomer B can be flowed through other channels, a monomer C can be flowed through still other channels, etc. In this manner, many or all of the reaction regions are reacted with a monomer before the channel block must be moved or the substrate must be washed and/or reactivated. By making use of many or all of the available reaction regions simultaneously, the number of washing and activation steps can be minimized.

One of skill in the art will recognize that there are alternative methods of forming channels or otherwise protecting a portion of the surface of the substrate. For example, according to some embodiments, a protective coating such as a hydrophilic or hydrophobic coating (depending upon the nature of the solvent) is utilized over portions of the substrate to be protected, sometimes in combination with materials that facilitate wetting by the reactant solution in other regions. In this manner, the flowing solutions are further prevented from passing outside of their designated flow paths.

The "spotting" methods of preparing compounds and libraries of the present invention can be implemented in much the same manner as the flow channel methods. For example, a monomer A can be delivered to and coupled with a first group of reaction regions which have been appropriately activated. Thereafter, a monomer B can be delivered to and reacted with a second group of activated reaction regions. Unlike the flow channel embodiments described above, reactants are delivered by directly depositing (rather than flowing) relatively small quantities of them in selected regions. In some steps, of course, the entire substrate surface can be sprayed or otherwise coated with a solution. In preferred embodiments, a dispenser moves from region to region, depositing only as much monomer as necessary at each stop. Typical dispensers include a micropipette to deliver the monomer solution to the substrate and a robotic system to control the position of the micropipette with respect to the substrate. In other embodiments, the dispenser includes a series of tubes, a manifold, an array of pipettes, or the like so that various reagents can be delivered to the reaction regions simultaneously.

D. Generating An Array Of Oligonucleotides Using Pin-Based Methods

Another method which is useful for the preparation of an array of diverse oligonucleotides on a single substrate involves "pin based synthesis." This method is described in detail in U.S. Pat. No. 5,288,514, previously incorporated herein by reference. The method utilizes a substrate having a plurality of pins or other extensions. The pins are each inserted simultaneously into individual reagent containers in a tray. In a common embodiment, an array of 96 pins/containers is utilized.

Each tray is filled with a particular reagent for coupling in a particular chemical reaction on an individual pin. Accordingly, the trays will often contain different reagents. Since the chemistry used is such that relatively similar reaction conditions may be utilized to perform each of the reactions, multiple chemical coupling steps can be conducted simultaneously. In the first step of the process, a substrate on which the chemical coupling steps are conducted is provided. The substrate is optionally provided with a spacer having active sites. In the particular case of oligonucleotides, for example, the spacer may be selected from a wide variety of molecules which can be used in organic environments associated with synthesis as well as in aqueous environments associated with binding studies. Examples of suitable spacers are polyethyleneglycols, dicarboxylic acids, polyamines and alkylenes, substituted with, for example, methoxy and ethoxy groups. Additionally, the spacers will have an active site on the distal end. The active sites are optionally protected initially by protecting groups. Among a wide variety of protecting groups which are useful are FMOC, BOC, t-butyl esters, t-butyl ethers, and the like. Various exemplary protecting groups are described in, for example, Atherton et al., *Solid Phase Peptide Synthesis*, IRL Press (1989), incorporated herein by reference. In some embodiments, the spacer may provide for a cleavable function by way of, for example, exposure to acid or base.

E. Generating An Array Of Oligonucleotides Using Bead Based Methods

In addition to the foregoing methods, another method which is useful for synthesis of an array of oligonucleotides involves "bead based synthesis." A general approach for bead based synthesis is described in copending application Ser. Nos. 07/762,522 (filed Sep. 18, 1991); 07/946,239 (filed Sep. 16, 1992); 08/146,886 (filed Nov. 2, 1993); 07/876,792 (filed Apr. 29, 1992) and PCT/US93/04145 (filed Apr. 28, 1993), the disclosures of which are incorporated herein by reference.

For the synthesis of molecules such as oligonucleotides on beads, a large plurality of beads are suspended in a suitable carrier (such as water) in a container. The beads are provided with optional spacer molecules having an active site. The active site is protected by an optional protecting group.

In a first step of the synthesis, the beads are divided for coupling into a plurality of containers. For the purposes of this brief description, the number of containers will be limited to three, and the monomers denoted as A, B, C, D, E, and F. The protecting groups are then removed and a first portion of the molecule to be synthesized is added to each of the three containers (i.e., A is added to container 1, B is added to container 2 and C is added to container 3).

Thereafter, the various beads are appropriately washed of excess reagents, and remixed in one container. Again, it will be recognized that by virtue of the large number of beads utilized at the outset, there will similarly be a large number of beads randomly dispersed in the container, each having a particular first portion of the monomer to be synthesized on a surface thereof.

Thereafter, the various beads are again divided for coupling in another group of three containers. The beads in the first container are deprotected and exposed to a second monomer (D), while the beads in the second and third containers are coupled to molecule portions E and F, respectively. Accordingly, molecules AD, BD, and CD will be present in the first container, while AE, BE, and CE will be present in the second container, and molecules AF, BF, and CF will be present in the third container. Each bead, however, will have only a single type of molecule on its surface. Thus, all of the possible molecules formed from the first portions A, B, C, and the second portions D, E, and F have been formed.

The beads are then recombined into one container and additional steps are conducted to complete the synthesis of the polymer molecules. In a preferred embodiment, the beads are tagged with an identifying tag which is unique to the particular oligonucleotide which is present on each bead. A complete description of identifier tags for use in synthetic libraries is provided in co-pending application Ser. No. 08/146,886 (filed Nov. 2, 1993), previously incorporated by reference for all purposes.

IV. SEQUENCING BY HYBRIDIZATION USING THE PROBE TILING STRATEGY

Using the VLSIPS™ technology described above, one can generate arrays of immobilized probes which can be used to compare a reference sequence of known sequence with a target sequence showing substantial similarity with the reference sequence, but differing in the presence of, for example, mutations. In fact, WO 95/11995, the teachings of which are incorporated herein by reference, describes a number of strategies for comparing a polynucleotide of known sequence (a reference sequence) with variants of that sequence (target sequences). The comparison can be performed at the level of entire genomes, chromosomes, genes, exons or introns, or it can focus on individual mutant sites and immediately adjacent bases. The strategies allow detection of variations, such as mutations or polymorphisms, in the target sequence irrespective of whether a particular variant has previously been characterized. The strategies both define the nature of a variant and identify its location in a target sequence.

The strategies employ arrays of oligonucleotide probes immobilized to a solid support. Target sequences are analyzed by determining the extent of hybridization at particular probes in the array. The strategy in selection of probes facilitates distinction between perfectly matched probes and probes showing single-base or other degrees of mismatches. The strategy usually entails sampling each nucleotide of interest in a target sequence several times, thereby achieving a high degree of confidence in its identity. This level of confidence is further increased by sampling of adjacent nucleotides in the target sequence to nucleotides of interest The tiling strategies disclosed in WO 95/11995 result in sequencing and comparison methods suitable for routine large-scale practice with a high degree of confidence in the sequence output.

A. Selection of Reference Sequence

The arrays are designed to contain probes exhibiting complementarity to one or more selected reference sequence whose sequence is known. The arrays are used to read a target sequence comprising either the reference sequence itself or variants of that sequence. Target sequences may differ from the reference sequence at one or more positions but show a high overall degree of sequence identity with the reference sequence (e.g., at least 75, 90, 95, 99, 99.9 or 99.99%). Any polynucleotide of known sequence can be selected as a reference sequence. Reference sequences of interest include sequences known to include mutations or polymorphisms associated with phenotypic changes having clinical significance in human patients. For example, the CFTR gene and P53 gene in humans have been identified as the location of several mutations resulting in cystic fibrosis or cancer respectively. Other reference sequences of interest include those that serve to identify pathogenic microorganisms and/or are the site of mutations by which such microorganisms acquire drug resistance (e.g., the HIV reverse transcriptase gene). Other reference sequences of interest include regions where polymorphic variations are known to occur (e.g., the D-loop region of mitochondrial DNA). These reference sequences have utility for, e.g., forensic or epidemiological studies. Other reference sequences of interest include p34 (related to p53), p65 (implicated in breast, prostate and liver cancer), and DNA segments encoding cytochromes P450 and other biotransformation genes (see Meyer et al., *Pharmac. Ther.* 46, 349-355 (1990)). Other reference sequences of interest include those from the genome of pathogenic viruses (e.g., hepatitis (A, B, or C), herpes virus (e.g., VZV, HSV-1, HAV-6, HSV-II, and CMV, Epstein Barr virus), adenovirus, influenza virus, flaviviruses, echovirus, rhinovirus, coxsackie virus, cornovirus, respiratory syncytial virus, mumps virus, rotavirus, measles virus, rubella virus, parvovirus, vaccinia virus, HTLV virus, dengue virus, papillomavirus, molluscum virus, poliovirus, rabies virus, JC virus and arboviral encephalitis virus. Other exemplary reference sequences which can be analyzed using the tiling strategy are disclosed in WO 95/11995.

The length of a reference sequence can vary widely from a full-length genome, to an individual chromosome, episome, gene, component of a gene, such as an exon, intron or regulatory sequences, to a few nucleotides. A reference sequence of between about 2, 5, 10, 20, 50, 100, 5000, 1000, 5,000 or 10,000, 20,000 or 100,000 nucleotides is common. Sometimes only particular regions of a sequence (e.g., exons of a gene) are of interest. In such situations, the particular regions can be considered as separate reference sequences or can be considered as components of a single reference sequence, as matter of arbitrary choice.

A reference sequence can be any naturally occurring, mutant, consensus or purely hypothetical sequence of nucleotides, RNA or DNA. For example, sequences can be obtained from computer data bases, publications or can be determined or conceived de novo. Usually, a reference sequence is selected to show a high degree of sequence identity to envisaged target sequences. Often, particularly, where a significant degree of divergence is anticipated between target sequences, more than one reference sequence is selected. Combinations of wildtype and mutant reference sequences are employed in several applications of the tiling strategy.

B. Array Design

1. Basic Tiling Strategy

The basic tiling strategy provides an array of immobilized probes for analysis of target sequences showing a high degree of sequence identity to one or more selected reference sequences. The strategy is first illustrated for an array that is subdivided into four probe sets, although it will be apparent that in some situations, satisfactory results are obtained from only two probe sets. A first probe set comprises a plurality of probes exhibiting perfect complementarity with a selected reference sequence. The perfect complementarity usually exists throughout the length of the probe. However, probes having a segment or segments of perfect complementarity that is/are flanked by leading or trailing sequences lacking complementarity to the reference sequence can also be used. Within a segment of complementarity, each probe in the first probe set has at least one interrogation position that corresponds to a nucleotide in the reference sequence. That is, the interrogation position is aligned with the corresponding nucleotide in the reference sequence, when the probe and reference sequence are aligned to maximize complementarity between the two. If a probe has more than one interrogation position, each corresponds with a respective nucleotide in the reference sequence. The identity of an interrogation position and corresponding nucleotide in a particular probe in the first probe set cannot be determined simply by inspection of the probe in the first set. As will become apparent, an interrogation position and corresponding nucleotide is defined by the comparative structures of probes in the first probe set and corresponding probes from additional probe sets.

In principle, a probe could have an interrogation position at each position in the segment complementary to the reference sequence. Sometimes, interrogation positions provide more accurate data when located away from the ends of a segment of complementarity. Thus, typically a probe having a segment of complementarity of length x does not contain more than x−2 interrogation positions. Since probes are typically 9-21 nucleotides, and usually all of a probe is complementary, a probe typically has 1-19 interrogation positions. Often the probes contain a single interrogation position, at or near the center of probe.

For each probe in the first set, there are, for purposes of the present illustration, up to three corresponding probes from three additional probe sets. See, FIG. 11. Thus, there are four probes corresponding to each nucleotide of interest in the reference sequence. Each of the four corresponding probes has an interrogation position aligned with that nucleotide of interest. Usually, the probes from the three additional probe sets are identical to the corresponding probe from the first probe set with one exception. The exception is that at least one (and often only one) interrogation position, which occurs in the same position in each of the four corresponding probes from the four probe sets, is occupied by a different nucleotide in the four probe sets. For example, for an A nucleotide in the reference sequence, the corresponding probe from the first probe set has its interrogation position occupied by a T, and the corresponding probes from the additional three probe sets have their respective interrogation positions occupied by A, C, or G, a different nucleotide in each probe. Of course, if a probe from the first probe set comprises trailing or flanking sequences lacking complementarity to the reference sequences (see FIG. 12), these sequences need not be present in corresponding probes from the three additional sets. Likewise corresponding probes from the three additional sets can contain leading or trailing sequences outside the segment of complementarity that are not present in the corresponding probe from the first probe set. Occasionally, the probes from the additional three probe set are identical (with the exception of interrogation position(s)) to a contiguous subsequence of the full complementary segment of the corresponding probe from the first probe set. In this case, the subsequence includes the interrogation position and usually differs from the full-length probe only in the omission of one or both terminal nucleotides from the termini of a segment of complementarity. That is, if a probe from the first probe set has a segment of complementarity of length n, corresponding probes from the other sets will usually include a subsequence of the segment of at least length n−2. Thus, the subsequence is usually at least 3, 4, 7, 9, 15, 21, or 25 nucleotides long, most typically, in the range of 9-21 nucleotides. The subsequence should be sufficiently long to allow a probe to hybridize detectably more strongly to a variant of the reference sequence mutated at the interrogation position than to the reference sequence.

The probes can be oligodeoxyribonucleotides or oligoribonucleotides, or any modified forms of these polymers that are capable of hybridizing with a target nucleic sequence by complementary base-pairing. Complementary base pairing means sequence-specific base pairing which includes e.g., Watson-Crick base pairing as well as other forms of base pairing such as Hoogsteen base pairing. Modified forms include 2'-O-methyl oligoribonucleotides and so-called PNAs, in which oligodeoxyribonucleotides are linked via peptide bonds rather than phophodiester bonds. The probes can be attached by any linkage to a support (e.g., 3', 5' or via the base). 3' attachment is more usual as this orientation is compatible with the preferred chemistry for solid phase synthesis of oligonucleotides.

The number of probes in the first probe set (and as a consequence the number of probes in additional probe sets) depends on the length of the reference sequence, the number of nucleotides of interest in the reference sequence and the number of interrogation positions per probe. In general, each nucleotide of interest in the reference sequence requires the same interrogation position in the four sets of probes. Consider, as an example, a reference sequence of 100 nucleotides, 50 of which are of interest, and probes each having a single interrogation position. In this situation, the first probe set requires fifty probes, each having one interrogation position corresponding to a nucleotide of interest in the reference sequence. The second, third and fourth probe sets each have a corresponding probe for each probe in the first probe set, and so each also contains a total of fifty probes. The identity of each nucleotide of interest in the reference sequence is determined by comparing the relative hybridization signals at four probes having interrogation positions corresponding to that nucleotide from the four probe sets.

In some reference sequences, every nucleotide is of interest. In other reference sequences, only certain portions in which variants (e.g., mutations or polymorphisms) are concentrated are of interest. In other reference sequences, only particular mutations or polymorphisms and immediately adjacent nucleotides are of interest. Usually, the first probe set has interrogation positions selected to correspond to at least a nucleotide (e.g., representing a point mutation) and one immediately adjacent nucleotide. Usually, the probes in the first set have interrogation positions corresponding to at least 3, 10, 50, 100, 1000, or 20,000 contiguous nucleotides. The probes usually have interrogation positions corresponding to at least 5, 10, 30, 50, 75, 90, 99 or sometimes 100% of the nucleotides in a reference sequence. Frequently, the probes in the first probe set completely span the reference sequence and overlap with one another relative to the reference sequence. For example, in one common arrangement each probe in the first probe set differs from another probe in that set by the omission of a 3' base complementary to the reference sequence and the acquisition of a 5' base complementary to the reference sequence. See, FIG. 13.

The number of probes on the array can be quite large (e.g., $10^5$-$10^6$). However, often only a relatively small proportion (i.e., less than about 50%, 25%, 10%, 5% or 1%) of the total number of probes of a given length are selected to pursue a particular tiling strategy. For example, a complete set of octomer probes comprises 65,536 probes; thus, an array of the invention typically has fewer than 32,768 octomer probes. A complete array of decamer probes comprises 1,048,576 probes; thus, an array of the invention typically has fewer than about 500,000 decamer probes. Often arrays have a lower limit of 25, 50 or 100 probes and an upper limit of 1,000,000, 100,000, 10,000 or 1000 probes. The arrays can have other components besides the probes such as linkers attaching the probes to a support.

Some advantages of the use of only a proportion of all possible probes of a given length include: (i) each position in the array is highly informative, whether or not hybridization occurs; (ii) nonspecific hybridization is minimized; (iii) it is straightforward to correlate hybridization differences with sequence differences, particularly with reference to the hybridization pattern of a known standard; and (iv) the ability to address each probe independently during synthesis, using high resolution photolithography, allows the array to be designed and optimized for any sequence. For example the length of any probe can be varied independently of the others.

Figure 13:
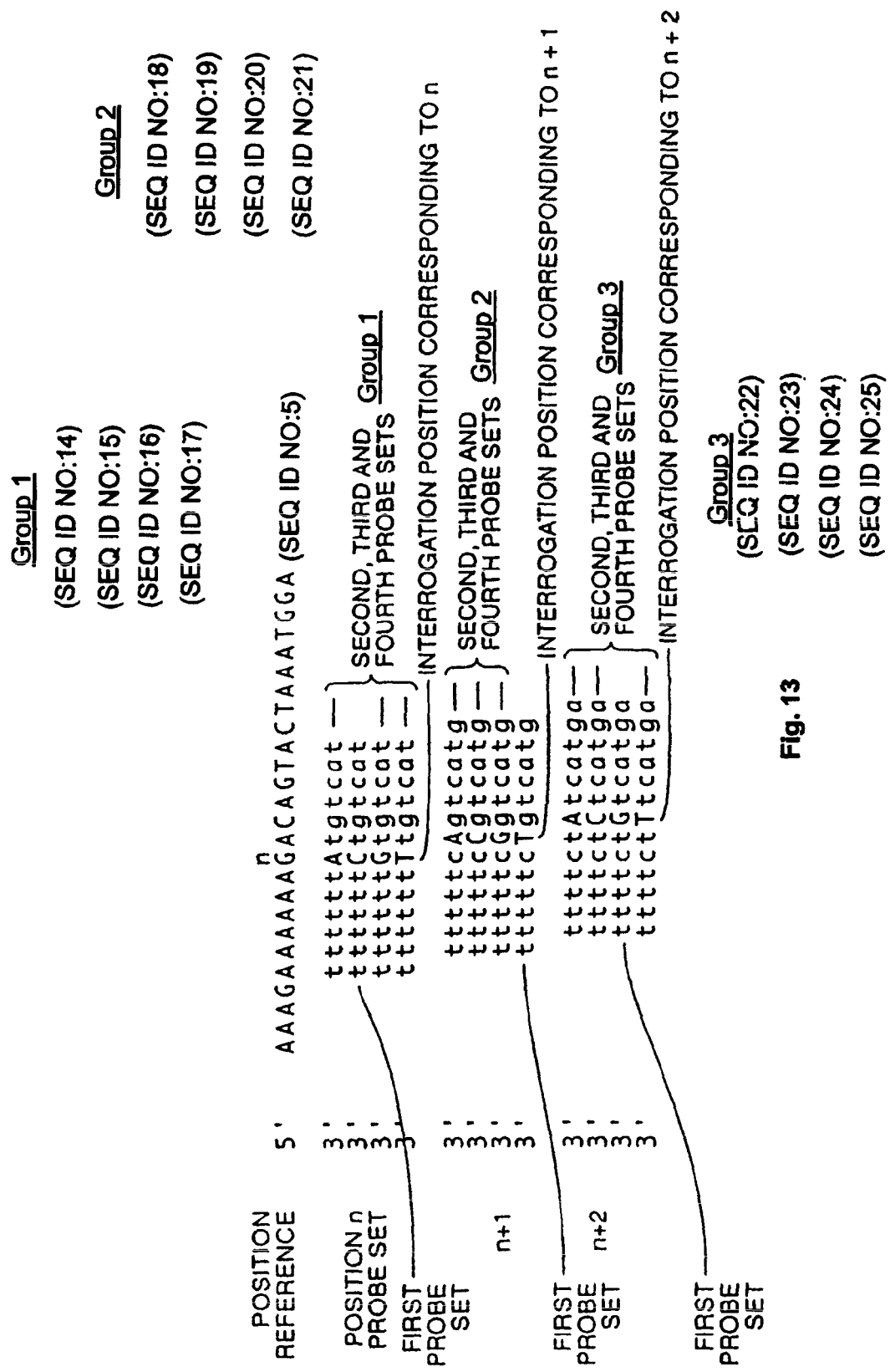
FIG. 13 illustrates the incremental succession of probes in a basic tiling strategy. The figure shows four probe sets, each having three probes. Note that each probe differs from its predecessor in the same set by the acquisition of a 5' nucleotide and the loss of a 3' nucleotide, as well as in the nucleotide occupying the interrogation position.

For conceptual simplicity, the probes in a set are usually arranged in order of the sequence in a lane across the array. A lane contains a series of overlapping probes, which represent or tile across, the selected reference sequence (see, FIG. 13). The components of the four sets of probes are usually laid down in four parallel lanes, collectively constituting a row in the horizontal direction and a series of 4-member columns in the vertical direction. Corresponding probes from the four probe sets (i.e., complementary to the same subsequence of the reference sequence) occupy a column. Each probe in a lane usually differs from its predecessor in the lane by the omission of a base at one end and the inclusion of additional base at the other end as shown in FIG. 13. However, this orderly progression of probes can be interrupted by the inclusion of control probes or omission of probes in certain columns of the array. Such columns serve as controls to orient the array, or gauge the background, which can include target sequence nonspecifically bound to the array.

The probes sets are usually laid down in lanes such that all probes having an interrogation position occupied by an A form an A-lane, all probes having an interrogation position occupied by a C form a C-lane, all probes having an interrogation position occupied by a G form a G-lane, and all probes having an interrogation position occupied by a T (or U) form a T lane (or a U lane). Note that in this arrangement there is not a unique correspondence between probe sets and lanes. Thus, the probe from the first probe set is laid down in the A-lane, C-lane, A-lane, A-lane and T-lane for the five columns in FIG. 14A. The interrogation position on a column of probes corresponds to the position in the target sequence whose identity is determined from analysis of hybridization to the probes in that column. Thus, $I_1$-$I_5$ respectively correspond to $N_1$..$N_5$ in FIG. 14A. The interrogation position can be anywhere in a probe but is usually at or near the central position of the probe to maximize differential hybridization signals between a perfect match and a single-base mismatch. For example, for an 11 mer probe, the central position is the sixth nucleotide.

Although the array of probes is usually laid down in rows and columns as described above, such a physical arrangement of probes on the array is not essential. Provided that the spatial location of each probe in an array is known, the data from the probes can be collected and processed to yield the sequence of a target irrespective of the physical arrangement of the probes on a array. In processing the data, the hybridization signals from the respective probes can be reassorted into any conceptual array desired for subsequent data reduction whatever the physical arrangement of probes on the array.

A range of lengths of probes can be employed in the arrays. As noted above, a probe may consist exclusively of a complementary segments, or may have one or more complementary segments juxtaposed by flanking, trailing and/or intervening segments. In the latter situation, the total length of complementary segments) is more important that the length of the probe. In functional terms, the complementary segment(s) of the first probe sets should be sufficiently long to allow the probe to hybridize detectably more strongly to a reference sequence compared with a variant of the reference including a single base mutation at the nucleotide corresponding to the interrogation position of the probe. Similarly, the complementary segment(s) in corresponding probes from additional probe sets should be sufficiently long to allow a probe to hybridize detectably more strongly to a variant of the reference sequence having a single nucleotide substitution at the interrogation position relative to the reference sequence. A probe usually has a single complementary segment having a length of at least 3 nucleotides, and more usually at least 5, 6, 7, 8, 9, 10, 11, 12, 13, 14, 15, 16, 17, 18, 19, 20, 21, 22, 23, 24, 25 or 30 bases exhibiting perfect complementarity (other than possibly at the interrogation position(s) depending on the probe set) to the reference sequence. In bridging strategies, where more than one segment of complementarity is present, each segment provides at least three complementary nucleotides to the reference sequence and the combined segments provide at least two segments of three or a total of six complementary nucleotides. As in the other strategies, the combined length of complementary segments is typically from 6-30 nucleotides, and preferably from about 9-21 nucleotides. The two segments are often approximately the same length. Often, the probes (or segment of complementarity within probes) have an odd number of bases, so that an interrogation position can occur in the exact center of the probe.

In some arrays, all probes are the same length. Other arrays employ different groups of probe sets, in which case the probes are of the same size within a group, but differ between different groups. For example, some arrays have one group comprising four sets of probes as described above in which all the probes are 11 mers, together with a second group comprising four sets of probes in which all of the probes are 13 mers. Of course, additional groups of probes can be added. Thus, some arrays contain, e.g., four groups of probes having sizes of 11 mers, 13 mers, 15 mers and 17 mers. Other arrays have different size probes within the same group of four probe sets. In these arrays, the probes in the first set can vary in length independently of each other. Probes in the other sets are usually the same length as the probe occupying the same column from the first set. However, occasionally different lengths of probes can be included at the same column position in the four lanes. The different length probes are included to equalize hybridization signals from probes irrespective of whether A-T or C-G bonds are formed at the interrogation position.

The length of probe can be important in distinguishing between a perfectly matched probe and probes showing a single-base mismatch with the target sequence. The discrimination is usually greater for short probes. Shorter probes are usually also less susceptible to formation of secondary structures. However, the absolute amount of target sequence bound, and hence the signal, is greater for larger probes. The probe length representing the optimum compromise between these competing considerations may vary depending on, inter alia, the GC content of a particular region of the target DNA sequence, secondary structure, synthesis efficiency and cross-hybridization. In some regions of the target, depending on hybridization conditions, short probes (e.g., 11 mers) may provide information that is inaccessible from longer probes (e.g., 19 mers) and vice versa. Maximum sequence information can be read by including several groups of different sized probes on the array as noted above. However, for many regions of the target sequence, such a strategy provides redundant information in that the same sequence is read multiple times from the different groups of probes. Equivalent information can be obtained from a single group of different sized probes in which the sizes are selected to maximize readable sequence at particular regions of the target sequence. The strategy of customizing probe length within a single group of probe sets minimizes the total number of probes required to read a particular target sequence. This leaves ample capacity for the array to include probes to other reference sequences.

The invention provides an optimization block which allows systematic variation of probe length and interrogation position to optimize the selection of probes for analyzing a particular nucleotide in a reference sequence. The block comprises alternating columns of probes complementary to the wildtype target and probes complementary to a specific mutation. The interrogation position is varied between columns and probe length is varied down a column. Hybridization of the array to the reference sequence or the mutant form of the reference sequence identifies the probe length and interrogation position providing the greatest differential hybridization signal.

Variation of interrogation position in probes for analyzing different regions of a target sequence offers a number of advantages. If a segment of a target sequence contains two closely spaced mutations, m1, and m2, and probes for analyzing that segment have an interrogation position at or near the middle, then no probe has an interrogation position aligned with one of the mutations without overlapping the other mutation (see, first probe in FIG. 14B). Thus, the presence of a mutation would have to be detected by comparing the hybridization signal of a single-mismatched probe with a double-mismatched probe. By contrast, if the interrogation position is near the 3' end of the probes, probes can have their interrogation position aligned with m1 without overlapping m2 (second probe in FIG. 14B). Thus, the mutation can be detected by a comparison of a perfectly matched probe with single based mismatched probes. Similarly, if the interrogation position is near the 5' end of the probes, probes can have their interrogation position aligned with m2 without overlapping m1 (third probe in FIG. 14B).

Variation of the interrogation position also offers the advantage of reducing loss of signal due to self-annealing of certain probes. FIG. 14C shows a target sequence having a nucleotide X, which can be read either from the relative signals of the four probes having a central interrogation position (shown at the left of the figure) or from the four probes having the interrogation position near the three prime end (shown at the right of the figure). Only the probes having the central interrogation position are capable of self-annealing. Thus, a higher signal is obtained from the probes having the interrogation position near the terminus.

The probes are designed to be complementary to either strand of the reference sequence (e.g., coding or non-coding). Some arrays contain separate groups of probes, one complementary to the coding strand, the other complementary to the noncoding strand. Independent analysis of coding and noncoding strands provides largely redundant information. However, the regions of ambiguity in reading the coding strand are not always the same as those in reading the noncoding strand. Thus, combination of the information from coding and noncoding strands increases the overall accuracy of sequencing.

Some arrays contain additional probes or groups of probes designed to be complementary to a second reference sequence. The second reference sequence is often a subsequence of the first reference sequence bearing one or more commonly occurring mutations or interstrain variations. The second group of probes is designed by the same principles as described above except that the probes exhibit complementarity to the second reference sequence. The inclusion of a second group is particular useful for analyzing short subsequences of the primary reference sequence in which multiple mutations are expected to occur within a short distance commensurate with the length of the probes (i.e., two or more mutations within 9 to 21 bases). Of course, the same principle can be extended to provide arrays containing groups of probes for any number of reference sequences. Alternatively, the arrays may contain additional probe(s) that do not form part of a tiled array as noted above, but rather serves as probe(s) for a conventional reverse dot blot. For example, the presence of mutation can be detected from binding of a target sequence to a single oligomeric probe harboring the mutation. Preferably, an additional probe containing the equivalent region of the wildtype sequence is included as a control.

Although only a subset of probes is required to analyze a particular target sequence, it is quite possible that other probes superfluous to the contemplated analysis are also included on the array. In the extreme case, the array could can a complete set of all probes of a given length notwithstanding that only a small subset is required to analyze the particular reference sequence of interest. Although such a situation might appear wasteful of resources, a array including a complete set of probes offers the advantage of including the appropriate subset of probes for analyzing any reference sequence. Such a array also allows simultaneous analysis of a reference sequence from different subsets of probes (e.g., subsets having the interrogation site at different positions in the probe).

In its simplest terms, the analysis of a array reveals whether the target sequence is the same or different from the reference sequence. If the two are the same, all probes in the first probe set show a stronger hybridization signal than corresponding probes from other probe sets. If the two are different, most probes from the first probe set still show a stronger hybridization signal than corresponding probes from the other probe sets, but some probes from the first probe set do not. Thus, when a probe from another probe sets light up more strongly than the corresponding probe from the first probe set, this provides a simple visual indication that the target sequence and reference sequence differ.

Figure 15:
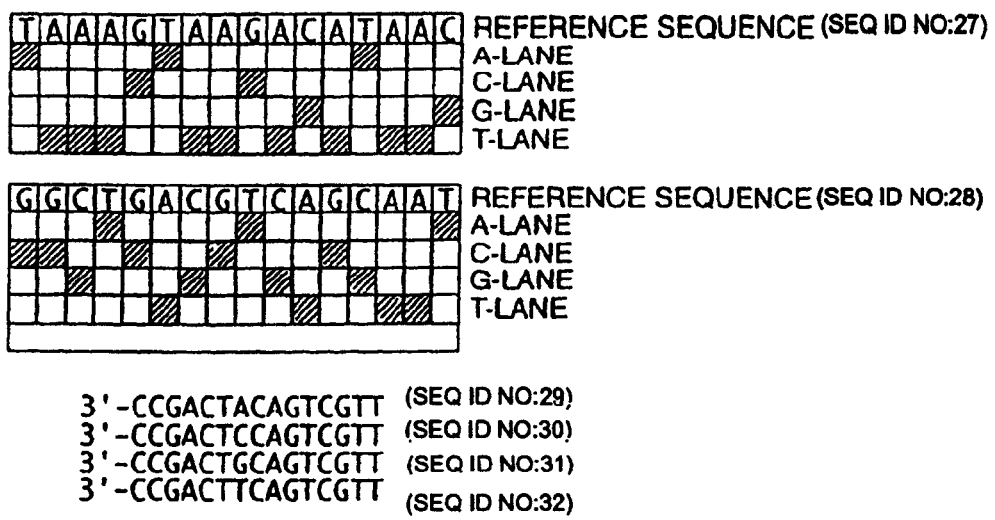
FIG. 15 illustrates a hybridization pattern of chip having probes laid down in lanes. Dark patches indicate hybridization. The probes in the lower part of the figure occur at the column of the array indicated by the arrow when the probes length is 15 and the interrogation position 7.

The arrays also reveal the nature and position of differences between the target and reference sequence. The arrays are read by comparing the intensities of labelled target bound to the probes in an array. Specifically, for each nucleotide of interest in the target sequence, a comparison is performed between probes having an interrogation position aligned with that position. These probes form a column (actual or conceptual) on the array. For example, a column often contains one probe from each of A, C, G and T lanes. The nucleotide in the target sequence is identified as the complement of the nucleotide occupying the interrogation position in the probe showing the highest hybridization signal from a column. FIG. 15 shows the hybridization pattern of a array hybridized to its reference sequence. The dark square in each column represents the probe from the column having the highest hybridization signal. The sequence can be read by following the pattern of dark squares from left to right across the array. The first dark square is in the A lane indicating that the nucleotide occupying the interrogation position of the probe represented by this square is an A. The first nucleotide in the reference sequence is the complement of nucleotide occupying the interrogation position of this probe (i.e., a T). Similarly, the second dark square is in the T-lane, from which it can be deduced that the second nucleotide in the reference sequence is an A. Likewise the third dark square is in the T-lane, from which it can be deduced that the third nucleotide in the reference sequence is also an A, and so forth. By including probes in the first probe set (and by implication in the other probe sets) with interrogation positions corresponding to every nucleotide in a reference sequence, it is possible to read substantially every nucleotide in a target sequence, thereby revealing the complete or nearly complete sequence of the target.

Of the four probes in a column, only one can exhibit a perfect match to the target sequence whereas the others usually exhibit at least a one base pair mismatch. The probe exhibiting a perfect match usually produces a substantially greater hybridization signal than the other three probes in the column and is thereby easily identified. However, in some regions of the target sequence, the distinction between a perfect match and a one-base mismatch is less clear. Thus, a call ratio is established to define the ratio of signal from the best hybridizing probes to the second best hybridizing probe that must be exceeded for a particular target position to be read from the probes. A high call ratio ensures that few if any errors are made in calling target nucleotides, but can result in some nucleotides being scored as ambiguous, which could in fact be accurately read. A lower call ratio results in fewer ambiguous calls, but can result in more erroneous calls. It has been found that at a call ratio of 1.2 virtually all calls are accurate. However, a small but significant number of bases (e.g., up to about 10%) may have to be scored as ambiguous.

Although small regions of the target sequence can sometimes be ambiguous, these regions usually occur at the same or similar segments in different target sequences. Thus, for precharacterized mutations, it is known in advance whether that mutation is likely to occur within a region of unambiguously determinable sequence.

An array of probes is most useful for analyzing the reference sequence from which the probes were designed and variants of that sequence exhibiting substantial sequence similarity with the reference sequence (e.g., several single-base mutants spaced over the reference sequence). When an array is used to analyze the exact reference sequence from which it was designed, one probe exhibits a perfect match to the reference sequence, and the other three probes in the same column exhibits single-base mismatches. Thus, discrimination between hybridization signals is usually high and accurate sequence is obtained. High accuracy is also obtained when an array is used for analyzing a target sequence comprising a variant of the reference sequence that has a single mutation relative to the reference sequence, or several widely spaced mutations relative to the reference sequence. At different mutant loci, one probe exhibits a perfect match to the target, and the other three probes occupying the same column exhibit single-base mismatches, the difference (with respect to analysis of the reference sequence) being the lane in which the perfect match occurs.

For target sequences showing a high degree of divergence from the reference strain or incorporating several closely spaced mutations from the reference strain, a single group of probes (i.e., designed with respect to a single reference sequence) will not always provide accurate sequence for the highly variant region of this sequence. At some particular columnar positions, it may be that no single probe exhibits perfect complementarity to the target and that any comparison must be based on different degrees of mismatch between the four probes. Such a comparison does not always allow the target nucleotide corresponding to that columnar position to be called. Deletions in target sequences can be detected by loss of signal from probes having interrogation positions encompassed by the deletion. However, signal may also be lost from probes having interrogation positions closely proximal to the deletion resulting in some regions of the target sequence that cannot be read. Target sequence bearing insertions will also exhibit short regions including and proximal to the insertion that usually cannot be read.

The presence of short regions of difficult-to-read target because of closely spaced mutations, insertions or deletions, does not prevent determination of the remaining sequence of the target as different regions of a target sequence are determined independently. Moreover, such ambiguities as might result from analysis of diverse variants with a single group of probes can be avoided by including multiple groups of probe sets on a array. For example, one group of probes can be designed based on a full-length reference sequence, and the other groups on subsequences of the reference sequence incorporating frequently occurring mutations or strain variations.

A particular advantage of the present sequencing strategy over conventional sequencing methods is the capacity simultaneously to detect and quantify proportions of multiple target sequences. Such capacity is valuable, e.g., for diagnosis of patients who are heterozygous with respect to a gene or who are infected with a virus, such as HIV, which is usually present in several polymorphic forms. Such capacity is also useful in analyzing targets from biopsies of tumor cells and surrounding tissues. The presence of multiple target sequences is detected from the relative signals of the four probes at the array columns corresponding to the target nucleotides at which diversity occurs. The relative signals of the four probes for the mixture under test are compared with the corresponding signals from a homogeneous reference sequence. An increase in a signal from a probe that is mismatched with respect to the reference sequence, and a corresponding decrease in the signal from the probe which is matched with the reference sequence, signal the presence of a mutant strain in the mixture. The extent in shift in hybridization signals of the probes is related to the proportion of a target sequence in the mixture. Shifts in relative hybridization signals can be quantitatively related to proportions of reference and mutant sequence by prior calibration of the array with seeded mixtures of the mutant and reference sequences. By this means, a array can be used to detect variant or mutant strains constituting as little as 1, 5, 20, or 25% of a mixture of stains.

Similar principles allow the simultaneous analysis of multiple target sequences even when none is identical to the reference sequence. For example, with a mixture of two target sequences bearing first and second mutations, there would be a variation in the hybridization patterns of probes having interrogation positions corresponding to the first and second mutations relative to the hybridization pattern with the reference sequence. At each position, one of the probes having a mismatched interrogation position relative to the reference sequence would show an increase in hybridization signal, and the probe having a matched interrogation position relative to the reference sequence would show a decrease in hybridization signal. Analysis of the hybridization pattern of the mixture of mutant target sequences, preferably in comparison with the hybridization pattern of the reference sequence, indicates the presence of two mutant target sequences, the position and nature of the mutation in each strain, and the relative proportions of each strain.

In a variation of the above method, several target sequences target sequences are differentially labelled before being simultaneously applied to the array. For example, each different target sequence can be labelled with a fluorescent labels emitting at different wavelength. After applying a mixtures of target sequence to the arrays, the individual target sequences can be distinguished and independently analyzed by virtue of the differential labels. For example, the methods target sequences obtained from a patient at different stages of a disease can be differently labelled and analyzed simultaneously, facilitating identification of new mutations.

2. Block Tiling

In block tiling, a perfectly matched (or wildtype) probe is compared with multiple sets of mismatched or mutant probes. The perfectly matched probe and the multiple sets of mismatched probes with which it is compared collectively form a group or block of probes on the array. Each set comprises at least one, and usually, three mismatched probes. FIG. 16 shows a perfectly matched probe (CAATCGA) having three interrogation positions ($I_1$, $I_2$ and $I_3$). The perfectly matched probe is compared with three sets of probes (arbitrarily designated A, B and C), each having three mismatched probes. In set A, the three mismatched probes are identical to a sequence comprising the perfectly matched probe or a subsequence thereof including the interrogation positions, except at the first interrogation position. That is, the mismatched probes in the set A differ from the perfectly matched probe set at the first interrogation position. Thus, the relative hybridization signals of the perfectly matched probe and the mismatched probes in the set A indicates the identity of the nucleotide in a target sequence corresponding to the first interrogation position. This nucleotide is the complement of the nucleotide occupying the interrogation position of the probe showing the highest signal. Similarly, set B comprises three mismatched probes, that differ from the perfectly matched probe at the second interrogation position. The relative hybridization intensities of the perfectly matched probe and the three mismatched probes of set B reveal the identity of the nucleotide in the target sequence corresponding to the second interrogation position (i.e., n2 in FIG. 16). Similarly, the three mismatched probes in set C in FIG. 16 differ from the perfectly matched probe at the third interrogation position. Comparison of the hybridization intensities of the perfectly matched probe and the mismatched probes in the set C reveals the identity of the nucleotide in the target sequence corresponding to the third interrogation position (n3).

As noted above, a perfectly matched probe may have seven or more interrogation positions. If there are seven interrogation positions, there are seven sets of three mismatched probe, each set serving to identify the nucleotide corresponding to one of the seven interrogation positions. Similarly, if there are 20 interrogation positions in the perfectly matched probe, then 20 sets of three mismatched probes are employed. As in other tiling strategies, selected probes can be omitted if it is known in advance that only certain types of mutations are likely to arise.

Each block of probes allows short regions of a target sequence to be read. For example, for a block of probes having seven interrogation positions, seven nucleotides in the target sequence can be read. Of course, a array can contain any number of blocks depending on how many nucleotides of the target are of interest. The hybridization signals for each block can be analyzed independently of any other block. The block tiling strategy can also be combined with other tiling strategies, with different parts of the same reference sequence being tiled by different strategies.

The block tiling strategy is a species of the basic tiling strategy discussed above, in which the probe from the first probe set has more than one interrogation position. The perfectly matched probe in the block tiling strategy is equivalent to a probe from the first probe set in the basic tiling strategy. The three mismatched probes in set A in block tiling are equivalent to probes from the second, third and fourth probe sets in the basic tiling strategy. The three mismatched probes in set B of block tiling are equivalent to probes from additional probe sets in basic tiling arbitrarily designated the fifth, sixth and seventh probe sets. The three mismatched probes in set C of blocking tiling are equivalent to probes from three further probe sets in basic tiling arbitrarily designated the eighth, ninth and tenth probe sets.

The block tiling strategy offers two advantages over a basic strategy in which each probe in the first set has a single interrogation position. One advantage is that the same sequence information can be obtained from fewer probes. A second advantage is that each of the probes constituting a block (i.e., a probe from the first probe set and a corresponding probe from each of the other probe sets) can have identical 3' and 5' sequences, with the variation confined to a central segment containing the interrogation positions. The identity of 3' sequence between different probes simplifies the strategy for solid phase synthesis of the probes on the array and results in more uniform deposition of the different probes on the array, thereby in turn increasing the uniformity of signal to noise ratio for different regions of the array.

V. Enzymatic Discrimination Enhancement

Unfortunately using the foregoing tiling strategies as well as other Sequencing By Hybridization techniques (e.g., those disclosed in co-pending application Ser. Nos. 08/082,937 (filed Jun. 25, 1993) and 08/168,904 (filed Dec. 15, 1993), each of which are incorporated herein by reference for all purposes), it is frequently difficult to discriminate between fully complementary hybrids and those that differ by one or more base pairs. However, it has now been determined that sequencing by hybridization can be improved by using various enzymes that catalyze oligonucleotide cleavage and ligation reactions. More particularly, discrimination between fully complementary hybrids and those that differ by one or more base pairs can be greatly enhanced by using various enzymes that catalyze oligonucleotide cleavage and ligation reactions.

A. Enhanced Discrimination Using Nuclease Treatment

Nuclease treatment can be used to improve the quality of hybridization signals on high density oligonucleotide arrays. More particularly, after the array of oligonucleotides has been combined with a labelled target nucleic acid to form target-oligonucleotide hybrid complexes, the target-oligonucleotide hybrid complexes are treated with a nuclease and, in turn, they are washed to remove non-perfectly complementary target-oligonucleotide hybrid complexes. Following nuclease treatment, the target: oligonucleotide hybrid complexes which are perfectly complementary are more readily identified. From the location of the labelled targets, the oligonucleotide probes which hybridized with the targets can be identified and, in turn, the sequence of the target nucleic acid can more readily be determined or verified.

The particular nuclease used will depend on the target nucleic acid being sequenced. If the target is RNA, a RNA nuclease is used. Similarly, if the target is DNA, a DNA nuclease is used. RNase A is an example of an RNA nuclease that can be used to increase the quality of RNA hybridization signals on high density oligonucleotide arrays. RNase A effectively recognizes and cuts single-stranded RNA, including RNA in RNA:DNA hybrids that is not in a perfect double-stranded structure. Moreover, RNA bulges, loops, and even single base mismatches can be recognized and cleaved by RNase A. In addition, RNase A recognizes and cleaves target RNA which binds to multiple oligonucleotide probes present on the substrate if there are intervening single-stranded regions. S1 nuclease and Mung Bean nuclease are examples of DNA nucleases which can be used to improve the DNA hybridization signals on high density oligonucleotide arrays. Other nucleases, which will be apparent to those of skill in the art, can similarly be used to increase the quality of RNA hybridization signals on high density oligonucleotide arrays and, in turn, to more accurately determine the sequence of the target nucleic acid.

Figure 4:
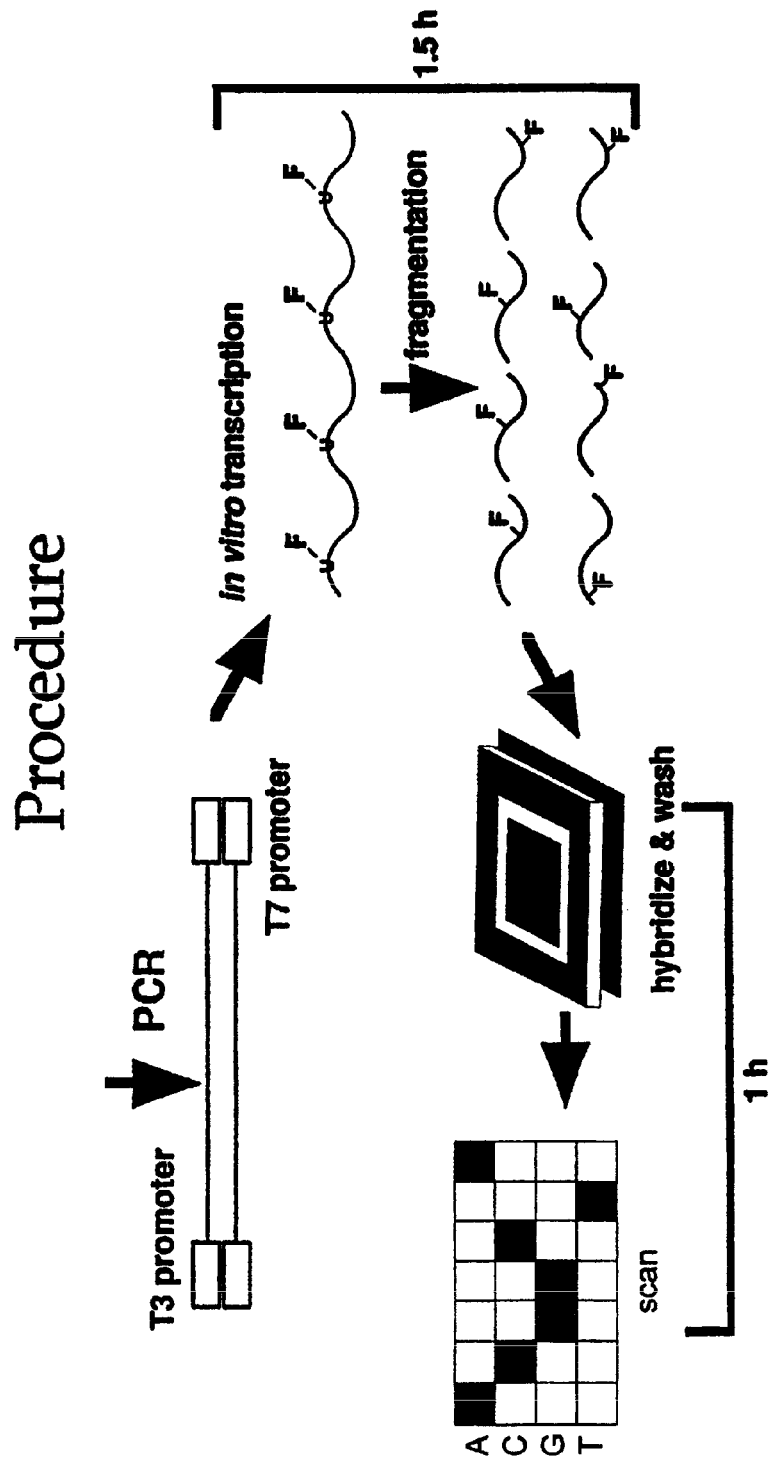
FIG. 4. illustrates a hybridization procedure which can be used prior to nuclease treatment.

FIG. 4 is a schematic outline of a hybridization procedure which can be carried out prior to nuclease treatment. Fluorescein-UTP and -CTP labelled RNA is prepared from a PCR product by in vitro transcription. The RNA is fragmented by heating and allowed to hybridize with an array of oligonucleotide probes on a single substrate. The array of oligonucleotide probes is generated using the tiling procedure described so that the array of oligonucleotide probes is capable of recognizing substantially all of the possible subsequences present in the target RNA. Moreover, for purposes of comparison, the array of oligonucleotides is preferably generated so that all of the four possible probes for a given position to be identified are in close proximity to one another (i.e., so that they are in predefined regions which are near to one another). Following hybridization, the substrate is rinsed with the hybridization buffer and a quantitative fluorescence image of the hybridization pattern is obtained by, for example, scanning the substrate with a confocal microscope. It should be noted that confocal detection allows hybridization to be measured in the presence of excess labelled target and, hence, if desired, hybridization can be detected in real time.

Following hybridization, the substrate having an array of target: oligonucleotide hybridization complexes thereon is contacted with a nuclease. This is most simply carried out by adding a solution of the nuclease to the surface of the substrate. Alternatively, however, this can be carried out by flowing a solution of the nuclease over the substrate using, for example, techniques similar to the flow channel methods described above. The nuclease solution is typically formed using the buffer used to carry out the hybridization reaction (i.e., the hybridization buffer). The concentration of the nuclease will vary depending on the particular nuclease used, but will typically range from about 0.05 µg/ml to about 2 mg/ml. Moreover, the time in which the array of target:oligonucleotide hybridization complexes is in contact with the nuclease will vary. Typically, nuclease treatment is carried out for a period of time ranging from about 5 minutes to 3 hours. Following treatment with the nuclease, the substrate is again washed with the hybridization buffer, and a quantitative fluorescence image of the hybridization pattern is obtained by scanning the substrate with, for example, a confocal microscope.

As such, nuclease treatment can be used following hybridization to improve the quality of hybridization signals on high density oligonucleotide arrays and, in turn, to more accurately determine the sequence of the target nucleic acid. It will be readily apparent to the those of skill in the art that the foregoing is intended to illustrate, and not restrict, the way in which an array of target:oligonucleotide hybrid complexes can be treated with a nuclease to improve hybridization signals on high density oligonucleotide arrays.

In another aspect, the present invention provides a method for obtaining sequencing information about an unlabeled target oligonucleotide, comprising: (a) contacting an unlabeled target oligonucleotide with a library of labeled oligonucleotide probes, each of the oligonucleotide probes having a known sequence and being attached to a solid support at a known position, to hybridize the target oligonucleotide to at least one member of the library of probes, thereby forming a hybridized library; (b) contacting the hybridized library with a nuclease capable of cleaving double-stranded oligonucleotides to release from the hybridized library a portion of the labeled oligonucleotide probes or fragments thereof; and (c) identifying the positions of the hybridized library from which labeled probes or fragments thereof have been removed, to determine the sequence of the unlabeled target oligonucleotide.

In this aspect of the invention a library of oligonucleotide probes is prepared, for example, using the VLSIPS™ technology describe above (See, Section III, supra). Once the library of probes has been prepared, the 5' terminus of each probe can be labeled with a detectable label such as those described in Section V, infra. Preferably, the label is a fluorescent label.

The library of labeled oligonucleotide probes is then contacted with an unlabeled target oligonucleotide. The unlabeled oligonucleotide can be synthetic or can be isolated from natural sources. In preferred embodiments, the unlabeled oligonucleotide is genomic DNA or RNA. For example, purified DNA or a whole-cell digest which has been partially sequenced can be lightly fragmented (e.g., by digestion with a restriction enzyme which provides infrequent cuts and which infrequently cuts within any of the regions desired to be resequenced). The fragments of interest can be separated using a column containing probes complementary to a part of the sequence of interest. The complementary fragments are bound in the column while the remaining DNA is washed through. The fragments of interest are then removed (e.g., by heat or by chemical means) and contacted with the library of probes.

Once the library of probes has been contacted with the target oligonucleotide under conditions sufficient for hybridization to occur, the resulting hybridized library is contacted with an appropriate nuclease enzyme. Alternatively, the nuclease can be introduced to the library in the same mixture as the target oligonucleotide. The nuclease can be any of a variety of commercially available nucleases which are capable of cleaving double-stranded DNA. Examples of such nucleases include DNase I.

The hybridized library which has been contacted with the nuclease is then washed to remove the label from those positions wherein hybridization has taken place. By scanning the washed library with a detector to determine the presence or absence of labels in a region, hybridization information can be obtained. This method is applicable to resequencing tilings (see, Section IV, supra), mutation detection and other combinatorial methods. Other advantages exist to the present method, including (i) the use of unlabeled target oligonucleotide, which simplifies target preparation and allows genomic material to be used directly, (ii) the use of a variety of nucleases which can be selected for cleaving the target and probe, the probe alone, or probe-probe interaction, and (iii) application using existing VLSIPS technology.

The foregoing enzymatic discrimination enhancement methods can be used in all instances where improved discrimination between fully complementary hybrids and those that differ by one or more base pairs would be helpful. More particularly, such methods can be used to more accurately determine the sequence (e.g., de novo sequencing), or monitor mutations, or resequence the target nucleic acid (i.e., such methods can be used in conjunction with a second sequencing procedure to provide independent verification).

B. Enhanced Discrimination Using Ligation Reactions

Ligation reactions can be used to discriminate between fully complementary hybrids and those that differ by one or more base pairs. More particularly, an array of oligonucleotides is generated on a substrate (in the 3' to 5' direction) using any one of the methods described above. The oligonucleotides in the array are generally shorter in length than the target nucleic acid so that when hybridized to the target nucleic acid, the target nucleic acid generally has a 3' overhang. In this embodiment, the target nucleic acid is not necessarily labelled. After the array of oligonucleotides has been combined with the target nucleic acid to form target-oligonucleotide hybrid complexes, the target-oligonucleotide hybrid complexes are contacted with a ligase and a labelled, ligatable probe or, alternatively, with a pool of labelled, ligatable probes. The ligation reaction of the labelled, ligatable probes to the 5' end of the oligonucleotide probes on the substrate will occur, in the presence of the ligase, predominantly when the target:oligonucleotide hybrid has formed with correct base-pairing near the 5' end of the oligonucleotide probe and where there is a suitable 3' overhang of the target nucleic acid to serve as a template for hybridization and ligation. After the ligation reaction, the substrate is washed (multiple times if necessary) with water at a temperature of about 40° C. to 50° C. to remove the target nucleic acid and the labelled, unligated probes. Thereafter, a quantitative fluorescence image of the hybridization pattern is obtained by scanning the substrate with, for example, a confocal microscope, and labelled oligonucleotide probes, i.e., the oligonucleotide probes which are perfectly complementary to the target nucleic acid, are identified. Using this information, sequence information about the target nucleic acid can be determined.

Any enzyme that catalyzes the formation of a phosphodiester bond at the site of a single-stranded break in duplex DNA can be used to enhance discrimination between fully complementary hybrids and those that differ by one or more base pairs. Such ligases include, but are not limited to, T4 DNA ligase, ligases isolated from *E. coli* and ligases isolated from other bacteriophages. The concentration of the ligase will vary depending on the particular ligase used, the concentration of target and buffer conditions, but will typically range from about 500 units/ml to about 5,000 units/ml. Moreover, the time in which the array of target:oligonucleotide hybridization complexes is in contact with the ligase will vary. Typically, the ligase treatment is carried out for a period of time ranging from minutes to hundreds of hours.

Figure 8:
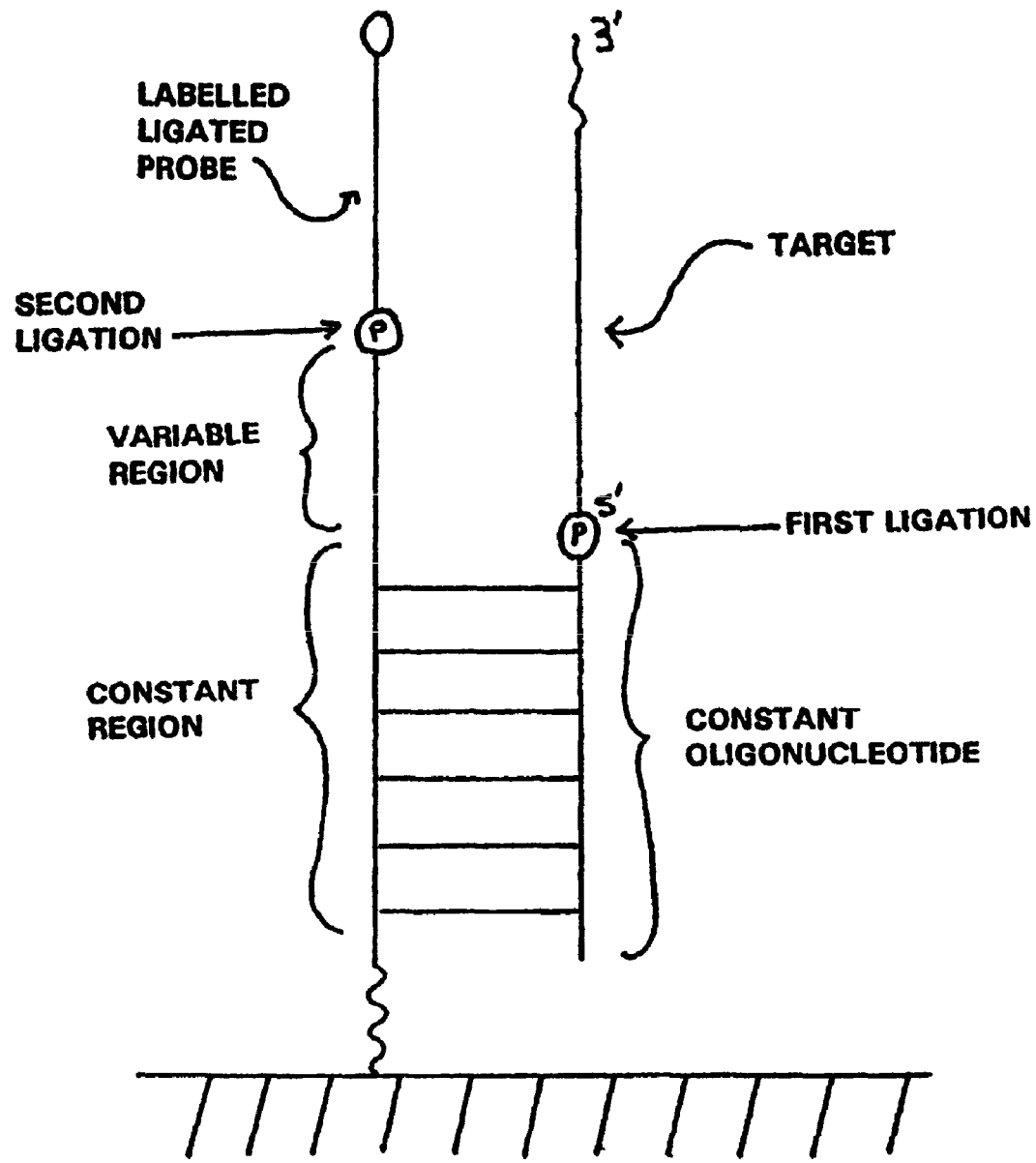
FIG. 8 illustrates a method for improving the sequencing of the 5' end of a randomly fragmented target using 2 ligation reactions.

In a further embodiment, the present invention provides another method which can be used to improve discrimination of base-pair mismatches near the 5' end of the immobilized probes. More particularly, the present invention provides a method for sequencing an unlabeled target oligonucleotide, the method comprising: (a) combining: (i) a substrate comprising an array of positionally distinguishable oligonucleotide probes each of which has a constant region and a variable region, the variable region capable of binding to a defined subsequence of preselected length; (ii) a constant oligonucleotide having a sequence which is complementary to the constant region of the oligonucleotide probes; (iii) a target oligonucleotide whose sequence is to be determined; and (iv) a ligase, thereby forming target oligonucleotide-oligonucleotide probe hybrid complexes of complementary subsequences of known sequence; (b) contacting the target oligonucleotide-oligonucleotide probe hybrid complexes with a ligase and a pool of labelled, ligatable oligonucleotide probes of a preselected length, the pool of labelled, ligatable oligonucleotide probes representing all possible sequences of the preselected length; (c) removing unbound target nucleic acid and labelled, unligated oligonucleotide probes; and (d) determining which of the oligonucleotide probes contain the labelled, ligatable oligonucleotide probe as an indication of a subsequence which is perfectly complementary to a subsequence of the target oligonucleotide. See, FIG. 8, which illustrates this method.

In this method, the constant region is typically from about 10 to about 14 nucleotides in length, whereas the variable region is typically from about 6 to about 8 nucleotides in length. The labelled, ligatable oligonucleotide probes have a preselected length, and the pool of such probes represents all possible sequences of the preselected length. Thus, if the probe is 6 nucleotides in length, all possible 6-mers are present in the pool. As with the previously described method, any enzyme that catalyzes the formation of a phosphodiester bond at the site of a single-strand break in duplex DNA can be used to enhance discrimination between fully complementary hybrids and those that differ by one or more base pairs. Such ligases include, but are not limited to, T4 DNA ligase, ligases isolated from *E. coli* and ligases isolated from other bacteriophages. The concentration of the ligase will vary depending on the particular ligase used, the concentration of target and buffer conditions, but will typically range from about 500 units/ml to about 5,000 units/ml. Moreover, the time in which the array of target oligonucleotide:oligonucleotide probe hybrid complexes is in contact with the ligase will vary. Typically, the ligase treatment is carried out for a period of time ranging from minutes to hundreds of hours. In addition, it will be readily apparent to those of skill that the two ligation reactions can either be done sequentially or, alternatively, simultaneously in a single reaction mix that contains: target oligonucleotides; constant oligonucleotides; a pool of labeled, ligatable probes; and a ligase.

In the above method, the first ligation reaction will occur only if the 5' end of the target oligonucleotide (i.e., the last 3-4 bases) matches the variable region of the oligonucleotide probe. Similarly, the second ligation reaction, which adds a label to the probe, will occur efficiently only if the first ligation reaction was successful and if the ligated target is complementary to the 5' end of the probe. Thus, this method provides for specificity at both ends of the variable region. Moreover, this method is advantageous in that it allows a shorter variable probe region to be used; increases probe:target specificity and removes the necessity of labeling the target.

As such, ligation reactions can effectively be used to improve discrimination of base-pair mismatches near the 5' end of the immobilized probe, mismatches that are often poorly discriminated following hybridization alone. The foregoing enhancement discrimination methods involving the use of ligation reactions can be used in all instances where improved discrimination between fully complementary hybrids and those that differ by one or more base pairs would be helpful. More particularly, such methods can be used to more accurately determine the sequence (e.g., de novo sequencing), or monitor mutations, or resequence the target nucleic acid (i.e., such methods can be used in conjunction with a second sequencing procedure to provide independent verification). It will be readily apparent to those of skill in the art that the foregoing is intended to illustrate, and not restrict, the way in which an array of target:oligonucleotide hybrid complexes can be treated with a ligase and a pool of labelled, ligatable probes to improve hybridization signals on high density oligonucleotide arrays.

VI. DETECTION METHODS

Methods for detection depend upon the label selected. The criteria for selecting an appropriate label are discussed below, however, a fluorescent label is preferred because of its extreme sensitivity and simplicity. Standard labeling procedures are used to determine the positions where interactions between a target sequence and a reagent take place. For example, if a target sequence is labeled and exposed to a matrix of different oligonucleotide probes, only those locations where the oligonucleotides interact with the target will exhibit any signal. In addition to using a label, other methods may be used to scan the matrix to determine where interaction takes place. The spectrum of interactions can, of course, be determined in a temporal manner by repeated scans of interactions which occur at each of a multiplicity of conditions. However, instead of testing each individual interaction separately, a multiplicity of sequence interactions may be simultaneously determined on a matrix.

A. Labeling Techniques

The target nucleic acid can be labeled using any of a number of convenient detectable markers. A fluorescent label is preferred because it provides a very strong signal with low background. It is also optically detectable at high resolution and sensitivity through a quick scanning procedure. Other potential labeling moieties include, radioisotope, chemiluminescent compounds, labeled binding proteins, heavy metal atoms, spectroscopic markers, magnetic labels, and linked enzymes.

In another embodiment, different targets can be simultaneously sequenced where each target has a different label. For instance, one target could have a green fluorescent label and a second target could have a red fluorescent label. The scanning step will distinguish cites of binding of the red label from those binding the green fluorescent label. Each sequence can be analyzed independently from one another.

Suitable chromogens which can be employed include those molecules and compounds which adsorb light in a distinctive range of wavelengths so that a color can be observed or, alternatively, which emit light when irradiated with radiation of a particular wave length or wave length range, e.g., fluorescers.

A wide variety of suitable dyes are available, being primary chosen to provide an intense color with minimal absorption by their surroundings. Illustrative dye types include quinoline dyes, triarylmethane dyes, acridine dyes, alizarine dyes, phthaleins, insect dyes, azo dyes, anthraquinoid dyes, cyanine dyes, phenazathionium dyes, and phenazoxonium dyes.

A wide variety of fluorescers can be employed either by alone or, alternatively, in conjunction with quencher molecules. Fluorescers of interest fall into a variety of categories having certain primary functionalities. These primary functionalities include 1- and 2-aminonaphthalene, p,p'-diaminostilbenes, pyrenes, quaternary phenanthridine salts, 9-aminoacridines, p,p'-diaminobenzophenone imines, anthracenes, oxacarbocyanine, marocyanine, 3-aminoequilenin, perylene, bisbenzoxazole, bis-p-oxazolyl benzene, 1,2-benzophenazin, retinol, bis-3-aminopyridinium salts, hellebrigenin, tetracycline, sterophenol, benzimidzaolylphenylamine, 2-oxo-3-chromen, indole, xanthen, 7-hydroxycoumarin, phenoxazine, salicylate, strophanthidin, porphyrins, triarylmethanes and flavin. Individual fluorescent compounds which have functionalities for linking or which can be modified to incorporate such functionalities include, e.g., dansyl chloride; fluoresceins such as 3,6-dihydroxy-9-phenylxanthhydrol; rhodamineisothiocyanate; N-phenyl 1-amino-8-sulfonatonaphthalene; N-phenyl 2-amino-6-sulfonatonaphthalene: 4-acetamido-4-isothiocyanato-stilbene-2,2'-disulfonic acid; pyrene-3-sulfonic acid; 2-toluidinonaphthalene-6-sulfonate; N-phenyl, N-methyl 2-aminoaphthalene-6-sulfonate; ethidium bromide; stebrine; auromine-0,2-(9'-anthroyl)palmitate; dansyl phosphatidylethanolamine; N,N'-dioctadecyl oxacarbocyanine; N,N'-dihexyl oxacarbocyanine; merocyanine, 4(3'pyrenyl)butyrate; d-3-aminodesoxy-equilenin; 12-(9'anthroyl)stearate; 2-methylanthracene; 9-vinylanthracene; 2,2'(vinylene-p-phenylene)bisbenzoxazole; p-bis[2-(4-methyl-5phenyl-oxazolyl)]benzene; 6-dimethylamino-1,2-benzophenazin; retinol; bis(3'-aminopyridinium) 1,10-decandiyl diiodide; sulfonaphthylhydrazone of hellibrienin; chlorotetracycline; N-(7-dimethylamino-4-methyl-2-oxo-3-chromenyl)maleimide; N-[p-(2-benzimidazolyl)-phenyl]maleimide; N-(4-fluoranthyl)maleimide; bis(homovanillic acid); resazarin; 4-chloro-7-nitro-2,1,3benzooxadiazole; merocyanine 540; resorufin; rose bengal; and 2,4-diphenyl-3(2H)-furanone.

Desirably, fluorescers should absorb light above about 300 nm, preferably about 350 nm, and more preferably above about 400 nm, usually emitting at wavelengths greater than about 10 nm higher than the wavelength of the light absorbed. It should be noted that the absorption and emission characteristics of the bound dye can differ from the unbound dye. Therefore, when referring to the various wavelength ranges and characteristics of the dyes, it is intended to indicate the dyes as employed and not the dye which is unconjugated and characterized in an arbitrary solvent.

Fluorescers are generally preferred because by irradiating a fluorescer with light, one can obtain a plurality of emissions. Thus, a single label can provide for a plurality of measurable events.

Detectable signal can also be provided by chemiluminescent and bioluminescent sources. Chemiluminescent sources include a compound which becomes electronically excited by a chemical reaction and can then emit light which serves as the detectable signal or donates energy to a fluorescent acceptor. A diverse number of families of compounds have been found to provide chemiluminescence under a variety or conditions. One family of compounds is 2,3-dihydro-1,-4-phthalazinedione. The must popular compound is luminol, which is the 5-amino compound. Other members of the family include the 5-amino-6,7,8-trimethoxy- and the dimethylamino[ca]benz analog. These compounds can be made to luminesce with alkaline hydrogen peroxide or calcium hypochlorite and base. Another family of compounds is the 2,4,5-triphenylimidazoles, with lophine as the common name for the parent product. Chemiluminescent analogs include para-dimethylamino and -methoxy substituents. Chemiluminescence can also be obtained with oxalates, usually oxalyl active esters, e.g., p—nitrophenyl and a peroxide, e.g., hydrogen peroxide, under basic conditions. Alternatively, luciferins can be used in conjunction with luciferase or lucigenins to provide bioluminescence.

Spin labels are provided by reporter molecules with an unpaired electron spin which can be detected by electron spin resonance (ESR) spectroscopy. Exemplary spin labels include organic free radicals, transitional metal complexes, particularly vanadium, copper, iron, and manganese, and the like. Exemplary spin labels include nitroxide free radicals.

B. Scanning System

With the automated detection apparatus, the correlation of specific positional labeling is converted to the presence on the target of sequences for which the oligonucleotides have specificity of interaction. Thus, the positional information is directly converted to a database indicating what sequence interactions have occurred. For example, in a nucleic acid hybridization application, the sequences which have interacted between the substrate matrix and the target molecule can be directly listed from the positional information. The detection system used is described in PCT publication no. WO90/15070; and U.S. Ser. No. 07/624,120. Although the detection described therein is a fluorescence detector, the detector can be replaced by a spectroscopic or other detector. The scanning system can make use of a moving detector relative to a fixed substrate, a fixed detector with a moving substrate, or a combination. Alternatively, mirrors or other apparatus can be used to transfer the signal directly to the detector. See, e.g., U.S. Ser. No. 07/624,120, which is hereby incorporated herein by reference.

The detection method will typically also incorporate some signal processing to determine whether the signal at a particular matrix position is a true positive or may be a spurious signal. For example, a signal from a region which has actual positive signal may tend to spread over and provide a positive signal in an adjacent region which actually should not have one. This may occur, e.g., where the scanning system is not properly discriminating with sufficiently high resolution in its pixel density to separate the two regions. Thus, the signal over the spatial region may be evaluated pixel by pixel to determine the locations and the actual extent of positive signal. A true positive signal should, in theory, show a uniform signal at each pixel location. Thus, processing by plotting number of pixels with actual signal intensity should have a clearly uniform signal intensity. Regions where the signal intensities show a fairly wide dispersion, may be particularly suspect and the scanning system may be programmed to more carefully scan those positions.

More sophisticated signal processing techniques can be applied to the initial determination of whether a positive signal exists or not. See, e.g., U.S. Ser. No. 07/624,120.

From a listing of those sequences which interact, data analysis may be performed on a series of sequences, for example, in a nucleic acid sequence application, each of the sequences may be analyzed for their overlap regions and the original target sequence may be reconstructed from the collection of specific subsequences obtained therein. Other sorts of analyses for different applications may also be performed, and because the scanning system directly interfaces with a computer the information need not be transferred manually. This provides for the ability to handle large amounts of data with very little human intervention. This, of course, provides significant advantages over manual manipulations. Increased throughput and reproducibility is thereby provided by the automation of vast majority of steps in any of these applications.

C Data Analysis

Data analysis will differ depending upon whether sequencing de novo or resequencing is being done, but will typically involve aligning the proper sequences with their overlaps to determine the target sequence or a mutation in the target sequence. Although the target "sequence" may not specifically correspond to any specific molecule, especially where the target sequence is broken and fragmented up in the sequencing process, the sequence corresponds to a contiguous sequence of the subfragments.

The data analysis can be performed manually or, preferably, by a computer using an appropriate program. Although the specific manipulations necessary to reassemble the target sequence from fragments may take many forms, one embodiment uses a sorting program to sort all of the subsequences using a defined hierarchy. The hierarchy need not necessarily correspond to any physical hierarchy, but provides a means to determine, in order, which subfragments have actually been found in the target sequence. In this manner, overlaps can be checked and found directly rather than having to search throughout the entire set after each selection process. For example, where the oligonucleotide probes are 10-mers, the first 9 positions can be sorted. A particular subsequence can be selected as in the examples, to determine where the process starts. As analogous to the theoretical example provided above, the sorting procedure provides the ability to immediately find the position of the subsequence which contains the first 9 positions and can compare whether there exists more than 1 subsequence during the first 9 positions. In fact, the computer can easily generate all of the possible target sequences which contain given combinations of subsequences. Typically, there will be only one, but in various situations, there will be more.

Generally, such computer programs provide for automated scanning of the substrate to determine the positions of oligonucleotide and target interaction. Simple processing of the intensity of the signal may be incorporated to filter out clearly spurious signals. The positions with positive interaction are correlated with the sequence specificity of specific matrix positions, to generate the set of matching subsequences. This information is further correlated with other target sequence information, e.g., restriction fragment analysis. The sequences are then aligned using overlap data, thereby leading to possible corresponding target sequences which will, optimally, correspond to a single target sequence VII. Applications The enzymatic discrimination enhancement methods provided by the present invention have very broad applications. Although described specifically for polynucleotide sequences, similar sequencing, fingerprinting, mapping, and screening procedures may be applied to polypeptide, carbohydrate, or other polymers. Such methods can be used in all instances where improved discrimination between fully complementary hybrids and those that differ by one or more base pairs would be helpful. More particularly, such methods can be used with de novo sequencing, or in conjunction with a second sequencing procedure to provide independent verification (i.e., resequencing). See, e.g., *Science* 242:1245 (1988). For example, a large polynucleotide sequence defined by either the Maxam and Gilbert technique or by the Sanger technique may be verified by using the present invention.

In addition, by selection of appropriate probes, a polynucleotide sequence can be fingerprinted. Fingerprinting is a less detailed sequence analysis which usually involves the characterization or a sequence by a combination of defined features. Sequence fingerprinting is particularly useful because the repertoire of possible features which can be tested is virtually infinite. Moreover, the stringency of matching is also variable depending upon the application. A Southern Blot analysis may be characterized as a means of simple fingerprint analysis.

Fingerprinting analysis may be performed to the resolution of specific nucleotides, or may be used to determine homologies, most commonly for large segments. In particular, an array of oligonucleotide probes of virtually any workable size may be positionally localized on a matrix and used to probe a sequence for either absolute complementary matching, or homology to the desired level of stringency using selected hybridization conditions.

In addition, the present invention provides means for mapping analysis of a target sequence or sequences. Mapping will usually involve the sequential ordering or a plurality of various sequences, or may involve the localization of a particular sequence within a plurality of sequences. This may be achieved by immobilizing particular large segments onto the matrix and probing with a shorter sequence to determine which of the large sequences contain that smaller sequence. Alternatively, relatively shorter probes of known or random sequence may be immobilized to the matrix and a map of various different target sequences may be determined from overlaps. Principles of such an approach are described in some detail by Evans et al. (1989) "Physical Mapping of Complex Genomes by Cosmid Multiplex Analysis," *Proc. Natl. Acad. Sci. USA* 86:5030-5034; Michiels, et al., "Molecular Approaches to Genome Analysis: A Strategy for the Construction of Ordered Overlap Clone Libraries," *CABIOS* 3:203-210 (1987); Olsen, et al. "Random-Clone Strategy for Genomic Restriction Mapping in Yeast," *Proc. Natl. Acad. Sci. USA* 83:7826-7830 (1986); Craig, et al., "Ordering of Cosmid Clones Covering the Herpes Simplex Virus Type I (HSV-I) Genome: A Test Case for Fingerprinting by Hybridization," *Nuc. Acids Res.* 18:2653-2660 (1990); and Coulson, et al., "Toward a Physical Map of the Genome of the Nematode *Caenorhabditis elegans*," *Proc. Natl. Acad. Sci. USA* 83:7821-7825 (1986); each of which is hereby incorporated herein by reference.

Fingerprinting analysis also provides a means of identification. In addition to its value in apprehension of criminals from whom a biological sample, e.g., blood, has been collected, fingerprinting can ensure personal identification for other reasons. For example, it may be useful for identification of bodies in tragedies such as fire, flood, and vehicle crashes. In other cases the identification may be useful in identification of persons suffering from amnesia, or of missing persons. Other forensics applications include establishing the identity of a person, e.g., military identification "dog tags", or may be used in identifying the source of particular biological samples. Fingerprinting technology is described, e.g., in Carrano, et al., "A High-Resolution, Fluorescence-Based, Semi-automated method for DNA Fingerprinting," *Genomics* 4:120-136 (1989), which is hereby incorporated herein by reference.

The fingerprinting analysis may be used to perform various types of genetic screening. For example, a single substrate may be generated with a plurality of screening probes, allowing for the simultaneous genetic screening for a large number of genetic markers. Thus, prenatal or diagnostic screening can be simplified, economized, and made more generally accessible.

In addition to the sequencing, fingerprinting, and mapping applications, the present invention also provide, means for determining specificity of interaction with particular sequences. Many of these applications are described in U.S. Ser. No. 07/362,901 (VLSIPS parent). U.S. Ser. No. 07/492, 462 (VLSIPS CIP), U.S. Ser. No. 07/435,316 (caged biotin parent), and U.S. Ser. No. 07/612,671 (caged biotin CIP), which are incorporated herein by reference.

VIII. Libraries of Unimolecular, Double-Stranded Oligonucleotides

In one aspect, the present invention provides libraries of unimolecular double-stranded oligonucleotides, each member of the library having the formula:

$$Y-L^1-X^1-L^2-X^2$$

in which Y represents a solid support, $X^1$ and $X^2$ represent a pair of complementary oligonucleotides, $L^1$ represents a bond or a spacer, and $L^2$ represents a linking group having sufficient length such that $X^1$ and $X^2$ form a double-stranded oligonucleotide.

The solid support may be biological, nonbiological, organic, inorganic, or a combination of any of these, existing as particles, strands, precipitates, gels, sheets, tubing, spheres, containers, capillaries, pads, slices, films, plates, slides, etc. The solid support is preferably flat but may take on alternative surface configurations. For example, the solid support may contain raised or depressed regions on which synthesis takes place. In some embodiments, the solid support will be chosen to provide appropriate light-absorbing characteristics. For example, the support may be a polymerized Langmuir Blodgett film, functionalized glass, Si, Ge, GaAs, GaP, $SiO_2$, $SiN_4$, modified silicon, or any one of a variety of gels or polymers such as (poly)tetrafluoroethylene, (poly)vinylidenedifluoride, polystyrene, polycarbonate, or combinations thereof. Other suitable solid support materials will be readily apparent to those of skill in the art. Preferably, the surface of the solid support will contain reactive groups, which could be carboxyl, amino, hydroxyl, thiol, or the like. More preferably, the surface will be optically transparent and will have surface Si—OH functionalities, such as are found on silica surfaces.

Attached to the solid support is an optional spacer, $L^1$. The spacer molecules are preferably of sufficient length to permit the double-stranded oligonucleotides in the completed member of the library to interact freely with molecules exposed to the library. The spacer molecules, when present, are typically 6-50 atoms long to provide sufficient exposure for the attached double-stranded DNA molecule. The spacer, $L^1$, is comprised of a surface attaching portion and a longer chain portion. The surface attaching portion is that part of $L^1$ which is directly attached to the solid support. This portion can be attached to the solid support via carbon-carbon bonds using, for example, supports having (poly)trifluorochloroethylene surfaces, or preferably, by siloxane bonds (using, for example, glass or silicon oxide as the solid support). Siloxane bonds with the surface of the support are formed in one embodiment via reactions of surface attaching portions bearing trichlorosilyl or trialkoxysilyl groups. The surface attaching groups will also have a site for attachment of the longer chain portion. For example, groups which are suitable for attachment to a longer chain portion would include amines, hydroxyl, thiol, and carboxyl. Preferred surface attaching portions include aminoalkylsilanes and hydroxyalkylsilanes. In particularly preferred embodiments, the surface attaching portion of $L_1$ is either bis(2-hydroxyethyl)-aminopropyltriethoxysilane, 2-hydroxyethylaminopropyltriethoxysilane, aminopropyltriethoxysilane or hydroxypropyltriethoxysilane.

The longer chain portion can be any of a variety of molecules which are inert to the subsequent conditions for polymer synthesis. These longer chain portions will typically be aryl acetylene, ethylene glycol oligomers containing 2-14 monomer units, diamines, diacids, amino acids, peptides, or combinations thereof. In some embodiments, the longer chain portion is a polynucleotide. The longer chain portion which is to be used as part of $L^1$ can be selected based upon its hydrophilic/hydrophobic properties to improve presentation of the double-stranded oligonucleotides to certain receptors, proteins or drugs. The longer chain portion of $L^1$ can be constructed of polyethyleneglycols, polynucleotides, alkylene, polyalcohol, polyester, polyamine, polyphosphodiester and combinations thereof. Additionally, for use in synthesis of the libraries of the invention, $L^1$ will typically have a protecting group, attached to a functional group (i.e., hydroxyl, amino or carboxylic acid) on the distal or terminal end of the chain portion (opposite the solid support). After deprotection and coupling, the distal end is covalently bound to an oligomer.

Attached to the distal end of $L^1$ is an oligonucleotide, $X^1$, which is a single-stranded DNA or RNA molecule. The oligonucleotides which are part of the present invention are typically of from about 4 to about 100 nucleotides in length. Preferably, $X^1$ is an oligonucleotide which is about 6 to about 30 nucleotides in length. The oligonucleotide is typically linked to $L^1$ via the 3'-hydroxyl group of the oligonucleotide and a functional group on $L^1$ which results in the formation of an ether, ester, carbamate or phosphate ester linkage.

Attached to the distal end of $X^1$ is a linking group, $L^2$, which is flexible and of sufficient length that $X^1$ can effectively hybridize with $X^2$. The length of the linker will typically be a length which is at least the length spanned by two nucleotide monomers, and preferably at least four nucleotide monomers, while not be so long as to interfere with either the pairing of $X^1$ and $X^2$ or any subsequent assays. The linking group itself will typically be an alkylene group (of from about 6 to about 24 carbons in length), a polyethyleneglycol group (of from about 2 to about 24 ethyleneglycol monomers in a linear configuration), a polyalcohol group, a polyamine group (e.g., spermine, spermidine and polymeric derivatives thereof), a polyester group (e.g., poly(ethyl acrylate) having of from 3 to 15 ethyl acrylate monomers in a linear configuration), a polyphosphodiester group, or a polynucleotide (having from about 2 to about 12 nucleic acids). Preferably, the linking group will be a polyethyleneglycol group which is at least a tetraethyleneglycol, and more preferably, from about 1 to 4 hexaethyleneglycols linked in a linear array. For use in synthesis of the compounds of the invention, the linking group will be provided with functional groups which can be suitably protected or activated. The linking group will be covalently attached to each of the complementary oligonucleotides, $X^1$ and $X^2$, by means of an ether, ester, carbamate, phosphate ester or amine linkage. The flexible linking group $L^2$ will be attached to the 5'-hydroxyl of the terminal monomer of $X^1$ and to the 3'-hydroxyl of the initial monomer of $X^2$. Preferred linkages are phosphate ester linkages which can be formed in the same manner as the oligonucleotide linkages which are present in $X^1$ and $X^2$. For example, hexaethyleneglycol can be protected on one terminus with a photolabile protecting group (i.e., NVOC or MeNPOC) and activated on the other terminus with 2-cyanoethyl-N,N-diisopropylamino-chlorophosphite to form a phosphoramidite. This linking group can then be used for construction of the libraries in the same manner as the photolabile-protected, phosphoramidite-activated nucleotides. Alternatively, ester linkages to $X^1$ and $X^2$ can be formed when the $L^2$ has terminal carboxylic acid moieties (using the 5'-hydroxyl of $X^1$ and the 3'-hydroxyl of $X^2$). Other methods of forming ether, carbamate or amine linkages are known to those of skill in the art and particular reagents and references can be found in such texts as March, *Advanced Organic Chemistry*, 4th Ed., Wiley-Interscience, New York, N.Y., 1992, incorporated herein by reference.

The oligonucleotide, $X^2$, which is covalently attached to the distal end of the linking group is, like $X^1$, a single-stranded DNA or RNA molecule. The oligonucleotides which are part of the present invention are typically of from about 4 to about 100 nucleotides in length. Preferably, $X^2$ is an oligonucleotide which is about 6 to about 30 nucleotides in length and exhibits complementarity to $X^1$ of from 90 to 100%. More preferably, $X^1$ and $X^2$ are 100% complementary. In one group of embodiments, either $X^1$ or $X^2$ will further comprise a bulge or loop portion and exhibit complementarity of from 90 to 100% over the remainder of the oligonucleotide.

In a particularly preferred embodiment, the solid support is a silica support, the spacer is a polyethyleneglycol conjugated to an aminoalkylsilane, the linking group is a polyethyleneglycol group, and $X^1$ and $X^2$ are complementary oligonucleotides each comprising of from 6 to 30 nucleic acid monomers.

The library can have virtually any number of different members, and will be limited only by the number or variety of compounds desired to be screened in a given application and by the synthetic capabilities of the practitioner. In one group of embodiments, the library will have from 2 up to 100 members. In other groups of embodiments, the library will have between 100 and 10,000 members, and between 10,000 and 1,000,000 members, preferably on a solid support. In preferred embodiments, the library will have a density of more than 100 members at known locations per cm², preferably more than 1,000 per cm², more preferably more than 10,000 per cm².

Preparation of these libraries can typically be carried out using any of the methods described above for the preparation of oligonucleotides on a solid support (e.g., light-directed methods, flow channel or spotting methods).

IX. Libraries of Conformationally Restricted Probes

In still another aspect, the present invention provides libraries of conformationally-restricted probes. Each of the members of the library comprises a solid support having an optional spacer which is attached to an oligomer of the formula:

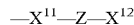

in which $X^{11}$ and $X^{12}$ are complementary oligonucleotides and Z is a probe. The probe will have sufficient length such that $X^{11}$ and $X^{12}$ form a double-stranded DNA portion of each member. $X^{11}$ and $X^{12}$ are as described above for $X^1$ and $X^2$ respectively, except that for the present aspect of the invention, each member of the probe library can have the same $X^{11}$ and the same $X^{12}$, and differ only in the probe portion. In one group of embodiments, $X^{11}$ and $X^{12}$ are either a poly-A oligonucleotide or a poly-T oligonucleotide.

As noted above, each member of the library will typically have a different probe portion. The probes, Z, can be any of a variety of structures for which receptor-probe binding information is sought for conformationally-restricted forms. For example, the probe can be an agonist or antagonist for a cell membrane receptor, a toxin, venom, viral epitope, hormone, peptide, enzyme, cofactor, drug, protein or antibody. In one group of embodiments, the probes are different peptides, each having of from about 4 to about 12 amino acids. Preferably the probes will be linked via polyphosphate diesters, although other linkages are also suitable. For example, the last monomer employed on the $X^{11}$ chain can be a 5'-aminopropyl-functionalized phosphoramidite nucleotide (available from Glen Research, Sterling, Va., USA or Genosys Biotechnologies, The Woodlands, Texas, USA) which will provide a synthesis initiation site for the carboxy to amino synthesis of the peptide probe. Once the peptide probe is formed, a 3'-succinylated nucleoside (from Cruachem, Sterling, Va., USA) will be added under peptide coupling conditions. In yet another group of embodiments, the probes will be oligonucleotides of from 4 to about 30 nucleic acid monomers which will form a DNA or RNA hairpin structure. For use in synthesis, the probes can also have associated functional groups (i.e., hydroxyl, amino, carboxylic acid, anhydride and derivatives thereof) for attaching two positions on the probe to each of the complementary oligonucleotides.

The surface of the solid support is preferably provided with a spacer molecule, although it will be understood that the spacer molecules are not elements of this aspect of the invention. Where present, the spacer molecules will be as described above for $L^1$.

The libraries of conformationally restricted probes can also have virtually any number of members. As above, the number of members will be limited only by design of the particular screening assay for which the library will be used, and by the synthetic capabilities of the practitioner. In one group of embodiments, the library will have from 2 to 100 members. In other groups of embodiments, the library will have between 100 and 10,000 members, and between 10,000 and 1,000,000 members. Also as above, in preferred embodiments, the library will have a density of more than 100 members at known locations per cm², preferably more than 1000 per cm², more preferably more than 10,000 per cm².

Preparation of these libraries can typically be carried out using any of the methods described above for the preparation of oligonucleotides on a solid support (e.g., light-directed methods, flow channel or spotting methods).

X. Libraries of Intermolecular, Doubly-Anchored, Double-Stranded Oligonucleotides In another aspect, the present invention provides libraries of intermolecular, doubly-anchored, double-stranded oligonucleotides, each member of the library having the formula:

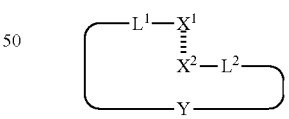

In this formula, Y represents a solid support, $X^1$ and $X^2$ represent a pair of complementary oligonucleotides, and $L^1$ and $L^2$ each represent a bond or a spacer. Typically, $L^1$ and $L^2$ are the same and are spacers having sufficient length such that $X^1$ and $X^2$ can form a double-stranded oligonucleotide. The non-covalent binding which exists between $X^1$ and $X^2$ is represented by the dashed line.

The solid support can be any of the solid supports described herein for other aspects of the invention. Attached to the solid support are spacers, $L^1$ and $L^2$. These spacers are the same as those described above for the unimolecular, double-stranded oligonucleotide Preferably, the spacers are comprised of a surface attaching portion, which is a hydroxyalkyltriethoxysilane or an aminoalkyltriethoxysilane, and a longer chain portion which is derived from a poly(ethylene glycol).

Attached to the distal ends of $L^1$ and $L^2$ are $X^1$ and $X^2$, respectively. $X^1$ and $X^2$ are each a single-stranded DNA or RNA molecule. The oligonucleotides which are part of the present invention are typically of from about 4 to about 100 nucleotides in length. Preferably, $X^1$ and $X^2$ are each an oligonucleotide of about 6 to about 30 nucleotides in length. The oligonucleotides are typically linked to $L^1$ or $L^2$ via the 3'-hydroxyl group of the oligonucleotide and a functional group on $L^1$ which results in the formation of an ether, ester, carbamate or phosphate ester linkage.

In one group of preferred embodiments, $X^1$ and $X^2$ are complementary oligonucleotides of about 6 to about 30 nucleotides in length, and exhibit complementarity of from 90 to 100% over their entire length. Arrays, or libraries of these double-stranded oligonucleotides can be used to screen samples of DNA, RNA, proteins or drugs for their sequence-specific interactions.

In another group of preferred embodiments, the 5'-terminal region of $X^1$ (the distal portion with reference to the solid support) will be complementary to the 5'-terminal region of $X^2$ (the distal portion, again with reference to the solid support). For example, $X^1$ and $X^2$ can each be an oligonucleotide of from about 10 to about 30 nucleotides in length. The 5' end of $X^1$ will comprise of from about 4 to about 20 nucleotides which will be complementary to the 5' end of $X^2$ (see FIG. 10E). As above, the degree of complementarity will typically be from about 90 to about 100%, preferably about 100%. Arrays, or libraries of this group of embodiments can be used for the hybridization and ligation of additional oligonucleotide. With reference to FIGS. 10E and 10F, libraries of oligonucleotides which are complementary in overlapping regions of their 5' ends can be prepared (see FIG. 10E), then incubated with additional oligonucleotides which are complementary to the 3' ends of the surface-bound oligonucleotides. After hybridization, a continuous helix is formed with a length equivalent to the combination of the hybridized added oligonucleotides and the complementary portion of the surface-bound oligonucleotides. Additionally, each strand will contain a nick between the added oligonucleotide and the surface-bound oligonucleotide. In preferred embodiments, the surface-bound oligonucleotides are phosphorylated (chemically or enzymically with a kinase) such that the nick can be closed with a T4 DNA ligase to produce a contiguous intermolecular, doubly-anchored, double-stranded oligonucleotide which is longer than either of the initially formed $X^1$ or $X^2$ oligonucleotides.

Another application for this aspect of the invention is hybridization enhancement. This is illustrated in FIG. 10G. As can be seen in FIG. 10G, a library of intermolecular, doubly-anchored, double-stranded oligonucleotides is prepared as described above and as illustrated in FIG. 10E. Target oligonucleotides, having unknown sequences at their 3' termini incubated with the library. Hybridization of the 3' end of the target oligonucleotide to the complementary portion of a library member is enhanced by the cooperative nature of formation of the extended DNA duplex. Additionally, the hybridization step can be followed by a ligation step (when the ends of the surface-bound oligonucleotides are phosphorylated) to further enhance the discrimination of any 3' mismatches.

The libraries of this aspect of the invention can also have virtually any number of different members, and will be limited only by the number or variety of compounds desired to be screened in a given application and by the synthetic capabilities of the practitioner. In one group of embodiments, the library will have from 2 up to 100 members. In other groups of embodiments, the library will have between 100 and 10,000 members, and between 10,000 and 1,000,000 members, preferably on a solid support. In preferred embodiments, the library will have a density of more than 100 members at known locations per $cm^2$, preferably more than 1,000 per $cm^2$, more preferably more than 10,000 per $cm^2$.

Preparation of these libraries can typically be carried out using any of the methods described above for the preparation of oligonucleotides on a solid support (e.g., light-directed methods, flow channel or spotting methods). Typically, the oligonucleotides $X^1$ and $X^2$ will be synthesized as a pair in each cell of the library. Such synthesis generally requires that synthesis initiation sites be prepared having two different and independently removable protecting groups. For example, a solid support (e.g., a glass coverslip) can be modified with a suitable linking group (e.g., hydroxypropyltriethoxysilane, or the mono triethoxysilylpropyl ether of a polyethylene glycol having an appropriate length). The surface hydroxyl groups which are present following the attachment of the linking groups can be uniformly protected with MeNPOC—Cl. Controlled irradiation can be used to deprotect about half of the hydroxyl groups, which are subsequently protected as DMT or MMT (mono-methoxy trityl)ethers. In this manner, each cell or portion of the solid support will have approximately equivalent numbers of two linking groups bearing independently removable protecting groups. Synthesis of the library can then proceed in a straightforward manner by removing the MeNPOC groups (by irradiation) in one cell and constructing oligonucleotide $X^1$, then removing the DMT or MMT group in the same cell and constructing oligonucleotide $X^2$. Synthesis in each of the cells or regions can proceed in a similar manner to produce the libraries of this aspect of the invention. In this manner, using two rounds of synthesis following the initial steps to divide the available sites into independently protected sites, it is possible to prepare arrays, or libraries of regions containing pair of complementary oligonucleotides of any sequence.

XI. Methods of Screening Libraries of Double-Stranded Oligonucleotides and Probes A library prepared according to any of the methods described above can be used to screen for receptors having high affinity for unimolecular, double-stranded oligonucleotides, intermolecular, doubly-anchored, double-stranded oligonucleotides or conformationally restricted probes. In one group of embodiments, a solution containing a marked (labelled) receptor is introduced to the library and incubated for a suitable period of time. The library is then washed free of unbound receptor and the probes or double-stranded oligonucleotides having high affinity for the receptor are identified by identifying those regions on the surface of the library where markers are located. Suitable markers include, but are not limited to, radiolabels, chromophores, fluorophores, chemiluminescent moieties and transition metals. Alternatively, the presence of receptors may be detected using a variety of other techniques, such as an assay with a labelled enzyme, antibody, and the like. Other techniques using various marker systems for detecting bound receptor will be readily apparent to those skilled in the art.

In a preferred embodiment, a library prepared on a single solid support (using, for example, the VLSIPS™ technique) can be exposed to a solution containing marked receptor such as a marked antibody. The receptor can be marked in any of a variety of ways, but in one embodiment marking is effected with a radioactive label. The marked antibody binds with high affinity to an immobilized antigen previously localized on the surface. After washing the surface free of unbound receptor, the surface is placed proximate to x-ray film or phosphorimagers to identify the antigens that are recognized by the antibody. Alternatively, a fluorescent marker may be provided and detection may be by way of a charge-coupled device (CCD), fluorescence microscopy or laser scanning.

When autoradiography is the detection method used, the marker is a radioactive label, such as $^{32}P$. The marker on the surface is exposed to X-ray film or a phosphorimager, which is developed and read out on a scanner. An exposure time of about 1 hour is typical in one embodiment. Fluorescence detection using a fluorophore label, such as fluorescein, attached to the receptor will usually require shorter exposure times.

Quantitative assays for receptor concentrations can also be performed according to the present invention. In a direct assay method, the surface containing localized probes prepared as described above, is incubated with a solution containing a marked receptor for a suitable period of time. The surface is then washed free of unbound receptor. The amount of marker present at predefined regions of the surface is then measured and can be related to the amount of receptor in solution. Methods and conditions for performing such assays are well-known and are presented in, for example, L. Hood et al., *Immunology*, Benjamin/Cummings (1978), and E. Harlow et al., *Antibodies. A Laboratory Manual*, Cold Spring Harbor Laboratory, (1988). See also, U.S. Pat. No. 4,376,110 for methods of performing sandwich assays. The precise conditions for performing these steps will be apparent to one skilled in the art.

A competitive assay method for two receptors can also be employed using the present invention. Methods of conducting competitive assays are known to those of skill in the art. One such method involves immobilizing conformationally restricted probes on predefined regions of a surface as described above. An unmarked first receptor is then bound to the probes on the surface having a known specific binding affinity for the receptors. A solution containing a marked second receptor is then introduced to the surface and incubated for a suitable time. The surface is then washed free of unbound reagents and the amount of marker remaining on the surface is measured. In another form of competition assay, marked and unmarked receptors can be exposed to the surface simultaneously. The amount of marker remaining on predefined regions of the surface can be related to the amount of unknown receptor in solution. Yet another form of competition assay will utilize two receptors having different labels, for example, two different chromophores.

In other embodiments, in order to detect receptor binding, the double-stranded oligonucleotides which are formed with attached probes or with a flexible linking group will be treated with an intercalating dye, preferably a fluorescent dye. The library can be scanned to establish a background fluorescence. After exposure of the library to a receptor solution, the exposed library will be scanned or illuminated and examined for those areas in which fluorescence has changed. Alternatively, the receptor of interest can be labeled with a fluorescent dye by methods known to those of skill in the art and incubated with the library of probes. The library can then be scanned or illuminated, as above, and examined for areas of fluorescence.

In instances where the libraries are synthesized on beads in a number of containers, the beads are exposed to a receptor of interest. In a preferred embodiment the receptor is fluorescently or radioactively labelled. Thereafter, one or more beads are identified that exhibit significant levels of, for example, fluorescence using one of a variety of techniques. For example, in one embodiment, mechanical separation under a microscope is utilized. The identity of the molecule on the surface of such separated beads is then identified using, for example, NMR, mass spectrometry, PCR amplification and sequencing of the associated DNA, or the like. In another embodiment, automated sorting (i.e., fluorescence activated cell sorting) can be used to separate beads (bearing probes) which bind to receptors from those which do not bind. Typically the beads will be labeled and identified by methods disclosed in Needels, et al., *Proc. Natl. Acad. Sci., USA* 90:10700-10704 (1993), incorporated herein by reference.

The assay methods described above for the libraries of the present invention will have tremendous application in such endeavors as DNA "footprinting" of proteins which bind DNA. Currently, DNA footprinting is conducted using DNase I digestion of double-stranded DNA in the presence of a putative DNA binding protein. Gel analysis of cut and protected DNA fragments then provides a "footprint" of where the protein contacts the DNA. This method is both labor and time intensive. See, Galas et al., *Nucleic Acid Res.* 5:3157 (1978). Using the above methods, a "footprint" could be produced using a single array of unimolecular, double-stranded oligonucleotides in a fraction of the time of conventional methods. Typically, the protein will be labeled with a radioactive or fluorescent species and incubated with a library of unimolecular, double-stranded DNA. Phosphorimaging or fluorescence detection will provide a footprint of those regions on the library where the protein has bound. Alternatively, unlabeled protein can be used. When unlabeled protein is used, the double-stranded oligonucleotides in the library will all be labeled with a marker, typically a fluorescent marker. Incorporation of a marker into each member of the library can be carried out by terminating the oligonucleotide synthesis with a commercially available fluorescing phosphoramidite nucleotide derivative. Following incubation with the unlabeled protein, the library will be treated with DNase I and examined for areas which are protected from cleavage.

The assay methods described above for the libraries of the present invention can also be used in reverse drug discovery. In such an application, a compound having known pharmacological safety or other desired properties (e.g., aspirin) could be screened against a variety of double-stranded oligonucleotides for potential binding. If the compound is shown to bind to a sequence associated with, for example, tumor suppression, the compound can be further examined for efficacy in the related diseases.

In other embodiments, probe arrays comprising β-turn mimetics can be prepared and assayed for activity against a particular receptor, β-turn mimetics are compounds having molecular structures similar to β-turns which are one of the three major components in protein molecular architecture, β-turns are similar in concept to hairpin turns of oligonucleotide strands, and are often critical recognition features for various protein-ligand and protein-protein interactions. As a result, a library of β-turn mimetic probes can provide or suggest new therapeutic agents having a particular affinity for a receptor which will correspond to the affinity exhibited by the β-turn and its receptor.

XII. Bioelectronic Devices and Methods

In another aspect, the present invention provides a method for the bioelectronic detection of sequence-specific oligonucleotide hybridization. A general method and device which is useful in diagnostics in which a biochemical species is attached to the surface of a sensor is described in U.S. Pat. No. 4,562,157 (the Lowe patent), incorporated herein by reference. The present method utilizes arrays of immobilized oligonucleotides (prepared, for example, using VLSIPS™ technology) and the known photo-induced electron transfer which is mediated by a DNA double helix structure. See, Murphy, et al., *Science* 262:1025-1029 (1993). This method is useful in hybridization-based diagnostics, as a replacement for fluorescence-based detection systems. The method of bioelectronic detection also offers higher resolution and potentially higher sensitivity than earlier diagnostic methods involving sequencing/detecting by hybridization. As a result, this method finds applications in genetic mutation screening and primary sequencing of oligonucleotides. The method can also be used for Sequencing By Hybridization (SBH), which is described in co-pending application Ser. Nos. 08/082,937 (filed Jun. 25, 1993) and 08/168,904 (filed Dec. 15, 1993), each of which are incorporated herein by reference for all purposes. This method uses a set of short oligonucleotide probes of defined sequence to search for complementary sequences on a longer target strand of DNA. The hybridization pattern is used to reconstruct the target DNA sequence. Thus, the hybridization analysis of large numbers of probes can be used to sequence long stretches of DNA. In immediate applications of this hybridization methodology, a small number of probes can be used to interrogate local DNA sequence.

In the present inventive method, hybridization is monitored using bioelectronic detection. In this method, the target DNA, or first oligonucleotide, is provided with an electron-donor tag and then incubated with an array of oligonucleotide probes, each of which bears an electron-acceptor tag and occupies a known position on the surface of the array. After hybridization of the first oligonucleotide to the array has occurred, the hybridized array is illuminated to induce an electron transfer reaction in the direction of the surface of the array. The electron transfer reaction is then detected at the location on the surface where hybridization has taken place. Typically, each of the oligonucleotide probes in an array will have an attached electron-acceptor tag located near the surface of the solid support used in preparation of the array. In embodiments in which the arrays are prepared by light-directed methods (i.e, typically 3' to 5' direction), the electron-acceptor tag will be located near the 3' position. The electron-acceptor tag can be attached either to the 3' monomer by methods known to those of skill in the art, or it can be attached to a spacing group between the 3' monomer and the solid support. Such a spacing group will have, in addition to functional groups for attachment to the solid support and the oligonucleotide, a third functional group for attachment of the electron-acceptor tag. The target oligonucleotide will typically have the electron-donor tag attached at the 3' position. Alternatively, the target oligonucleotide can be incubated with the array in the absence of an electron-donor tag. Following incubation, the electron-donor tag can be added in solution. The electron-donor tag will then intercalate into those regions where hybridization has occurred. An electron transfer reaction can then be detected in those regions having a continuous DNA double helix.

The electron-donor tag can be any of a variety of complexes which participate in electron transfer reactions and which can be attached to an oligonucleotide by a means which does not interfere with the electron transfer reaction. In preferred embodiments, the electron-donor tag is a ruthenium (II) complex, more preferably a ruthenium (II) (phen')$_2$(dppz) complex.

The electron-acceptor tag can be any species which, with the electron-donor tag, will participate in an electron transfer reaction. An example of an electron-acceptor tag is a rhodium (10) complex. A preferred electron-acceptor tag is a rhodium (III)(phi)$_2$(phen') complex.

In a particularly preferred embodiment, the electron-donor tag is a ruthenium (II) (phen')$_2$(dppz) complex and the electron-acceptor tag is a rhodium (III) (phi)$_2$(phen') complex.

In still another aspect, the present invention provides a device for the bioelectronic detection of sequence-specific oligonucleotide hybridization. The device will typically consist of a sensor having a surface to which an array of oligonucleotides are attached. The oligonucleotides will be attached in pre-defined areas on the surface of the sensor and have an electron-acceptor tag attached to each oligonucleotide. The electron-acceptor tag will be a tag which is capable of producing an electron transfer signal upon illumination of a hybridized species, when the complementary oligonucleotide bears an electron-donating tag. The signal will be in the direction of the sensor surface and be detected by the sensor.

In a preferred embodiment, the sensor surface will be a silicon-based surface which can sense the electronic signal induced and, if necessary, amplify the signal. The metal contacts on which the probes will be synthesized can be treated with an oxygen plasma prior to synthesis of the probes to enhance the silane adhesion and concentration on the surface. The surface will further comprise a multi-gated field effect transistor, with each gate serving as a sensor and different oligonucleotides attached to each gate. The oligonucleotides will typically be attached to the metal contacts on the sensor surface by means of a spacer group.

The spacer group should not be too long, in order to ensure that the sensing function of the device is easily activated by the binding interaction and subsequent illumination of the "tagged" hybridized oligonucleotides. Preferably, the spacer group is from 3 to 12 atoms in length and will be as described above for the surface modifying portion of the spacer group, $L^1$.

The oligonucleotides which are attached to the spacer group can be formed by any of the solid phase techniques which are known to those of skill in the art. Preferably, the oligonucleotides are formed one base at a time in the direction of the 3' terminus to the 5' terminus by the "light-directed" methods described above. The oligonucleotide can then be modified at the 3' end to attach the electron-acceptor tag. A number of suitable methods of attachment are known. For example, modification with the reagent Aminolink2 (from Applied Biosystems, Inc.) provides a terminal phosphate moiety which is derivatized with an aminohexyl phosphate ester. Coupling of a carboxylic acid, which is present on the electron-acceptor tag, to the amine can then be carried out using HOBT and DCC. Alternatively, synthesis of the oligonucleotide can begin with a suitably derivatized and protected monomer which can then be deprotected and coupled to the electron-acceptor tag once the complete oligonucleotide has been synthesized The silica surface can also be replaced by silicon nitride or oxynitride, or by an oxide of another metal, especially aluminum, titanium (IV) or iron (III). The surface can also be any other film, membrane, insulator or semiconductor overlying the sensor which will not interfere with the detection of electron transfer detection and to which an oligonucleotide can be coupled.

Additionally, detection devices other than an FET can be used. For example, sensors such as bipolar transistors, MOS transistors and the like are also useful for the detection of electron transfer signals.

XIII. Alternative Embodiments

A. Adhesives

In still another aspect, the present invention provides an adhesive comprising a pair of surfaces, each having a plurality of attached oligonucleotides, wherein the single-stranded oligonucleotides on one surface are complementary to the single-stranded oligonucleotides on the other surface. The strength and position/orientation specificity can be controlled using a number of factors including the number and length of oligonucleotides on each surface, the degree of complementarity, and the spatial arrangement of complementary oligonucleotides on the surface. For example, increasing the number and length of the oligonucleotides on each surface will provide a stronger adhesive. Suitable lengths of oligonucleotides are typically from about 10 to about 70 nucleotides. Additionally, the surfaces of oligonucleotides can be prepared such that adhesion occurs in an extremely position-specific manner by a suitable arrangement of complementary oligonucleotides in a specific pattern. Small deviations from the optimum spatial arrangement are energetically unfavorable as many hybridization bonds must be broken and are not reformed in any other relative orientation.

The adhesives of the present invention will find use in numerous applications. Generally, the adhesives are useful for adhering two surfaces to one another. More specifically, the adhesives will find application where biological compatibility of the adhesive is desired. An example of a biological application involves use in surgical procedures where tissues must be held in fixed positions during or following the procedure. In this application, the surfaces of the adhesive will typically be membranes which are compatible with the tissues to which they are attached.

A particular advantage of the adhesives of the present invention is that when they are formed in an orientation specific manner, the adhesive portions will be "self-finding," that is the system will go to the thermodynamic equilibrium in which the two sides are matched in the predetermined, orientation specific manner.

B. Methods For Preparing Single-Stranded Nucleic Acid Sequences

In a further embodiment, the present invention provides a method of using a chip, i.e., an array, of oligonucleotides to direct the synthesis of long, single-stranded nucleic acid sequences. More particularly, the present invention provides a method of directing the synthesis of a single-stranded nucleic acid sequence, the method comprising: (a) forming a hybrid complex by combining at least two oligonucleotides which are phosphorylated at their 5' ends with a chip-bound oligonucleotide, the chip-bound oligonucleotide having subsequences which are complementary to a subsequence of each of the oligonucleotides; (b) contacting the hybrid complex with a ligase to form a ligated oligonucleotide; and (c) releasing the ligated oligonucleotide from the chip-bound oligonucleotide to form a single-stranded nucleic acid sequence.

Figure 17A:
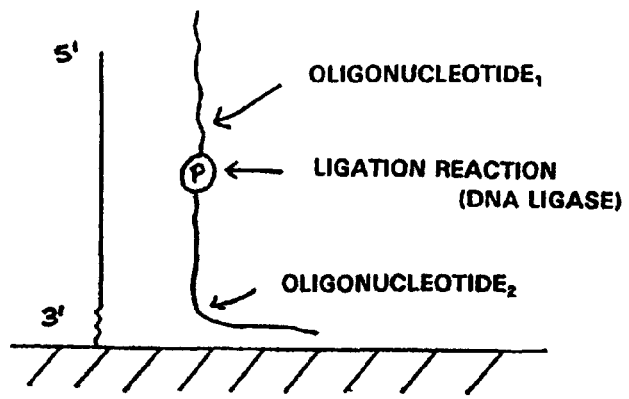
FIG. 17A to 17C illustrate methods which can be used to prepare single-stranded nucleic acid sequences.

The foregoing method is illustrated in FIG. 17A. As shown in FIG. 17A, the joining of Oligo 1 ($O_1$) and Oligo 2 ($O_2$) is directed by a chip-bound oligonucleotide having subsequences which are complementary to the ends of $O_1$ and $O_2$. The oligonucleotides, e.g., $O_1$ and $O_2$, are typically greater than 20 nucleotides in length and they are phosphorylated at their 5' ends. Any enzyme that catalyzes the formation of a phosphodiester bond at the site of a single-strand break in duplex DNA can be used in this method of the present invention. Such ligases include, but are not limited to, T4 DNA ligase, ligases isolated from *E. coli* and ligases isolated from other bacteriophages. In a presently preferred embodiment, T4 DNA ligase is the ligase used. The concentration of the ligase will vary depending on the particular ligase used, the concentration of oligonucleotides and buffer conditions, but will typically range from about 500 units/ml to about 5,000 units/ml. Moreover, the time in which the hybrid complex is in contact with the ligase will vary. Typically, the ligase treatment is carried out for a period of time ranging from minutes to hundreds of hours.

Figure 17B:
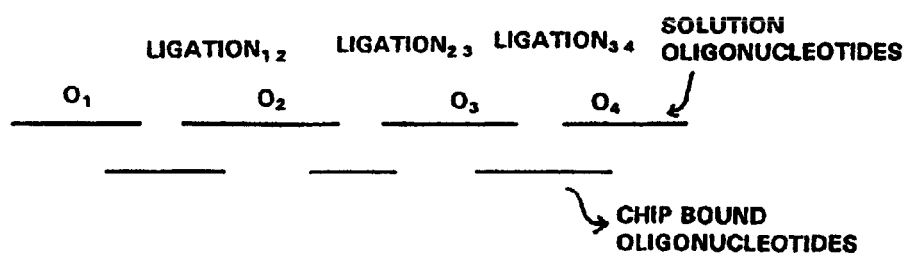

It will be readily apparent to those of skill in the art that using the method of the present invention, multiple oligonucleotides, e.g., Oligos $O_1$-$O_4$, can be joined together by a series of ligation reactions directed by the chip-bound oligonucleotides (See, e.g., FIG. 17B). After each ligation step, the temperature needs to be raised and/or the salt concentration reduced to allow the ligated oligonucleotide to be released from the surface. Many cycles of hybridization, ligation and heating will be necessary for complete synthesis. However, only a small amount of the full-length product needs to be synthesized as it can be amplified using PCR subsequent to the ligation steps.

Moreover, it will be readily apparent to those of skill in the art that the chip can consist of a wide variety of oligonucleotides that would allow a large number of different single-stranded nucleic acid sequences to be constructed. The chip can have virtually any number of different oligonucleotides, and will be limited only by the number or variety of single-stranded nucleic acid sequences desired and by the synthetic capabilities of the practitioner. In one group of embodiments, the chip will have from 1 up to 100 members. In other groups of embodiments, the chip will have between 100 and 1,0000 members, and between 10,000 and 1000000 members. In preferred embodiments, the chip will have a density of more than 100 members at known locations per $cm^2$, preferably more than 1,000 per $cm^2$, more preferably more than 10,000 per $cm^2$. In addition to the foregoing, site-directed "mutant" sequences can be made by using "mutated" $O_i$ oligonucleotides. If the mutation is at an internal position of $O_i$, the same chip-bound oligonucleotides are appropriate for the ligation steps. If, however, the mutation is near a junction, different chip-bound oligonucleotides will be required. The chip can consist of a wide variety of oligonucleotides that would allow a large number of different sequences to be constructed. Moreover, shuffled genes ($O_i$ in a different order) can also be made using a different chip that encodes for a different set of junctions. In addition, a family of mutant genes can be made by using pools of oligonucleotides in solution and a chip that contains templates for all possible, correctly ordered junctions.

Figure 17C:
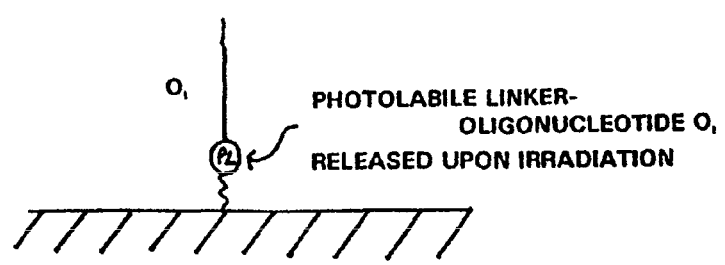

In another embodiment, the oligonucleotides, i.e., $O_i$, can be synthesized on a chip and selectively released into solution. This embodiment can be carried out using a photo-labile linker (See, FIG. 17C). Any gene or mutant gene can be synthesized by selectively releasing the desired oligonucleotides into solution prior to the series of ligation reactions. This would provide an incredibly diverse mutant-generation capacity, with the specific synthetic produces) determined by the irradiation steps used to release the specific set of oligos (and the junctions encoded by the chip). A mutant sequence or, alternatively, a family of mutant sequences could be simply selected by the choice of photolysis steps that produce the desired reactant oligos. In this embodiment, it is best if the photolysis wavelength of the photolabile linker is different from the wavelength used to remove the MENPOC group during synthesis. Moreover, the photolysis wavelength must also be compatible with phosphoramidite synthesis steps. Such photolabile linkers include, but are not limited to, ortho-nitrobenzyl groups and derivatives thereof.

XIV. EXAMPLES

The following examples are provided to illustrate the efficacy of the inventions herein.

A. Enhanced discrimination using RNase A

This example illustrates the ability of RNase A to recognize and cut single-stranded RNA, including RNA in DNA:RNA hybrids that is not in a perfect double-stranded structure. RNA bulges, loops, and even single base mismatches can, for example, be recognized and cleaved by RNase A. RNase A treatment is used herein to improve the quality of RNA hybridization signals on high density oligonucleotide arrays.

Example I

The high density array of oligonucleotide probes on a glass substrate (referred to as a "chip") is prepared using the standard VLSIPS protocols set forth above. Moreover, the pattern of oligonucleotide probes is based on the standard tiling strategy described shown in FIG. 5. Briefly, the chip used in this example consists of an overlapping set of DNA 15-mers covalently linked to a glass surface. A set of four probes for each nucleotide of a 1.3 kb region spanning the D-loop region of human mitochondrial DNA (mtDNA) is present on the substrate. Each of the four probes contains a different base (A, C, G or T) at the position being interrogated, with the substitution position being near the center of the probe. Because the probes are specifically selected based on the mtDNA target sequence, one of the four probes will be perfectly complementary to the mtDNA target, and the other three will contain a central base-pairing mismatch. The mismatch probes are expected to hybridize to a lesser extent. By incorporating fluorophores into the target DNA or RNA, the extent of hybridization at the four positions for each base can be quantitated using fluorescence imaging. In principle, the correct target base is simply identified as the complement to the probe base giving rise to the largest hybridization signal.

Generally, a "base identification" is considered to be made if the signal in one of the four probe regions is greater than twice as large as the signal in a nearby region that contains no oligonucleotide probes (referred to herein as the "background"), and if the signal is at least 1.2 times as large as in the other three related probe regions on the chip. If the signal in more than one of the probe regions is larger than twice the background, but is not greater than the other three by at least a factor of 1.2, then a "multiple-base ambiguity" is indicated. For example, if the T-containing and the C-containing probes have high but similar hybridization signals, a two-base ambiguity would result (a call of either the complementary bases A or G could be made). All two-base ambiguities are possible, as well as all 3- and 4-base ambiguities. If the most intense hybridization signal (largest by at least a factor of 1.2) is in the region that is not complementary to the target sequence, then an "incorrect call" is made (referred to herein as a "miscall"). As shown below, the RNase A treatment resolves multiple-base ambiguities and reduces the number of miscalls that result from hybridization of a 1.3 kb RNA target to the mitochondrial probe chip described above.

Figure 6:
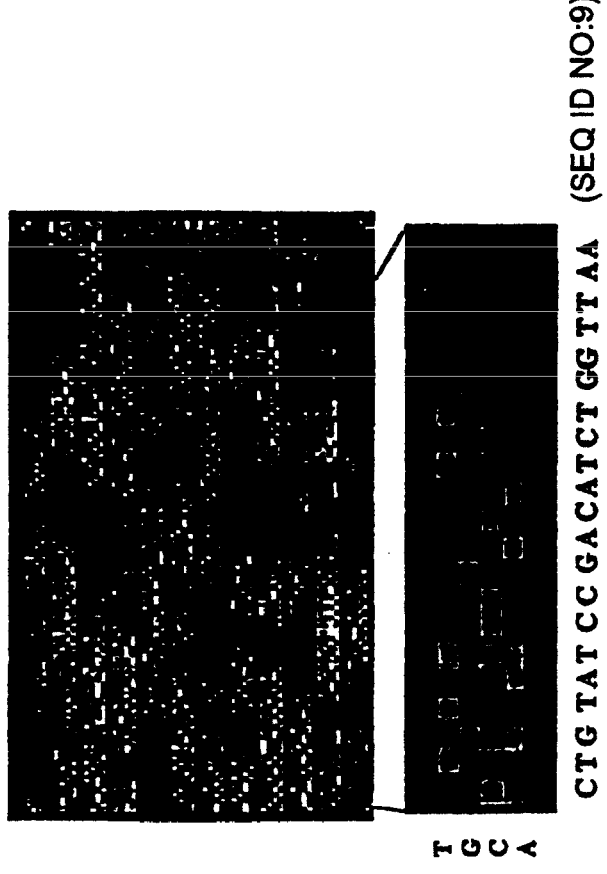
FIG. 6 illustrates the results obtained from hybridization to the substrate without RNase treatment.
Figure 7:
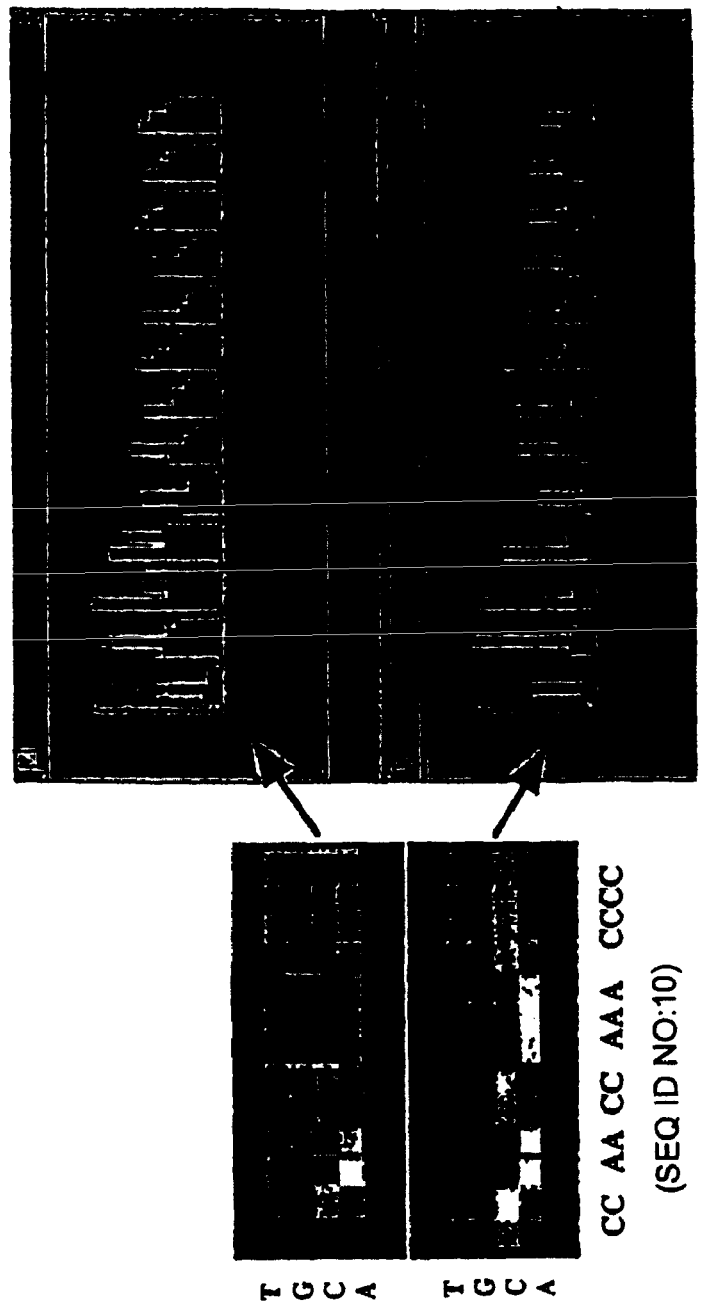
FIG. 7 illustrates the results obtained from hybridization to the substrate with RNase treatment.

Labelled mitochondrial RNA samples are prepared using standard PCR and in vitro transcription procedures. The 1.3 kb RNA sample is labelled by incorporation of fluorescein-labelled UTP during transcription (approximately 10% of Us in the RNA sample are labelled). The RNA (approximately 200 nM concentration of 1.3 kb transcripts) is partially fragmented by heating to 99.9° C. for 60 minutes in 6 mM magnesium chloride, pH 8. This procedure produces a wide range of fragment lengths, with an average length of approximately 200 nucleotides. After fragmentation, the RNA sample is diluted to 10 nM in 60 mM sodium phosphate, 0.9 M NaCl, 6 mM EDTA, 0.05% Triton X-100, pH 7.9 (referred to as 6×SSPE-T). For hybridization, 10 mM CTAB (cetyltrimethylammonium bromide) is added. The RNA sample is hybridized to the chip in a 1 ml flow cell at 22° C. for 40 minutes with stirring provided by bubbling nitrogen gas through the flow cell. Following hybridization, the chip is rinsed with 6×SSPE-T and the fluorescence signal is detected using a scanning confocal fluorescence microscope ("reading" the chip) (See, FIG. 6). The image is stored for later analysis. The chip is then treated with 75 µl of 0.2 µg/ml RNase A in 6×SSPE-T at 22° C. for intervals of 10, 45, and 75 minutes. After each interval, the chip is rinsed with 6×SSPE-T and the fluorescence signal is read (See, FIG. 7). The results are analyzed to determine the number of correct base calls, multiple-base ambiguities and miscalls, and the improvement resulting from the RNase A treatments.

After the original hybridization, 619 out of 1302 bases were called correctly (approximately 47%). Of the remaining, there were 218 miscalls, 458 multiple-base ambiguities, and 17 instances where the signal was not more than twice the background. (These numbers are subject to the conditions of the experiment.) In particular, they are a function of hybridization time and temperature, salt concentration, the presence of Triton X-100 and CTAB, and the extent of RNA fragmentation and labelling. The conditions used here, in particular the limited fragmentation of the RNA, are ones that tend to decrease the number of regions with low signal, and to increase the number of miscalls and ambiguities.) Following treatment with RNase A (and combining the information for the three time points), 162 out of 218 miscalls were corrected, and 350 out of 458 ambiguities were correctly resolved. There were only 46 bases that were initially ambiguous which were resolved incorrectly, and there were no instances of correct calls that were changed to incorrect calls after RNase A treatment. After the initial hybridization, only 47%, of the entire sequence was called correctly. However, when the hybridization results are combined with the results following RNase A treatment, approximately 87% of the 1302 bases are called correctly. These results clearly demonstrate that RNase A is very effective in improving the quality of the sequence information obtained from hybridization to oligonucleotide arrays.

B. Enhanced Discrimination Using Ligation Reactions

The following examples illustrate the ability of ligation reactions to improve discrimination of base-pair mismatches near the 5' end of an oligonucleotide probe. The ligation reaction of labelled, short oligonucleotides to the 5' end of oligonucleotide probes on a chip should occur (in the presence of the enzyme Ligase) wherever a probe:target hybrid has formed with correct base-pairing near the 5' end of the probe and where there is a suitable 3' overhang of the target to serve as a template for hybridization and ligation. In the following examples, the ligation reaction is used to improve discrimination of base-pair mismatches near the 5' end of the probe, i.e., mismatches which are often poorly discriminated following hybridization alone.

Example I

In this example, a chip is made with probes having the following sequence:

P-P-A-A-CGCGCCGCNC-5'    (SEQ ID NO: 33)

wherein: P is a polyethlyeneglycol (PEG) spacer, A, C, and G, are the usual deoxynucleotides, and N is either A, C, G, or T. The chip is made using the standard VLSIPS protocols set forth above. The target oligonucleotide is a 20-mer having the following sequence (listed 5' to 3'):

F1-GCGCGGCGCGAACGCAACGC    (SEQ ID NO: 34)

wherein: Fl is a fluorescein molecule covalently attached at the 5' end. The labelled, ligatable 6-mer used in this example has the following sequence:

F1-TGCGTT.

The 5' half of the 20-mer target is complementary to the probes on the chip for which N is a G. The probe:target hybrids for the other three probes have a single base mismatch one base in from the 5' end of the probe. The ligatable 6-mer is complementary to the 3' overhang of the > target when the target is hybridized to the probe to form the maximum number of Watson-Crick hydrogen bonds.

Prior to hybridization and ligation, the chip is treated with T4 Polynucleotide Kinase in order to phosphorylate the 5' end of the probes. The probes are phosphorylated using 100 units of T4 Polynucleotide Kinase (New England Biolabs) in 1 ml at 37° C. for 90 minutes.

A 10 nM solution of the target oligo in 6×SSP-T (no EDTA in the hybridization buffer because EDTA could interfere with subsequent ligation reactions) is hybridized to the chip for 30 minutes at 22° C. The chip is scanned, and then washed with a large amount of water to remove the labelled target molecules.

The ligation reaction is carried out at 16° C. in a 1 ml flow cell containing 10 nM target oligo, 20 nM ligatable 6-mer, and 4000 units of T4 DNA Ligase (New England Biolabs). The buffer is the buffer recommended by the manufacturer plus 150 mM NaCl. The reaction is allowed to proceed for 14 hours at 16° C., after which the chip is vigorously washed with water at 50° C. to remove the labelled target molecules. The only fluorescent label remaining after washing is that of the ligatable 6-mers that have been covalently attached to the probes via the ligation reaction. The chip is scanned and analyzed, and the results compared to those obtained from the hybridization reaction above.

| N   | HYB | HDF | LIG | LDF |
|-----|-----|-----|-----|-----|
| A   | 143 | 1.1 | 15  | 5.5 |
| C   | 134 | 1.1 | 13  | 6.3 |
| G** | 151 | 1.0 | 82  | 1.0 |
| T   | 110 | 1.4 | 20  | 4.1 |

In the above table, N is the base in the probe that is one position in from the 5' end (see, supra). For the target used here, G is the complementary base. HYB and LIG are the signals (fluorescence counts) for the different probes following hybridization and ligation, respectively. HDF and LDF are the discrimination factors (defined as the ratio of the fluorescence signal with the perfect match, G, to the signal with the specified mismatch base) following hybridization and ligation, respectively.

It is clear that after hybridization, the extent of target hybridization is very similar for the perfectly complementary probe and the probes containing a mismatch near the 5' end. The A and C mismatches differ by only 10%, and the maximum difference is only 40%. In contrast, following the ligation reaction, the discrimination is greatly improved, with the minimum discrimination factor greater than 4. These data indicate that ligation reactions can be performed on covalently attached oligonucleotide probes on the chip surface, that these reactions are specific for correctly base-paired probe:target hybrids, and that the reaction can be used to improve the discrimination between perfect matches and single base mismatches.

Example II

In this example, a chip was made with probes having the following sequences:

P-P-A-A-CGCGCATTCN-5'    (SEQ ID NO: 35)
                         (denoted CG)

P-P-A-A-ATATAATTCN-5'    (SEQ ID NO: 36)
                         (denoted AT)

A, T, C, G and N have the same definitions as those set forth in Example I, supra. These probes contain a perfect match and the single-base mismatch sequences for the following 22-mer target oligos (listed 5' to 30:

F1-GCGCGTAAGGCCTTCGACGTAG    (SEQ ID NO: 37)
                             (denoted OH1)

F1-TATATTAAGGCCTTCGACGTAG    (SEQ ID NO: 38)
                             (denoted OH2)

The 5' end of OH1 is complementary to the CG probes with N=C, and the 5' end of OH2 is complementary to the AT probes with N=C. Both OH1 and OH2 have the same 12-mer sequence at the 3' end. The labelled, ligatable 6-mer used in this example (appropriate for both OH1 and OH2 when hybridized to the CG and AT regions of the chip, respectively) has the following sequence:

F1-CGAAGG (denoted L6B).

Prior to hybridization and ligation, the chip is phosphorylated as in Example I, supra, using T4 polynucleotide kinase for 4 hours at 37° C. The hybridization and ligation conditions are the same as those used in Example I unless otherwise specified. In particular, 2000 units of T4 DNA Ligase are used for the reaction here, and the concentration of the ligatable 6-mer is 10 nM rather than 20 nM.

The hybrids between OH1 and the CG probes on the chip contain a high proportion of C-G base pairs. C-G base pairs are known to be considerably more stable than the A-T base pairs that are predominant in the hybrid between OH2 and the AT probes on the chip. Thus, it is expected that OH1 will hybridize to its perfectly complimentary probe oligo to a greater extent than will OH2 under suitably stringent hybridization conditions. In fact, this is observed to be the case in the hybridization experiments below. The ligation reaction, however, can be used to help mitigate the complicating effects of the base composition dependence of hybridization.

The chip was initially hybridized with both OH1 and OH2 at 22° C. for 30 minutes. The extent of hybridization to both the CG and AT regions of the chip is analyzed. It is found that the fluorescence signal in the CG regions (OH1 hybrids) is larger than in the AT regions (OH2 hybrids) by more than a factor of 14. In fact, the perfect match signal in the CG region is quite strong, but the signal in the AT region is only slightly greater than twice the background.

|   | (OH1) | | (OH2) | |
|---|---|---|---|---|
| N | HYB | HDF | HYB* | HDF* |
| A | 196 | 2.4 | 6 | 5.5 |
| C** | <u>474</u> | 1.0 | <u>33</u> | 1.0 |
| G | 159 | 3.0 | 20 | 1.7 |
| T | 103 | 4.6 | 5 | 6.6 |

*These values are somewhat uncertain because the signal is not large relative to the background.

Following hybridization, the chip was washed extensively with water to remove the target molecules. A ligation reaction is initiated on the chip by combining OH1, OH2, and L6B in 1 ml of ligation buffer and adding 2000 units of T4 DNA Ligase. The reaction is allowed to proceed for 34 hours at 22° C., and then for another 24 hours at 8° C. At each stage, the chip is read and the data recorded and analyzed.

|   | 34 hrs., T = 22° C. | | | | 24 hrs., T = 8° C. | | | |
|---|---|---|---|---|---|---|---|---|
|   | (OH1) | | (OH2) | | (OH1) | | (OH2) | |
| N | LIG | LDF | LIG | LDF | LIG | LDF | LIG | LDF |
| A | 18 | 56 | 3 | 31 | 27 | 46 | 10 | 88 |
| C | <u>1003</u> | 1.0 | 92 | 1.0 | <u>1234</u> | 1.0 | <u>879</u> | 1.0 |
| G | 13 | 44 | 23 | 13 | 24 | 51 | 30 | 29 |
| T | 15 | 67 | 3 | 31 | 22 | 56 | 8 | 110 |

It is striking that after the ligation reaction at 8° C., the signals for OH1 and OH2 differ by only a factor of 1.4, ten times less than the factor of 14 that was observed following the original hybridization. It is even more striking that the composition dependence is mitigated by virtue of the ligation reaction at low temperature with no loss of discrimination for either OH1 or OH2.

Example III

In order for the ligation strategy to be useful for unknown or more complex DNA targets, it is necessary to use a pool of all possible (4096) 6-mers instead of a specific ligatable 6-mer. The 4096 6-mers are synthesized using standard phosphoramidite chemical procedures on four separate columns, one beginning (at the 3' end) with A, one with C, one with G, and one with T. Each of the 5 subsequent synthesis steps are performed using a mixture of A, C, G, and T phosphoramidite, producing a mixture of all possible five base sequences on each of the four columns. The 6-mers are labelled with fluorescein at the 5' end as the last step in the synthesis. After reversed-phase HPLC purification of the four 6-mer pools, the concentration of each pool is determined by the absorption at 260 nm. The appropriate amounts of each pool is mixed to make a solution that contains all 4096 labelled 6-mer oligonucleotides.

A chip is made containing 10-mer probes having the following sequences

P-P-C-G-C-G-$N_1$-$N_2$-$N_3$-$N_4$-$N_5$-$N_6$-5' (SEQ ID NO: 39)

wherein: $N_i$ are A, C, G, or T. In other words, the chip contains 10-mers with all possible (4096) six base combinations at the 5' end. The 5' phosphate group on the probes required for ligation is added chemically (using 5' Phosphate-ON, Clontech Laboratories, Palo Alto, Calif.) as the last step in the synthesis of the chip, prior to deprotection of the bases. The target oligo is a 22-mer having the following sequence (listed 5' to 3*):

(SEQ ID NO: 37)
F1-GCGCGTAAGGCCTTCGACGTAG (OH1)

The chip was initially hybridized with 10 nM OH1 in 6×SSP-T at 22° C. for 30 minutes. The chip is read and analyzed. The only perfect match probe for this target (i.e., PP-CGCGCATTCC-5' (SEQ ID NO: 40)) has the second highest hybridization signal. Eight other probes have hybridization signals that are within a factor of 4 of the perfect match signal. The other three probes with a single base mismatch at the 5' end have discrimination factors of 2.0, 2.6, and 3.5, for G, A, and T, respectively. Other single base mismatches at positions in from the 5' end of the probe give signals that are considerably smaller. The chip is washed with water to remove the hybridized target.

The chip is next hybridized using the conditions used for the ligation reaction. The chip is hybridized with 10 nM OH1 and 1.6 μM 6-mer pool (0.4 nM for each 6-mer oligo) in the ligation buffer for 11 hours at 22° C. (no ligase at this stage). The perfect match probe gives the highest signal by a factor of 2.4. Five probes have signals within a factor of 4 of the perfect match signal. The other three probes with a single base mismatch at the 5' end have discrimination factors of 3.0, 3.6, and 8.0, for G, A, and T, respectively.

The ligation reaction is initiated by the addition of 2000 units of T4 DNA ligase to the solution containing OH1 and the pool of 6-mers. The reaction is allowed to proceed for 23 hours at 22° C. After washing the chip with water at about 45° C. for five minutes, the chip is read. After ligation, no other probes have hybridization signals that are within a factor of 4 of the perfect match signal. The three 5' single base mismatch probes all have discrimination factors greater than 12. Thus, with a complex chip containing 4096 probes with all possible 6-mer sequences at the 5' end, and using a pool of all possible ligatable 6-mers, the ligation reaction is still specific for the perfectly complementary probe and affords considerable increases in the discrimination between perfect matches and single-base mismatches.

Example IV

In this example, a chip was made using the tiling strategy (A, C, G, T-containing probes for each base in the sequence) described above that covers a 50 base region of the protease gene of HIV-1 (SF2 strain). The probes are 11-mers, linked to the glass support by three PEG linkers. The substitution position (the position being interrogated by an A, C, G, or T base in the probe) is varied between the 5' end of the probe, and five bases in from the 5' end (referred to as positions end, -1, -2, -3, -4 and -5). The chip is synthesized using standard VLSIPS protocols. Prior to hybridization and ligation, the chip is phosphorylated using T4 polynucleotide kinase for 5 hours at 37° C. The target is a 75-mer oligonucleotide (denoted Hpro1), labelled at the 5' end with fluorescein, that spans the complementary 50 base region on the chip.

The chip was initially hybridized with a 10 nM solution of Hpro1 in 6×SSP-T at 22° C. for 30 minutes. After hybridization, the chip was read, and then rinsed with water to remove the target molecules. A ligation reaction was then carried out with 10 nM Hpro1, 1.6 μM 6-mer pool (0.4 nM per oligo), and 2000 units of T4 DNA Ligase in 1 ml of ligation buffer. The ligation reaction is allowed to proceed for 25 hours at 8° C., then 90 hours at 22° C., and finally 4 days at 8° C. At intervals of 1 to 2 days, the solution is supplemented with additional T4 DNA Ligase. Following the ligation reaction, the chip is washed vigorously with water at about 45° C. for 10 minutes, leaving only the labelled 6-mers that have been ligated to the probe molecules. The chip is read, and the data analyzed.

The results of the hybridization and ligation reactions are analyzed in terms of the ability to make a correct base call from the fluorescence signal measured on the chip. In particular, the signal is compared between the four probes that differ by a single base at a given position within the 11-mer, with the rest of the 11-mer being perfectly complementary to a specific region of the target sequence. For the purposes of this experiment, a base identification is said to be made if the signal in at least one of the four probe regions is greater than the signal in a nearby region that has no oligonucleotide probes (the background) by at least 5 counts (the background counts are usually about 2-6 counts), and if the signal in one of the four regions is greater than that in the other three related regions by at least a factor of 1.2. If none of the four signals are larger than the other three by a factor of at least 1.2, a multiple base ambiguity results. If the most intense hybridization signal (by a factor of at least 1.2) is for a probe that is not perfectly complementary to the target sequence, then a miscall results.

Following hybridization, the 11-mer probes with substitution positions-1, -2, -3, and -4 all gave 49 correct base calls and 1 multiple base ambiguity. The probe with substitution position -5 resulted in 50 correct base calls. Following ligation, the probes with substitution positions-2 and -5 gave 48 correct calls and 2 miscalls, substitution position-3 yielded 48 correct calls and 1 ambiguity and 1 miscall, and substitution position-1 and -4 both yielded 50 correct calls with no ambiguities or miscalls. These results indicate that the ligation reaction with the full pool of 6-mers can be used to specifically label hybrids between relatively complex targets and arrays of oligonucleotide probes.

It is interesting to note that the pattern of ligation (stronger or weaker signals, better or worse discrimination) is not in general the same as the pattern of hybridization. This suggests that these two approaches may be used as complementary tools to obtain sequence information with arrays of oligonucleotide probes. For example, probes that produce large hybridization signals, but are poorly discriminated may be better treated using a ligation step. And probes that do not hybridize well to a particular complementary target (leading to a signal that is too small relative to the background) may ligate well enough to be clearly detected (as also suggested by the mitigation of the base composition dependence demonstrated in Example II, supra).

C. Preparation of Unimolecular, Double-Stranded Oligonucleotides

Example I

This example illustrates the general synthesis of an array of unimolecular, double-stranded oligonucleotides on a solid support.

Unimolecular double stranded DNA molecules were synthesized on a solid support using standard light-directed methods (VLSIPS™ protocols). Two hexaethylene glycol (PEG) linkers were used to covalently attach the synthesized oligonucleotides to the derivatized glass surface. Synthesis of the first (inner) strand proceeded one nucleotide at a time using repeated cycles of photo-deprotection and chemical coupling of protected nucleotides. The nucleotides each had a protecting group on the base portion of the monomer as well as a photolabile MeNPoc protecting group on the 5' hydroxyl. Upon completion of the inner strand, another MeNPoc-protected PEG linker was covalently attached to the 5' end of the surface-bound oligonucleotide. After addition of the internal PEG linker, the PEG is photodeprotected, and the synthesis of the second strand proceeded in the normal fashion. Following the synthesis cycles, the DNA bases were deprotected using standard protocols. The sequence of the second (outer) strand, being complementary to that of the inner strand, provided molecules with short, hydrogen bonded, unimolecular double-stranded structure as a result of the presence of the internal flexible PEG linker.

An array of 16 different molecules were synthesized on a derivatized glass slide in order to determine whether short, unimolecular DNA structures could be formed on a surface and whether they could adopt structures that are recognized by proteins. Each of the 16 different molecular species occupies a different physical region on the glass surface so that there is a one-to-one correspondence between molecular identity and physical location. The molecules are of the form

S-P-P-C-C-A/T-A/T-A/T-A/T-G-C-P-G-C-A/T-A/T-A/T-A/T-G-G-F where S is the solid surface having silyl groups, P is a PEG linker, A, C, G, and T are the DNA nucleotides, and F is a fluorescent tag. The DNA sequence is listed from the 3' to the 5' end (the 3' end of the DNA molecule is attached to the solid surface via a silyl group and 2 PEG linkers). The sixteen molecules synthesized on the solid support differed in the various permutations of A and T in the above formula.

Example II

This example illustrates the ability of a library of surface-bound, unimolecular, double-stranded oligonucleotides to exist in duplex form and to be recognized and bound by a protein.

A library of 16 different members was prepared as described in Example 1. The 16 j molecules all have the same composition (same number of As, Cs, Gs and Ts), but the order is different Four of the molecules have an outer strand that is 100% complementary to the inner strand (these molecules will be referred to as DS, double-stranded, below). One of the four DS oligonucleotides has a sequence that is recognized by the restriction enzyme EcoR1. If the molecule can loop back and form a DNA duplex, it should be recognized and cut by the restriction enzyme, thereby releasing the fluorescent tag. Thus, the action of the enzyme provided a functional test for DNA structure, and also served to demonstrate that these structures can be recognized at the surface by proteins. The remaining 12 molecules had outer strands that were not complementary to their inner strands (referred to as SS, single-stranded, 1 below). Of these, three had an outer strand and three had an inner strand whose sequence was an EcoR1 half-site (the sequence on one strand was correct for the enzyme, but the other half was not). The solid support with an array of molecules on the surface is referred to as a "chip" for the purposes of the following discussion. The presence of fluorescently labelled molecules on the chip was detected using confocal fluorescence microscopy. The action of various enzymes was determined by monitoring the change in the amount of fluorescence from the molecules on the chip surface (e.g. "reading" the chip) upon treatment with enzymes that can cut the DNA and release the fluorescent tag at the 5' end.

The three different enzymes used to characterize the structure of the molecules on the chip were:
1) Mung Bean Nuclease—sequence independent, single-strand specific DNA endonuclease;
2) DNase 1—sequence independent, double-strand specific endonuclease;

3) EcoR1—restriction endonuclease that recognizes the sequence (5'-3')
GAATTC in double stranded DNA, and cuts between the G and the first A. Mung Bean Nuclease and EcoR1 were obtained from New England Biolabs, and DNase I was obtained from Boehringer Mannheim. All enzymes were used at a concentration of 200 units per mL in the buffer recommended by the manufacturer. The enzymatic reactions were performed in a 1 mL flow cell at 22° C., and were typically allowed to proceed for 90 minutes.

Upon treatment of the chip with the enzyme EcoR1, the fluorescence signal in the DS EcoR1 region and the 3 SS regions with the EcoR1 half-site on the outer strand was reduced by about 10% of its initial value. This reduction was at least 5 times greater than for the other regions of the chip, indicating that the action of the enzyme is sequence specific on the chip. It was not possible to determine if the factor is greater than 5 in these preliminary experiments because of uncertainty in the constancy of the fluorescence background. However, because the purpose of these early experiments was to determine whether unimolecular double-stranded structures could be formed and whether they could be specifically recognized by proteins (and not to provide a quantitative measure of enzyme specificity), qualitative differences between the different synthesis regions were sufficient.

The reduction in signal in the 3 SS regions with the EcoR1 half-site on the outer strand indicated either that the enzyme cuts single-stranded DNA with a particular sequence, or that these molecules formed a double-stranded structure that was recognized by the enzyme. The molecules on the chip surface were at a relatively high density, with an average spacing of approximately 100 angstroms. Thus, it was possible for the outer strand of one molecule to form a double-stranded structure with the outer strand of a neighboring molecule. In the case of the 3 SS regions with the EcoR1 half-site on the outer strand, such a bimolecular double-stranded region would have the correct sequence and structure to be recognized by EcoR1. However, it would differ from the unimolecular double-stranded molecules in that the inner strand remains single-stranded and thus amenable to cleavage by a single-strand specific endonuclease such as Mung Bean Nuclease. Therefore, it was possible to distinguish unimolecular from bimolecular double-stranded DNA molecules on the surface by their ability to be cut by single and double-strand specific endonucleases.

In order to remove all molecules that have single-stranded structures and to identify unimolecular double-stranded molecules, the chip was first exhaustively treated with Mung Bean Nuclease. The reduction in the fluorescence signal was greater by about a factor of 2 for the SS regions of the chip, including those with the EcoR1 half-site on the outer strand that were cleaved by EcoR1, than for the 4 DS regions. Following Mung Bean Nuclease treatment, the chip was treated with either DNase I (which cuts all remaining double-stranded molecules) or EcoR1 (which should cut only the remaining double-stranded molecules with the correct sequence). Upon treatment with DNase I, the fluorescence signal in the 4 DS regions was reduced by at least 5-fold more than the signal in the SS regions. Upon EcoR1 treatment, the signal in the single DS region with the correct EcoR1 sequence was reduced by at least a factor of 3 more than the signal in any other region on the chip. Taken together, these results indicated that the surface-bound molecules synthesized with two complementary strands separated by a flexible PEG linker form intramolecular double-stranded structures that were resistant to a single-strand specific endonuclease and were recognized by both a double-strand specific endonuclease, and a sequence-specific restriction enzyme.

Example III

This example illustrates the strategy employed for the preparation of a conformationally restricted hexapeptide.

A glass coverslip having aminopropylsilane spacer groups can be further derivatized on the amino groups with a poly-A oligonucleotide comprising nine adenosine monomers using VLSIPS™ ("light-directed") methods. The tenth adenine monomer to be added will be a 5'-aminopropyl-functionalized phosphoramidite (available from Glen Research or Genosys Biotechnologies). To the amine terminus is then added, in stepwise fashion, the hexapeptide, RQFKVVT (SEQ ID NO: 41), beginning with the carboxyl end of the peptide (i.e., as T-V-V-K-F-Q-R) (SEQ ID NO: 42). A 3'-succinylated nucleoside can then be added under peptide coupling conditions and the nucleotide synthesis of the poly-T tail can be continued to provide a conformationally restricted probe.

It is to be understood that the above description is intended to be illustrative and not restrictive. Many embodiments will be apparent to those of skill in the art upon reviewing the above description. The scope Of the invention should, therefore, be determined not with reference to the above description, but should instead be determined with reference to the appended claims, along with the full scope of equivalents to which such claims are entitled.

XV. Conclusion

The present invention provides greatly improved methods and apparatus for the study of nucleotide sequences and nucleic acid interactions with other molecules. It is to be understood that the above description is intended to be illustrative and not restrictive. Many embodiments and variations of the invention will become apparent to those of skill in the art upon review of this disclosure. Merely by way of example, certain of the embodiments described herein will be applicable to other polymers, such as peptides and proteins, and can utilized other synthesis techniques. The scope of the invention should, therefore, be determined not with reference to the above description, but instead should be determined with reference to the appended claims along with the full scope of equivalents to which such claims are entitled.

The invention claimed is:

1. A method for identifying a base, the method comprising:
a) hybridizing:
a substrate comprising an array of at least $10^6$ different oligonucleotides wherein the oligonucleotides are attached to the substrate via the 3' ends of the oligonucleotides, the 5' ends of the oligonucleotides are phosphorylated, each different oligonucleotide is present in a different predefined region of the array, and each of the different oligonucleotides is complementary to a defined subsequence of a target nucleic acid, and
a nucleic acid sample comprising target nucleic acids, wherein the target nucleic acids hybridize to their complementary oligonucleotides leaving a single stranded 3' overhanging region of the hybridized target nucleic acid, thereby forming target-oligonucleotide hybrid complexes having a single stranded 3' overhanging region;
b) hybridizing the target-oligonucleotide probe hybrid complexes with a pool of labeled, ligatable oligonucleotide probes of a preselected length to form complexes comprising labeled, ligatable probes hybridized to the 3' overhanging region of the hybridized target nucleic acid adjacent to the 5' end of the oligonucleotides;
c) ligating the labeled ligatable oligonucleotide probes to the 5' end of the oligonucleotides with a ligase thereby forming labeled oligonucleotides on the substrate;
d) washing the substrate to remove target nucleic acids and unligated labeled, ligatable probes; and
e) detecting the presence of labeled oligonucleotides on the substrate to identify which base has specifically interacted with the target nucleic acid as an indication of a subsequence that is complementary.

2. The method according to claim 1 wherein the target nucleic acid is ribonucleic acid (RNA).

3. The method according to claim 1 wherein the target nucleic acid is deoxyribonucleic acid (DNA).

4. The method of claim 1, wherein the array of target; oligonucleotide hybrid complexes has been formed on a substrate comprising beads.

5. The method of claim 1 wherein the 5' ends of the oligonucleotides are phosphorylated by treating the array with kinase prior to the hybridization of the labeled, ligatable probes.

* * * * *

SEQUENCE LISTING (1) GENERAL INFORMATION:

(iii) NUMBER OF SEQUENCES: 42

(2) INFORMATION FOR SEQ ID NO: 1:

(i) SEQUENCE CHARACTERISTICS:
      (A) LENGTH: 12 base pairs (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO: 1:

AGCCTAGCTG AA                                                            12

(2) INFORMATION FOR SEQ ID NO: 2:

(i) SEQUENCE CHARACTERISTICS:
            (A) LENGTH: 12 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO: 2:

TTCAGCTAGG CT                                                            12

(2) INFORMATION FOR SEQ ID NO: 3:

(i) SEQUENCE CHARACTERISTICS:
            (A) LENGTH: 10 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO: 3:

TTTTTAAAAA                                                               10

(2) INFORMATION FOR SEQ ID NO: 4:

(i) SEQUENCE CHARACTERISTICS:
            (A) LENGTH: 10 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO: 4:

AAAAATTTTT                                                               10

(2) INFORMATION FOR SEQ ID NO: 5:

(i) SEQUENCE CHARACTERISTICS:
            (A) LENGTH: 26 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO: 5:

AAAGAAAAAA GACAGTACTA AATGGA                                             26

(2) INFORMATION FOR SEQ ID NO: 6:

(i) SEQUENCE CHARACTERISTICS:
            (A) LENGTH: 15 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO: 6:

AGTACTGTNT TTTTT                                                               15

(2) INFORMATION FOR SEQ ID NO: 7:

(i) SEQUENCE CHARACTERISTICS:
              (A) LENGTH: 15 base pairs
              (B) TYPE: nucleic acid
              (C) STRANDEDNESS: single
              (D) TOPOLOGY: linear (ii) MOLECULE TYPE: DNA (xi) SEQUENCE DESCRIPTION: SEQ ID NO: 7:

TAGTACTGNC TTTTT                                                               15

(2) INFORMATION FOR SEQ ID NO: 8:

(i) SEQUENCE CHARACTERISTICS:
              (A) LENGTH: 15 base pairs
              (B) TYPE: nucleic acid
              (C) STRANDEDNESS: single
              (D) TOPOLOGY: linear (ii) MOLECULE TYPE: DNA (xi) SEQUENCE DESCRIPTION: SEQ ID NO: 8:

TTAGTACTNG CTTTT                                                               15

(2) INFORMATION FOR SEQ ID NO: 9:

(i) SEQUENCE CHARACTERISTICS:
              (A) LENGTH: 21 base pairs
              (B) TYPE: nucleic acid
              (C) STRANDEDNESS: single
              (D) TOPOLOGY: linear (ii) MOLECULE TYPE: DNA (xi) SEQUENCE DESCRIPTION: SEQ ID NO: 9:

CTGTATCCGA CATCTGGTTA A                                                        21

(2) INFORMATION FOR SEQ ID NO: 10:

(i) SEQUENCE CHARACTERISTICS:
              (A) LENGTH: 13 base pairs
              (B) TYPE: nucleic acid
              (C) STRANDEDNESS: single
              (D) TOPOLOGY: linear (ii) MOLECULE TYPE: DNA (xi) SEQUENCE DESCRIPTION: SEQ ID NO: 10:

CCAACCAAAC CCC                                                                 13

(2) INFORMATION FOR SEQ ID NO: 11:

(i) SEQUENCE CHARACTERISTICS:
              (A) LENGTH: 13 base pairs
              (B) TYPE: nucleic acid
              (C) STRANDEDNESS: single
              (D) TOPOLOGY: linear (ii) MOLECULE TYPE: DNA (xi) SEQUENCE DESCRIPTION: SEQ ID NO: 11:

CCAACCAAAM NMM                                                                 13

(2) INFORMATION FOR SEQ ID NO: 12:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 12:

```
ACTGTTAGCT AATTGG                                                16
```

(2) INFORMATION FOR SEQ ID NO: 13:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 13:

```
GGGGGGAGCT AACGGG                                                16
```

(2) INFORMATION FOR SEQ ID NO: 14:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 14:

```
TACTGTATTT TTT                                                   13
```

(2) INFORMATION FOR SEQ ID NO: 15:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 15:

```
TACTGTCTTT TTT                                                   13
```

(2) INFORMATION FOR SEQ ID NO: 16:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 16:

```
TACTGTGTTT TTT                                                   13
```

(2) INFORMATION FOR SEQ ID NO: 17:

(i) SEQUENCE CHARACTERISTICS:
        (A) LENGTH: 13 base pairs (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 17:

TACTGTTTTT TTT                                                              13

(2) INFORMATION FOR SEQ ID NO: 18:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 18:

GTACTGACTT TTT                                                              13

(2) INFORMATION FOR SEQ ID NO: 19:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 19:

GTACTGCCTT TTT                                                              13

(2) INFORMATION FOR SEQ ID NO: 20:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 20:

GTACTGGCTT TTT                                                              13

(2) INFORMATION FOR SEQ ID NO: 21:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 21:

GTACTGTCTT TTT                                                              13

(2) INFORMATION FOR SEQ ID NO: 22:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (ii) MOLECULE TYPE: DNA -continued (xi) SEQUENCE DESCRIPTION: SEQ ID NO: 22:

AGTACTATCT TTT                                                           13

(2) INFORMATION FOR SEQ ID NO: 23:

(i) SEQUENCE CHARACTERISTICS:
            (A) LENGTH: 13 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO: 23:

AGTACTCTCT TTT                                                           13

(2) INFORMATION FOR SEQ ID NO: 24:

(i) SEQUENCE CHARACTERISTICS:
            (A) LENGTH: 13 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO: 24:

AGTACTGTCT TTT                                                           13

(2) INFORMATION FOR SEQ ID NO: 25:

(i) SEQUENCE CHARACTERISTICS:
            (A) LENGTH: 13 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO: 25:

AGTACTTTCT TTT                                                           13

(2) INFORMATION FOR SEQ ID NO: 26:

(i) SEQUENCE CHARACTERISTICS:
            (A) LENGTH: 11 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO: 26:

GGGNCCCTTA A                                                             11

(2) INFORMATION FOR SEQ ID NO: 27:

(i) SEQUENCE CHARACTERISTICS:
            (A) LENGTH: 16 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO: 27:

TAAAGTAAGA CATAAC                                                        16

(2) INFORMATION FOR SEQ ID NO: 28:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 28:

GGCTGACGTC AGCAAT                                                         16

(2) INFORMATION FOR SEQ ID NO: 29:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 29:

TTGCTGACAT CAGCC                                                          15

(2) INFORMATION FOR SEQ ID NO: 30:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 30:

TTGCTGACCT CAGCC                                                          15

(2) INFORMATION FOR SEQ ID NO: 31:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 31:

TTGCTGACGT CAGCC                                                          15

(2) INFORMATION FOR SEQ ID NO: 32:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 32:

TTGCTGACTT CAGCC                                                          15

(2) INFORMATION FOR SEQ ID NO: 33:

(i) SEQUENCE CHARACTERISTICS:
        (A) LENGTH: 12 base pairs (B) TYPE: nucleic acid
        (C) STRANDEDNESS: single
        (D) TOPOLOGY: linear (ii) MOLECULE TYPE: DNA (ix) FEATURE:
        (A) NAME/KEY: modified_base
        (B) LOCATION: 12
        (D) OTHER INFORMATION: /mod_base= OTHER
            /note= "N = adenine covalently modified
            at the 3' hydroxyl group with 2
            polyethylene glycol (PEG) spacers"

(xi) SEQUENCE DESCRIPTION: SEQ ID NO: 33:

CNCGCCGCGC AN                                                       12

(2) INFORMATION FOR SEQ ID NO: 34:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: modified_base
        (B) LOCATION: 1
        (D) OTHER INFORMATION: /mod_base= OTHER
            /note= "N = guanine covalently modified
            at the 5' hydroxyl group with a
            fluorescein molecule"

(xi) SEQUENCE DESCRIPTION: SEQ ID NO: 34:

NCGCGGCGCG AACGCAACGC                                               20

(2) INFORMATION FOR SEQ ID NO: 35:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: modified_base
        (B) LOCATION: 12
        (D) OTHER INFORMATION: /mod_base= OTHER
            /note= "N = adenine covalently modified
            at the 3' hydroxyl group with 2
            polyethylene glycol (PEG) spacers"

(xi) SEQUENCE DESCRIPTION: SEQ ID NO: 35:

NCTTACGCGC AN                                                       12

(2) INFORMATION FOR SEQ ID NO: 36:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: modified_base
        (B) LOCATION: 12
        (D) OTHER INFORMATION: /mod_base= OTHER
            /note= "N = adenine covalently modified

```
            at the 3' hydroxyl group with 2
            polyethylene glycol (PEG) spacers"

(xi) SEQUENCE DESCRIPTION: SEQ ID NO: 36:

NCTTAATATA AN                                                            12

(2) INFORMATION FOR SEQ ID NO: 37:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: modified_base
        (B) LOCATION: 1
        (D) OTHER INFORMATION: /mod_base= OTHER
            /note= "N = guanine covalently modified
            at the 5' hydroxyl group with a
            fluorescein molecule"

(xi) SEQUENCE DESCRIPTION: SEQ ID NO: 37:

NCGCGTAAGG CCTTCGACGT AG                                                 22

(2) INFORMATION FOR SEQ ID NO: 38:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: modified_base
        (B) LOCATION: 1
        (D) OTHER INFORMATION: /mod_base= OTHER
            /note= "N = thymine covalently modified
            at the 5' hydroxyl group with a
            fluorescein molecule"

(xi) SEQUENCE DESCRIPTION: SEQ ID NO: 38:

NATATTAAGG CCTTCGACGT AG                                                 22

(2) INFORMATION FOR SEQ ID NO: 39:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: modified_base
        (B) LOCATION: 10
        (D) OTHER INFORMATION: /mod_base= OTHER
            /note= "N = cytosine covalently modified
            at the 3' hydroxyl group with 2
            polyethylene glycol (PEG) spacers"

(xi) SEQUENCE DESCRIPTION: SEQ ID NO: 39:

NNNNNNGCGN                                                               10

(2) INFORMATION FOR SEQ ID NO: 40:

(i) SEQUENCE CHARACTERISTICS:
```

```
        (A) LENGTH: 10 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: modified_base
        (B) LOCATION: 10
        (D) OTHER INFORMATION: /mod_base= OTHER
            /note= "N = cytosine covalently modified
            at the 3' hydroxyl group with 2
            polyethylene glycol (PEG) spacers"

(xi) SEQUENCE DESCRIPTION: SEQ ID NO: 40:

CCTTACGCGN                                                                10

(2) INFORMATION FOR SEQ ID NO: 41:

(i) SEQUENCE CHARACTERISTICS:
        (A) LENGTH: 7 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 41:

Arg Gln Phe Lys Val Val Thr
1               5

(2) INFORMATION FOR SEQ ID NO: 42:

(i) SEQUENCE CHARACTERISTICS:
        (A) LENGTH: 7 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 42:

Thr Val Val Lys Phe Gln Arg
1               5
```